United States Patent [19]

Or et al.

[11] Patent Number: 5,583,139

[45] Date of Patent: Dec. 10, 1996

[54] MARCOLIDE IMMUNOMODULATORS

[75] Inventors: Yat Sun Or; Jay R. Luly, both of Libertyville; Rolf Wagner, Gurnee, all of Ill.

[73] Assignee: Abbott Laboratories, Abbott Park, Ill.

[21] Appl. No.: 423,490

[22] Filed: Apr. 19, 1995

Related U.S. Application Data

[60] Division of Ser. No. 327,391, Oct. 26, 1994, which is a continuation-in-part of Ser. No. 155,064, Nov. 19, 1993, abandoned.

[51] Int. Cl.$^6$ ............ A61K 31/435; C07D 498/22
[52] U.S. Cl. ............ 514/291; 514/63; 540/456; 540/452
[58] Field of Search ............ 514/291, 63

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 5,023,264 | 6/1991 | Caufield et al. | 540/456 |
| 5,100,883 | 3/1992 | Schiehser | 540/456 |
| 5,102,876 | 4/1992 | Caufield | 540/456 |
| 5,118,677 | 6/1992 | Caufield | 540/456 |
| 5,118,678 | 6/1992 | Kao et al. | 540/456 |
| 5,120,842 | 6/1992 | Failli et al. | 540/456 |
| 5,151,413 | 9/1992 | Caufield et al. | 540/456 |
| 5,177,203 | 1/1993 | Failli et al. | 540/456 |
| 5,194,447 | 3/1993 | Kao | 540/456 |
| 5,202,332 | 4/1993 | Hughes et al. | 540/456 |
| 5,206,018 | 4/1993 | Sehgal et al. | 540/456 |
| 5,221,670 | 6/1993 | Caufield | 540/456 |
| 5,233,036 | 8/1993 | Hughes et al. | 540/456 |
| 5,256,790 | 10/1993 | Nelson | 540/456 |
| 5,258,389 | 11/1993 | Goulet et al. | 540/456 |
| 5,260,299 | 11/1993 | Failli et al. | 540/456 |
| 5,260,300 | 11/1993 | Hu | 540/456 |
| 5,262,423 | 11/1993 | Kao | 540/456 |
| 5,262,424 | 11/1993 | Kao | 540/456 |
| 5,302,584 | 4/1994 | Kao | 540/456 |
| 5,302,600 | 4/1994 | Nelson | 540/456 |
| 5,346,893 | 9/1994 | Failli et al. | 540/456 |
| 5,457,111 | 10/1995 | Luly et al. | 514/291 |

FOREIGN PATENT DOCUMENTS

| | | | |
|---|---|---|---|
| 0429436 | 5/1991 | European Pat. Off. | 540/456 |
| 467606 | 1/1992 | European Pat. Off. | 540/456 |
| 507556 | 10/1992 | European Pat. Off. | 540/456 |
| 509795 | 10/1992 | European Pat. Off. | 540/456 |
| 0515140 | 11/1992 | European Pat. Off. | 540/456 |
| 0470804 | 12/1992 | European Pat. Off. | 540/456 |
| 525960 | 2/1993 | European Pat. Off. | 540/456 |
| 533433 | 3/1993 | European Pat. Off. | 540/456 |
| 551182 | 7/1993 | European Pat. Off. | 540/456 |
| 562853 | 9/1993 | European Pat. Off. | 540/456 |
| 568310 | 11/1993 | European Pat. Off. | 540/456 |
| 593227 | 4/1994 | European Pat. Off. | 540/456 |
| 9205179 | 2/1992 | WIPO | 540/456 |
| 9221341 | 10/1992 | WIPO | 540/456 |
| WO93/16189 | 8/1993 | WIPO | 540/456 |
| WO93/18043 | 9/1993 | WIPO | 540/456 |
| WO93/19763 | 10/1993 | WIPO | 540/456 |
| 9311130 | 10/1993 | WIPO | 540/456 |
| WO94/02136 | 2/1994 | WIPO | 540/456 |
| WO94/02137 | 2/1994 | WIPO | 540/456 |
| WO94/02485 | 2/1994 | WIPO | 540/456 |
| WO94/04540 | 3/1994 | WIPO | 540/456 |
| 9409010 | 4/1994 | WIPO | 540/456 |
| WO94/10176 | 5/1994 | WIPO | 540/456 |
| WO94/11380 | 5/1994 | WIPO | 540/456 |

Primary Examiner—Robert T. Bond
Attorney, Agent, or Firm—Steven R. Crowley

[57] ABSTRACT

Novel macrolide compounds of the formula

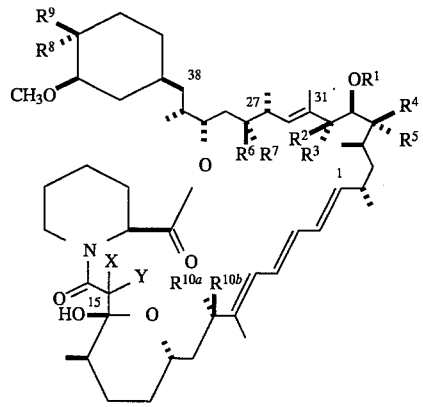

and pharmaceutically acceptable salts, esters, amides and prodrugs thereof, processes for the preparation of the compounds of the invention, intermediates useful in these processes, a pharmaceutical composition, and a method of treating immunomodulatory disorders are disclosed.

6 Claims, No Drawings

MARCOLIDE IMMUNOMODULATORS

This is a division of U.S. patent applicaiton Ser. No. 08/327,391filed Oct. 26, 1994, which is a continuation-in-part of U.S. patent application Ser. No. 155,064, filed Nov. 19, 1993, now abandoned.

TECHNICAL FIELD

The present invention relates to novel chemical compounds having immunomodulatory activity and synthetic intermediates useful for the preparation of the novel compounds, and in particular to macrolide immunomodulators. More particularly, the invention relates to semisynthetic analogs of rapamycin, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Recently, several classes of macrocyclic compounds having potent immunomodulatory activity have been discovered. Okuhara et al., in European Patent Application No. 184,162, published Jun. 11, 1986, disclose a number of macrocyclic compounds isolated from the genus Streptomyces. Immunosuppressant FK-506, isolated from a strain of *S. tsukubaensis*, is a 23-membered macrocyclic lactone represented by the formula shown below.

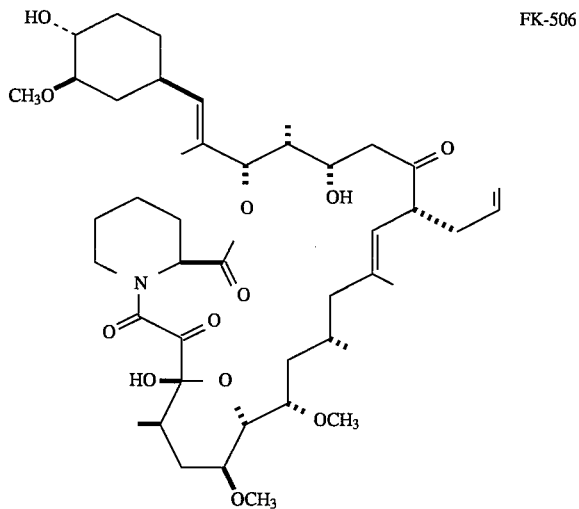

Other related natural products, such as FR-900520 and FR-900523, which differ from FK-506 in their alkyl substituent at C-21, have been isolated from *S. hygroscopicus yakushimnaensis*. Yet another analog, FR-900525, produced by *S. tsukubaensis*, differs from FK-506 in the replacement of a pipecolic acid moiety with a proline group. Unsatisfactory side-effects associated with cyclosporine and FK-506 such as nephrotoxicity, have led to a continued search for immunosuppressant compounds having improved efficacy and safety.

Rapamycin is a macrocyclic triene antibiotic produced by *Streptomyces hygroscopicus*, which was found to have antifungal activity, particularly against *Candida albicans*, both in vitro and in vivo (C. Vezina et al., *J. Antibiot.* 1975, 28, 721; S. N. Sehgal et al., *J. Antibiot.* 1975, 28, 727; H. A. Baker et al., *J. Antibiot.* 1978, 31, 539; U.S. Pat. No. 3,929,992; and U.S. Pat. No. 3,993,749).

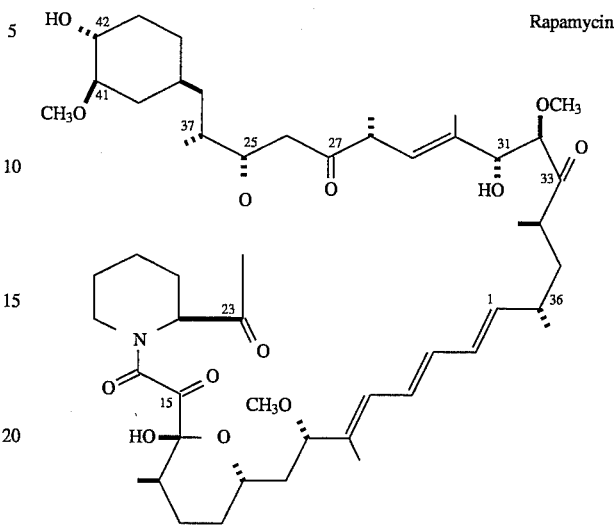

Rapamycin alone (U.S. Pat. No. 4,885,171) or in combination with picibanil (U.S. Pat. No. 4,401,653) has been shown to have antitumor activity. In 1977, rapamycin was also shown to be effective as an immunosuppressant in the experimental allergic encephalomyelitis model, a model for multiple sclerosis; in the adjuvant arthritis model, a model for rheumatoid arthritis; and was shown to effectively inhibit the formation of IgE-like antibodies (R. Martel et at., *Can. J. Physiol. Pharmacol.*, 1977, 55, 48).

The immunosuppressive effects of rapamycin have also been disclosed in FASEB, 1989, 3, 3411 as has its ability to prolong survival time of organ grafts in histoincompatible rodents (R. Morris, *Med. Sci. Res.*, 1989, 17, 877). The ability of rapamycin to inhibit T-cell activation was disclosed by M. Strauch (FASEB, 1989, 3, 3411). These and other biological effects of rapamycin are reviewed in Transplantation Reviews, 1992, 6, 39–87.

Mono-ester and di-ester derivatives of rapamycin (esterification at positions 31 and 42) have been shown to be useful as antifungal agents (U.S. Pat. No. 4,316,885) and as water soluble prodrugs of rapamycin (U.S. Pat. No. 4,650,803).

Fermentation and purification of rapamycin and 30-demethoxy rapamycin have been described in the literature (C. Vezina et al. *J. Antibiot.* (Tokyo), 1975, 28 (10), 721; S. N. Sehgal et al., *J. Antibiot.* (Tokyo), 1975, 28(10), 727; 1983, 36(4), 351; N. L. Pavia et al., *J. Natural Products*, 1991, 54(1), 167–177).

Numerous chemical modifications of rapamycin have been attempted. These include the preparation of mono- and di-ester derivatives of rapamycin (WO 92/05179), 27-oximes of rapamycin (EP0 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occuring enantiomeric form (K. C. Nicolaou et at., *J. Am. Chem. Soc.*, 1993, 115, 4419–4420; S. L. Schreiber, *J. Am. Chem. Soc.*, 1993, 115, 7906–7907; S. J. Danishefsky, *J. Am. Chem. Soc.*, 1993, 115, 9345–9346.

It has been known that rapamycin, like FK-506, binds to FKBP-12 (Siekierka, J. J.; Hung, S. H. Y.; Poe, M.; Lin, C. S.; Sigal, N. H. *Nature*, 1989, 341, 755–757; Harding, M. W.; Galat, A.; Uehling, D. E.; Schreiber, S. L. *Nature* 1989, 341, 758–760; Dumont, F. J.; Melino, M. R.; Staruch, M. J.;

Koprak, S. L.; Fischer, P. A.; Sigal, N. H. *J. Immunol.* 1990, 144, 1418–1424; Bierer, B. E.; Schreiber, S. L.; Burakoff, S. J. *Eur. J. Immunol.* 1991, 21,439–445; Fretz, H.; Albers, M. W.; Galat, A.; Standaert, R. F.; Lane, W. S.; Burakoff, S. J.; Bierer, B. E.; Schreiber, S. L. *J. Am. Chem. Soc.* 1991, 113, 1409–1411). Recently it has been discovered that the rapamycin/FKBP-12 complex binds to yet another protein, which is distinct from calcineurin, the protein that the FK-506/FKBP-12 complex inhibits (Brown, E. J.; Albers, M. W.; Shin, T. B.; Ichikawa, K.; Keith, C. T.; Lane, W. S.; Schreiber, S. L. *Nature* 1994, 369, 756–758.; Sabatini, D. M.; Erdjument-Bromage, H.; Lui, M.; Tempest, P.; Snyder, S. H. *Cell,* 1994, 78, 35–43).

Although some of these modified compounds exhibit immunosuppressive activity, the need remains for macrocyclic immunosuppressants which do not have the serious side effects frequently associated with immunosuppressant therapy. Accordingly, one object of this invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, at least-one of the above compounds. Yet another object of the invention is to provide a method of treating a variety of disease states, including post-transplant tissue rejection and autoimmune disfunction.

DISCLOSURE OF THE INVENTION

In one aspect of the present invention there are compounds of the formula I:

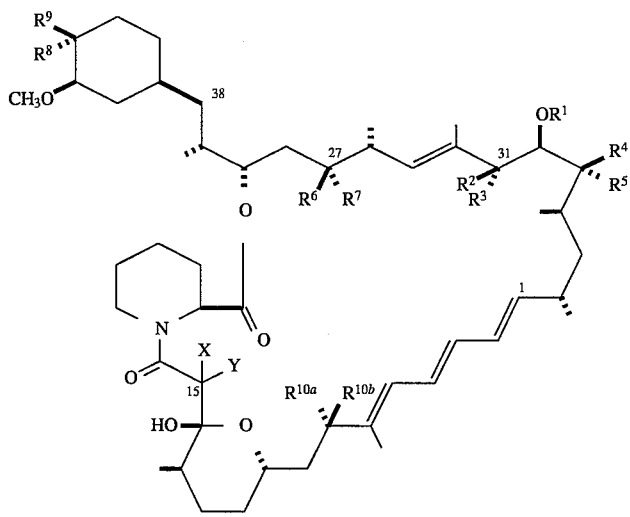

wherein $R^1$ is hydrogen, a hydroxy protecting group, loweralkyl or phenyl-substituted loweralkyl;

$R^2$ is hydrogen and $R^3$ is hydroxy or protected hydroxy or $R^2$ and $R^3$ taken together are oxo;

$R^4$ is hydrogen or phenyl-substituted loweralkyl and $R^5$ is hydroxy or protected hydroxy or $R^5$ is hydrogen or phenyl-substituted loweralkyl and $R^4$ is hydroxy or protected hydroxy or $R^4$ and $R^5$ taken together are oxo;

$R^6$ is hydrogen or phenyl-substituted loweralkyl and $R^7$ is hydrogen, hydroxy or protected hydroxy or $R^7$ is hydrogen or phenyl-substituted loweralkyl and $R^6$ is hydroxy or protected hydroxy or $R^6$ and $R^7$ taken together are (1) oxo,
(2) diazo,
(3) $=CH_2$
(4) $-O-(CH_2)_2-O-$,
(5) $-S-(CH_2)_2-S-$,
(6) $-O-(CH_2)_3-O-$,
(7) $-S-(CH_2)_3-S-$,
(8) $=N-OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(9) $=N-N(R^{21})(R^{22})$ wherein $R^{21}$ and $R^{22}$ are independently selected from hydrogen, loweralkyl, aryl, arylalkyl, heterocyclic and heterocyclicalkyl;

$R^8$ is hydrogen;

$R^9$ is (1) $-OS(O)_2CF_3$,
(2) $-OS(O)_2F$,
(3) $-OS(O)_2R^{21a}$ wherein $R^{21a}$ is loweralkyl, aryl, arylalkyl, heterocyclic or heterocyclicalkyl,
(4) $-OC(O)R^{23}$ wherein $R^{23}$ is loweralkyl, cycloalkyl, cycloalkylalkyl, aryl, arylalkyl, heterocyclic, heterocyclicalkyl, alkoxy, $-O$-cycloalkyl, $-O$-aryl,$-O$-heterocyclic,$-O-$(N-succinimidyl) or 5-tetrazolyl;
(5) $-OC(O)-N(R^{24})(R^{25})$ wherein $R^{24}$ and $R^{25}$ are independently selected from (a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
 (i) hydroxy,
 (ii) $-COOH$,
 (iii) $-CN$, (iv) —Q-loweralkyl, —Q-aryl, —Q-(arylalkyl), —Q—, heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein R$^{27}$ is hydrogen, loweralkyl, aryl or heterocyclic, (v) cycloalkyl,
(vi) aryl,
(vii) heterocyclic,
(viii) —N(R$^{28}$)(R$^{29}$) wherein R$^{28}$ and R$^{29}$ are independently selected from hydrogen, loweralkyl, hydroxyalkyl, aryl and heterocyclic,
(ix) guanidino,
(x) —S(O)$_2$R$^{11}$ wherein R$^{11}$ is loweralkyl, aryl or arylalkyl,
(xi) —OS(O)$_2$R$^{11}$ wherein R$^{11}$ is defined as above,
(xii) —SO$_3$H,
(xiii) —S(O)$_2$NH$_2$,
(xiv) —SR$^{28}$ wherein R$^{28}$ is deemed as above,
(xv) halogen,
(xvi) oxo and
(xvii) epoxy;
(g) aryl,
(h) heterocyclic,
(i) —NHC(O)—O-loweralkyl,
—NHC(O)-aryl,
(k) —NHC(O)-heterocyclic and
(l) loweralkyl substituted by —OC(O)—R$^f$ wherein R$^f$ is carboxyalkyl
or —N(R$^{24}$)(R$^{25}$) taken together form a nitrogen-containing heterocyclic group,
(6) -OR$^{25}$ wherein R$^{25}$ is as deemed above,
(7) a protected hydroxy group,
(8) —OC(O)N(OR$^{24}$)(R$^{25}$) wherein R$^{24}$ and R$^{25}$ are defined as above,
(9) —O(CH$_2$)$_i$C(O)OR$^{20}$ wherein i is one or two and R$^{20}$ is independently defined as above,
(10) —O(CH(Si(CH$_3$)$_3$))—(CH$_2$)$_j$C(O)OR$^{20}$ wherein j is zero or one and R$^{20}$ is independently defined as above,
(11) —O(CH$_2$)$_i$C(O)N(R$^{24}$)(R$^{25}$) wherein i, R$^{24}$ and R$^{25}$ are defined as above,
(12) —O(CH$_2$)$_i$C(O)N(OR$^{24}$)(R$^{25}$) wherein i, R$^{24}$ and R$^{25}$ are defined as above,
(13) —O(CH$_2$)$_i$C(O)N(R$^{24}$)(N(R$^{24}$)(R$^{25}$)) wherein i, R$^{24}$ and R$^{25}$ are defined as above,
(14) —O(CH$_2$)$_i$NHC(O)N(R$^{24}$)(R$^{25}$) wherein i, R$^{24}$ and R$^{25}$ are defined as above,
(15) —O(CH$_2$)$_i$NHC(O)N(OR$^{24}$)(R$^{25}$) wherein i, R$^{24}$ and R$^{25}$ are defined as above,
(16) —O(CH$_2$)$_i$NHC(O)N(R$^{24}$)(N(R$^{24}$)(R$^{25}$)) wherein i, R$^{24}$ and R$^{25}$ are defined as above,
(17) —OS(O)$_2$N(R$^{24}$)(R$^{25}$) wherein R$^{24}$ and R$^{25}$ are defined as above,
(18) —O(CH$_2$)$_i$—NHC(O)R$^{24}$ wherein R$^{24}$ is defined as above,
(19) —OCH(R$^{24}$)—SH wherein R$^{24}$ is defined as above,
(20) —OCH(R$^{24}$)—S-loweralkyl wherein R$^{24}$ is defined as above,
(21) —OCH(R$^{24}$)—S-aryl wherein R$^{24}$ is defined as above and
(22) —N$_3$;

R$^{10a}$ is hydrogen and R$^{10b}$ is hydrogen, hydroxy, protected hydroxy, alkoxy, alkenyl, alkenyloxy, halogen or —SR$^{28}$ wherein R$^{28}$ is independently defined as above or R$^{10b}$ is hydrogen and R$^{10a}$ is hydrogen, hydroxy, protected hydroxy, alkoxy, alkenyl, alkenyloxy, halogen or —SR$^{28}$ wherein R$^{28}$ is independently defined as above or R$^{10a}$ and R$^{10b}$ are both alkoxy or —SR$^{28a}$ wherein R$^{28a}$ is loweralkyl, aryl or heterocyclic or R$^{10a}$ and R$^{10b}$ taken together are oxo; and X is hydrogen and Y is hydrogen, hydroxy or protected hydroxy or Y is hydrogen and X is hydroxy or protected hydroxy or X and Y taken together are oxo;
or a pharmaceutically acceptable salt, ester, amide or pro-drug thereof.

Preferred compounds of the formula I are those wherein:
R$^1$ is methyl;
R$^2$ is hydrogen and R$^3$ is hydroxy;
R$^4$ is hydrogen and R$^5$ is hydroxy or R$^5$ is hydrogen and R$^4$ is hydroxy or R$^4$ and
R$^5$ taken together are oxo;
R$^6$ and R$^7$ are defined as above;
R$^8$ is hydrogen;
R$^9$ is defined as above;
R$^{10a}$ is hydrogen, methoxy or fluoro and R$^{10b}$ is hydrogen; and
X and Y taken together are oxo.

More preferred compounds of the formula I are those wherein:
R$^1$ is methyl;
R$^2$ is hydrogen and R$^3$ is hydroxy;
R$^4$ is hydrogen and R$^5$ is hydroxy or R$^5$ is hydrogen and R$^4$ is hydroxy or R$^4$ and
R$^5$ taken together are oxo;
R$^6$ and R$^7$ taken together are
(1) oxo,
(2) =N—OR$^{20}$ wherein R$^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein R$^{21}$ and R$^{22}$ are independently selected from hydrogen, loweralkyl, aryl, arylalkyl, heterocyclic and heterocyclicalkyl;
R$^8$ is hydrogen;
R$^9$ is
(1) —OH,
(2) —OC(O)R$^{23}$ wherein R$^{23}$ is —O-aryl, —O—(N-succinimidyl), —O—benzotriazolyl, —O-2'-pyridyl or 5-tetrazolyl,
(3) —OC(O)—N(R$^{24}$)(R$^{25}$) wherein R$^{24}$ and R$^{25}$ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from (i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein R$^{27}$ is hydrogen, loweralkyl, aryl or heterocyclic,
(v) cycloalkyl,
(vi) aryl,
(vii) heterocyclic,
(viii) —N(R$^{28}$)(R$^{29}$) wherein R$^{28}$ and R$^{29}$ are independently selected from hydrogen, loweralkyl, hydroxyalkyl, aryl and heterocyclic,
(ix) guanidino,
(x) —S(O)$_2$R$^{11}$ wherein R$^{11}$ is loweralkyl, aryl or arylalkyl,
(xi) —OS(O)$_2$R$^{11}$ wherein R$^{11}$ is defined as above,
(xii) —SO$_3$H,
(xiii) —S(O)$_2$NH$_2$,
(xiv) —SR$^{28}$ wherein R$^{28}$ is defined as above,
(xv) halogen,
(xvi) oxo and
(xvii) epoxy;
(g) aryl,
(h) heterocyclic,
(i) —NHC(O)—O-loweralkyl,
(j) —NHC(O)-aryl,
(k) —NHC(O)-heterocyclic and
(l) loweralkyl substituted by —OC(O)—R$^f$ wherein R$^f$ is carboxyalkyl or —N(R$^{24}$)(R$^{25}$) taken together form a nitrogen-containing heterocyclic group,
(4) —OC(O)N(OR$^{24}$)(R$^{25}$) wherein R$^{24}$ and R$^{25}$ are defined as above,
(5) —O(CH$_2$)$_i$C(O)N(R$^{24}$)(R$^{25}$) wherein is one or two and R$^{24}$ and R$^{25}$ are defined as above,
(6) —O(CH$_2$)$_i$C(O)N(OR$^{24}$)(R$^{25}$) wherein i, R$^{24}$ and R$^{25}$ are defined as above,
(7) —O(CH$_2$)$_i$NHC(O)N(R$^{24}$)(R$^{25}$) wherein i, R$^{24}$ and R$^{25}$ are defined as above or
(8) —O(CH$_2$)$_i$NHC(O)N(OR$^{24}$)(R$^{25}$) wherein i, R$^{24}$ and R$^{25}$ are defined as above;

R$^{10a}$ is hydrogen, methoxy or fluoro and R$^{10b}$ is hydrogen; and X and Y taken together are oxo.

Even more preferred compounds of the formula I are those wherein:

R$^1$ is methyl;

R$^2$ is hydrogen and R$^3$ is hydroxy;

R$^4$ and R$^5$ taken together are oxo;

R$^6$ and R$^7$ taken together are
(1) oxo,
(2) =N—OR$^{20}$ wherein R$^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein R$^{21}$ and R$^{22}$ are independently selected from hydrogen, loweralkyl, aryl, arylalkyl, heterocyclic and heterocyclicalkyl;

R$^8$ is hydrogen;

R$^9$ is
(1) —OH,
(2) —OC(O)R$^{23}$ wherein R$^{23}$ is —O-aryl, —O—(N-succinimidyl), —O—benzotriazolyl, —O-2'-pyridyl or 5-tetrazolyl,
(3) —OC(O)—N(R$^{24}$)(R$^{25}$) wherein R$^{24}$ and R$^{25}$ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
(i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein R$^{27}$ is hydrogen, loweralkyl, aryl or heterocyclic,
(v) cycloalkyl,
(vi) aryl,
(vii) heterocyclic,
(viii) —N(R$^{28}$)(R$^{29}$) wherein R$^{28}$ and R$^{29}$ are independently selected from hydrogen, loweralkyl, hydroxyalkyl, aryl and heterocyclic,
(ix) guanidino,
(x) —S(O)$_2$R$^{11}$ wherein R$^{11}$ is loweralkyl, aryl or arylalkyl,
(xi) —OS(O)$_2$R$^{11}$ wherein R$^{11}$ is defined as above,
(xii) —SO$_3$H,
(xiii) —S(O)$_2$NH$_2$,
(xiv) —SR$^{28}$ wherein R$^{28}$ is defined as above,
(xv) halogen,
(xvi) oxo and
(xvii) epoxy;
(g) aryl,
(h) heterocyclic,
(i) —NHC(O)—O-loweralkyl,
(j) —NHC(O)-aryl,
(k) —NHC(O)-heterocyclic and
(l) loweralkyl substituted by —OC(O)—R$^f$ wherein R$^f$ is carboxyalkyl or —N(R$^{24}$)(R$^{25}$) taken together form a nitrogen-containing heterocyclic group,
(4) —OC(O)N(OR$^{24}$)(R$^{25}$) wherein R$^{24}$ and R$^{25}$ are defined as above,
(5) —O(CH$_2$)$_i$C(O)N(R$^{24}$)(R$^{25}$) wherein iis one or two and R$^{24}$ and R$^{25}$ are defined as above,
(6) —O(CH$_2$)$_i$C(O)N(OR$^{24}$)(R$^{25}$) wherein i, R$^{24}$ and R$^{25}$ are defined as above,
(7) —O(CH$_2$)$_i$NHC(O)N(R$^{24}$)(R$^{25}$) wherein i, R$^{24}$ and R$^{25}$ are defined as above or (8) —O(CH$_2$)$_i$NHC(O)N(OR$^{24}$)(R$^{25}$) wherein i, R$^{24}$ and R$^{25}$ are defined as above;

R$^{10a}$ is methoxy and R$^{10b}$ is hydrogen; and

X and Y taken together are oxo.

Most preferred compounds of the formula I are those wherein:

R$^1$ is methyl;

R$^2$ is hydrogen and R$^3$ is hydroxy;

R$^4$ and R$^5$ taken together are oxo;

R$^6$ and R$^7$ taken together are oxo;

R$^8$ is hydrogen;

R$^9$ is —OH, —O-loweralkyl or —OC(O)N(R$^{24}$)(R$^{25}$) wherein R$^{24}$ and R$^{25}$ are defined as above;

R$^{10a}$ is methoxy and R$^{10b}$ is hydrogen; and

X and Y taken together are oxo.

In another aspect of the present invention there are compounds of the formula II:

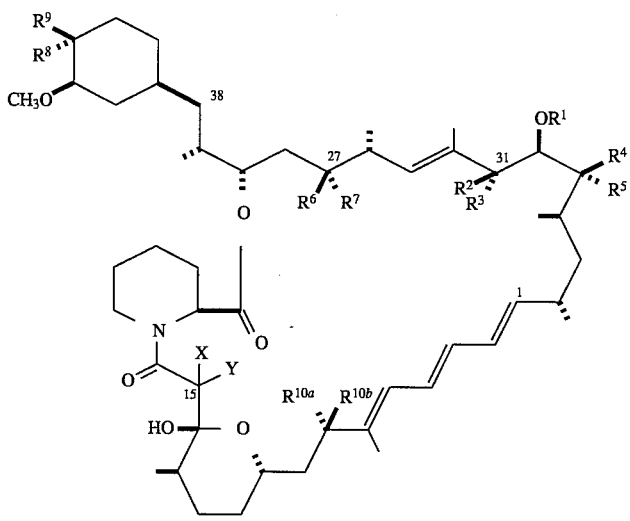

II wherein

R$^1$ is hydrogen, a hydroxy protecting group, loweralkyl or phenyl-substituted loweralkyl;

R$^2$ is hydrogen and R$^3$ is hydroxy or protected hydroxy or R$^2$ and R$^3$ taken together are oxo;

R$^4$ is hydrogen or phenyl-substituted loweralkyl and R$^5$ is hydroxy or protected hydroxy or R$^5$ is hydrogen or phenyl-substituted loweralkyl and R$^4$ is hydroxy or protected hydroxy or R$^4$ and R$^5$ taken together are oxo;

R$^6$ is hydrogen or phenyl-substituted loweralkyl and R$^7$ is hydrogen, hydroxy or protected hydroxy or R$^7$ is hydrogen or phenyl-substituted loweralkyl and R$^6$ is hydroxy or protected hydroxy or R$^6$ and R$^7$ taken together are (1) oxo, (2) diazo, (3) =CH$_2$ (4) —O—(CH$_2$)$_2$—O—, (5) —S—(CH$_2$)$_2$—S—, (6) —O—(CH$_2$)$_3$—O—, (7) —S—(CH$_2$)$_3$—S—, (8) =N—OR$^{20}$ wherein R$^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or (9) =N—N(R$^{21}$)(R$^{22}$) wherein R$^{21}$ and R$^{22}$ are independently selected from hydrogen, loweralkyl, aryl, arylalkyl, heterocyclic and heterocyclicalkyl;

R$^8$ is hydrogen;

R$^9$ is (1) —SR$^{24}$ wherein R$^{24}$ is (a) hydrogen, (b) loweralkyl, (c) alkenyl, (d) alkynyl, (e) cycloalkyl, (f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from (i) hydroxy, (ii) —COOH, (iii) —CN, (iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —(O)O—, —(O)C(O)—O—, —O—C(O)C(O)—, —C(O)NH—, —NHC(O)—, —OC(O)NH—, —NH-C(O)O—, —NH—(O)—NH—, —S(O)$_2$NH—, —NHS(O)$_2$——N(R$^{27}$)—, —C(NR$^{27}$)NHNH— and —NHNHC(NR$^{27}$) — wherein R$^{27}$ is hydrogen, loweralkyl, aryl or heterocyclic, (v) cycloalkyl, (vi) aryl, (vii) heterocyclic, (viii) —N(R$^{28}$)(R$^{29}$) wherein R$^{28}$ and R$^{29}$ are independently selected from hydrogen, loweralkyl, hydroxyalkyl, aryl and heterocyclic, (ix) guanidino, (x) —S(O)$_2$R$^{11}$ wherein R$^{11}$ is loweralkyl, aryl or arylalkyl, (xi) —OS(O)$_2$R$^{11}$ wherein R$^{11}$ is defined as above, (xii) —SO$_3$H, (xiii) —S(O)$_2$NH$_2$, (xiv) —SR$^{28}$ wherein R$^{28}$ is defined as above, (xv) halogen,
(xvi) oxo and
(xvii) epoxy;
(g) aryl,
(h) heterocyclic,
(i) —C(O)—O-loweralkyl,
(j) —C(O)-aryl,
(k) —(O)-heterocyclic or
(l) loweralkyl substituted by —OC(O)—$R^f$ wherein $R^f$ is carboxyalkyl,
(2) —SC(=NH)—$NH_2$,
(3) —SC(=N—$NH_2$)—$NH_2$,
(4) —Se-phenyl or
(5) —Se(O)—phenyl;

$R^{10a}$ is hydrogen and $R^{10b}$ is hydrogen, hydroxy, protected hydroxy, alkoxy, alkenyl, alkenyloxy, halogen or —$SR^{28}$ wherein $R^{28}$ is independently defined as above or $R^{10b}$ is hydrogen and $R^{10a}$ is hydrogen, hydroxy, protected hydroxy, alkoxy, alkenyl, alkenyloxy, halogen or —$SR^{28}$ wherein $R^{28}$ is independently defined as above or $R^{10a}$ and $R^{10b}$ are both alkoxy or —$SR^{28a}$ wherein $R^{28a}$ is loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula II are those wherein:

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R^5$ taken together are oxo;

$R^6$ and $R^7$ are defined as above;

$R^8$ is hydrogen;

$R^9$ is —$SR^{24}$ wherein $R^{24}$ is defined as above;

$R^{10a}$ is hydrogen, methoxy or fluoro and $R^{10b}$ is hydrogen; and

X and Y taken together are oxo.

More preferred compounds of the formula H are those wherein:

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R^5$ taken together are oxo;

$R^6$ and $R^7$ taken together are
(1) oxo,
(2) =N—$OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N($R^{21}$)($R^{22}$) wherein $R^{21}$ and $R^{22}$ are independently selected from hydrogen, loweralkyl, aryl, arylalkyl, heterocyclic and heterocyclicalkyl;

$R^8$ is hydrogen;

$R^9$ is —$SR^{24}$ wherein $R^{24}$ is hydrogen, loweralkyl, substituted loweralkyl as defined above, aryl or heterocyclic;

$R^{10a}$ is hydrogen, methoxy or fluoro and $R^{10b}$ is hydrogen; and

X and Y taken together are oxo.

Even more preferred compounds of the formula II are those wherein:

$R^1$ is methyl;

$R^2$ is hydrogen and $R^3$ is hydroxy;

$R^4$ and $R^5$ taken together are oxo;

$R^6$ and $R^7$ taken together are oxo;

$R^8$ is hydrogen;

$R^9$ is —$SR^{24}$ wherein $R^{24}$ is hydrogen, loweralkyl, substituted loweralkyl as defined above, aryl or heterocyclic;

$R^{10a}$ is methoxy and $R^{10b}$ is hydrogen; and

X and Y taken together are oxo.

Most preferred compounds of the formula II are those wherein:

$R^1$ is methyl;

$R^2$ is hydrogen and $R^3$ is hydroxy;

$R^4$ and $R^5$ taken together are oxo;

$R^6$ and $R^7$ taken together are oxo;

$R^8$ is hydrogen;

$R^9$ is —$SR^{24}$ wherein $R^{24}$ is hydrogen, imidazol-2-yl or N-methyl,imidazol-2-yl;

$R^{10a}$ is methoxy and $R^{10b}$ is hydrogen; and

X and Y taken together are oxo.

In another aspect of the present invention there are compounds of the formula III:

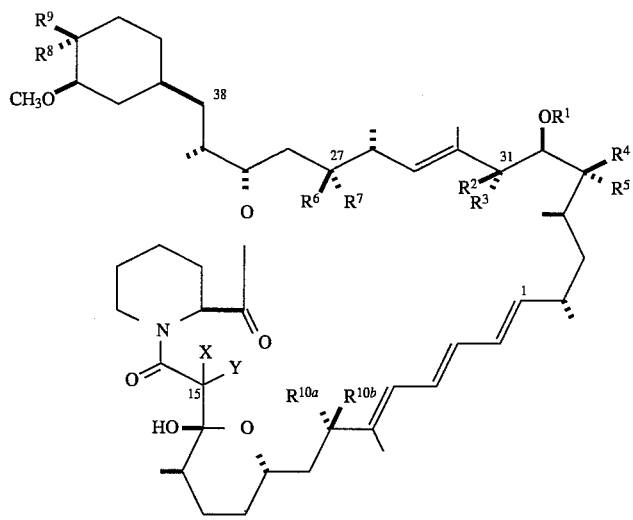

III wherein
R¹ is hydrogen, a hydroxy protecting group, loweralkyl or phenyl-substituted loweralkyl;

R² is hydrogen and R³ is hydroxy or protected hydroxy or R² and R³ taken together are oxo;

R⁴ is hydrogen or phenyl-substituted loweralkyl and R⁵ is hydroxy or protected hydroxy or R⁵ is hydrogen or phenyl-substituted loweralkyl and R⁴ is hydroxy or protected hydroxy or R⁴ and R⁵ taken together are oxo;

R⁶ is hydrogen or phenyl-substituted loweralkyl and R⁷ is hydrogen, hydroxy or protected hydroxy or R⁷ is hydrogen or phenyl-substituted loweralkyl and R⁶ is hydroxy or protected hydroxy or R⁶ and R⁷ taken together are
(1) oxo,
(2) diazo,
(3) =CH₂
(4) —O—(CH₂)₂—O—,
(5) —S—(CH₂)₂—S—,
(6) —O—(CH₂)₃—O—,
(7) —S—(CH₂)₃—S—,
(8) =N—OR²⁰ wherein R²⁰ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(9) =N—N(R²¹)(R²²) wherein R²¹ and R²² are independently selected from hydrogen, loweralkyl, aryl, arylalkyl, heterocyclic and heterocyclicalkyl;

R⁸ is hydrogen;
R⁹ is
(1) —N(R²⁴)(R²⁵) wherein R²⁴ and R²⁵ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from (i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)₂—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)₂NH—, —NHS(O)₂—, —N(R²⁷)—, —C(NR²⁷)NHNH— and —NHNHC(NR²⁷)— wherein R²⁷ is hydrogen, loweralkyl, aryl or heterocyclic,
(v) cycloalkyl,
(vi) aryl,
(vii) heterocyclic,
(viii) —N(R²⁸)(R²⁹) wherein R²⁸ and R²⁹ are independently selected from hydrogen, loweralkyl, hydroxyalkyl, aryl and heterocyclic,
(ix) guanidino,
(x) —S(O)₂R¹¹ wherein R¹¹ is loweralkyl, aryl or arylalkyl,
(xi) —OS(O)₂R¹¹ wherein R¹¹ is defined as above,
(xii) —SO₃H,
(xiii) —S(O)₂NH₂,
(xiv) —SR²⁸ wherein R²⁸ is defined as above,
(xv) halogen,
(xvi) oxo and
(xvii) epoxy;
(g) aryl,
(h) heterocyclic,
(i) —NHC(O)—O-loweralkyl,
(j) —NHC(O)-aryl,
(k) —NHC(O)-heterocyclic and
(l) loweralkyl substituted by —OC(O)—Rᶠ wherein Rᶠ is carboxyalkyl,
(2) —N=C=O,
(3) —NHC(O)—R* or
(4) —NHS(O)₂—R* wherein R* is
(a) loweralkyl,
(b) cycloalkyl,
(c) aryl,
(d) heterocyclic,
(e) loweralkyl substituted by one or two substituents independently selected from (i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein R$^{27}$ is hydrogen, loweralkyl, aryl or heterocyclic,
(v) cycloalkyl,
(vi) aryl,
(vii) heterocyclic,
(viii) —N(R$^{28}$)(R$^{29}$) wherein R$^{28}$ and R$^{29}$ are independently selected from hydrogen, loweralkyl, hydroxyalkyl, aryl and heterocyclic,
(ix) guanidino,
(x) —S(O)$_2$R$^{11}$ wherein R$^{11}$ is loweralkyl, aryl or arylalkyl,
(xi) —OS(O)$_2$R$^{11}$ wherein R$^{11}$ is defined as above,
(xii) —SO$_3$H,
(xiii) —S(O)$_2$NH$_2$,
(xiv) —SR$^{28}$ wherein R$^{28}$ is defined as above,
(xv) halogen,
(xvi) oxo and
(xvii) epoxy;
(f) —N(R$^a$)(R$^b$) wherein R$^a$ and R$^b$ are independently selected from hydrogen, loweralkyl and —N(R$^c$)(R$^d$) wherein R$^c$ and R$^d$ are independently selected from hydrogen and loweralkyl or
(g) —OR* wherein R* is defined as above;

R$^{10a}$ is hydrogen and R$^{10b}$ is hydrogen, hydroxy, protected hydroxy, alkoxy, alkenyl, alkenyloxy, halogen or —SR$^{28}$ wherein R$^{28}$ is independently defined as above or R$^{10b}$ is hydrogen and R$^{10a}$ is hydrogen, hydroxy, protected hydroxy, alkoxy, alkenyl, alkenyloxy, halogen or —SR$^{28}$ wherein R$^{28}$ is independently defined as above or R$^{10a}$ and R$^{10b}$ are both alkoxy or —SR$^{28a}$ wherein R$^{28a}$ is loweralkyl, aryl or heterocyclic or R$^{10a}$ and R$^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula III are those wherein:

R$^1$ is methyl;

R$^2$ is hydrogen and R$^3$ is hydroxy;

R$^4$ is hydrogen and R$^5$ is hydroxy or R$^5$ is hydrogen and R$^4$ is hydroxy or R$^4$ and R$^5$ taken together are oxo;

R$^6$ and R$^7$ are defined as above;

R$^8$ is hydrogen;

R$^9$ is —N(R$^{24}$)(R$^{25}$) wherein R$^{24}$ and R$^{25}$ are defined as above;

R$^{10a}$ is hydrogen, methoxy or fluoro and R$^{10b}$ is hydrogen; and

X and Y taken together are oxo.

More preferred compounds of the formula III are those wherein:

R$^1$ is methyl;

R$^2$ is hydrogen and R$^3$ is hydroxy;

R$^4$ is hydrogen and R$^5$ is hydroxy or R$^5$ is hydrogen and R$^4$ is hydroxy or R$^4$ and R$^5$ taken together are oxo;

R$^6$ and R$^7$ taken together are
(1) oxo,
(2) =N—OR$^{20}$ wherein R$^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein R$^{21}$ and R$^{22}$ are independently selected from hydrogen, loweralkyl, aryl, arylalkyl, heterocyclic and heterocyclicalkyl;

R$^8$ is hydrogen;

R$^9$ is —N(R$^{24}$)(R$^{25}$) wherein R$^{24}$ and R$^{25}$ are independently selected from hydrogen, loweralkyl, substituted loweralkyl as defined above, —NHC(O)—O-loweralkyl, —NHC(O)-aryl and —NHC(O)-heterocyclic or R$^{24}$ and R$^{25}$ taken together form a heterocyclic ring;

R$^{10a}$ is hydrogen, methoxy or fluoro and R$^{10b}$ is hydrogen; and

X and Y taken together are oxo.

Even more preferred compounds of the formula III are those wherein:

R$^1$ is methyl;

R$^2$ is hydrogen and R$^3$ is hydroxy;

R$^4$ and R$^5$ taken together are oxo;

R$^6$ and R$^7$ taken together are oxo;

R$^8$ is hydrogen;

R$^9$ is —N(R$^{24}$)(R$^{25}$) wherein R$^{24}$ and R$^{25}$ are independently selected from hydrogen, loweralkyl, substituted loweralkyl as defined above, —NHC(O)—O-loweralkyl, —NHC(O)-aryl and —NHC(O)-heterocyclic or R$^{24}$ and R$^{25}$ taken together form a heterocyclic ring;

R$^{10a}$ is methoxy and R$^{10b}$ is hydrogen; and

X and Y taken together are oxo.

Most preferred compounds of the formula III are those wherein:

R$^1$ is methyl;

R$^2$ is hydrogen and R$^3$ is hydroxy;

R$^4$ and R$^5$ taken together are oxo;

R$^6$ and R$^7$ taken together are oxo;

R$^8$ is hydrogen;

R$^9$ is —NH$_2$, 2-pyridon-1-yl or 4-pyridon-1-yl;

R$^{10a}$ is methoxy and R$^{10b}$ is hydrogen; and

X and Y taken together are oxo.

In another aspect of the present invention there are compounds of the formula IV:

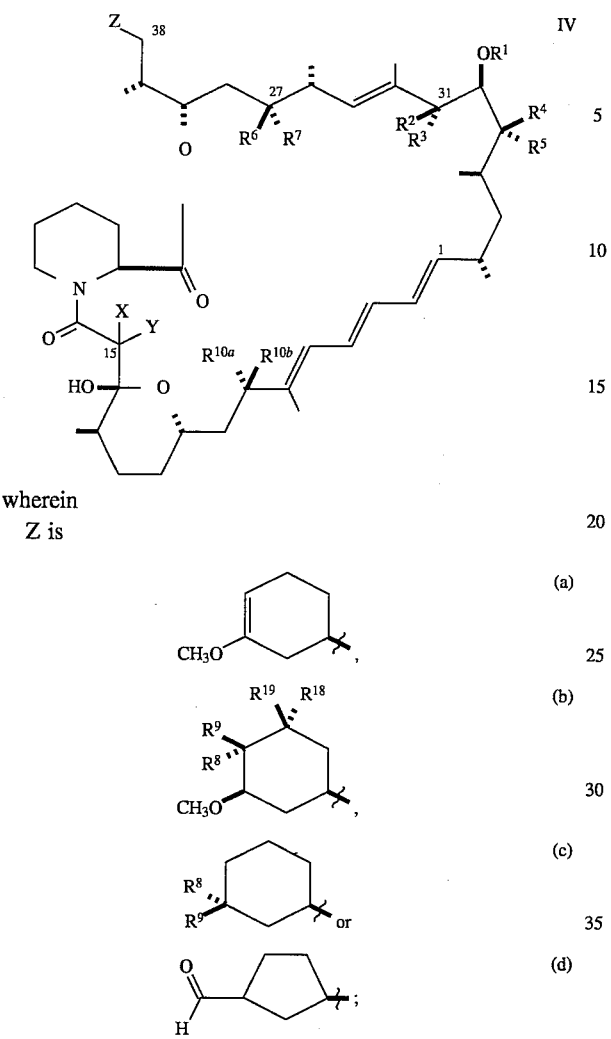

wherein
Z is

R[1] is hydrogen, a hydroxy protecting group, loweralkyl or phenyl-substituted loweralkyl;

R[2] is hydrogen and R[3] is hydroxy or protected hydroxy or R[2] and R[3] taken together are oxo;

R[4] is hydrogen or phenyl-substituted loweralkyl and R[5] is hydroxy or protected hydroxy or R[5] is hydrogen or phenyl-substituted loweralkyl and R[4] is hydroxy or protected hydroxy or R[4] and R[5] taken together are oxo;

R[6] is hydrogen or phenyl-substituted loweralkyl and R[7] is hydrogen, hydroxy or protected hydroxy or R[7] is hydrogen or phenyl-substituted loweralkyl and R[6] is hydroxy or protected hydroxy or R[6] and R[7] taken together are
(1) oxo,
(2) diazo,
(3) =CH$_2$,
(4) —O—(CH$_2$)$_2$—O—,
(5) —S—(CH$_2$)$_2$—S—,
(6) —O—(CH$_2$)$_3$—O—,
(7) —S—(CH$_2$)$_3$—S—,
(8) =N—OR[20] wherein R[20] is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(9) =N—N(R[21])(R[22]) wherein R[21] and R[22] are independently selected from hydrogen, loweralkyl, aryl, arylalkyl, heterocyclic and heterocyclicalkyl;

R[8], R[9], R[18] and R[19] are independently selected from
(1) hydrogen,
(2) —OS(O)$_2$CF$_3$,
(3) —OS(O)$_2$F,
(4) —OS(O)$_2$R[21a] wherein R[21a] is loweralkyl, aryl, arylalkyl, heterocyclic or heterocyclicalkyl,
(5) —OC(O)R[23] wherein R[23] is —O-aryl, —O—(N-succinimidyl), —O-benzotriazolyl, —O-2'-pyridyl or 5-tetrazolyl;
(6) —OC(O)—N(R[24])(R[25]) wherein R[24] and R[25] are independently selected from
  (a) hydrogen,
  (b) loweralkyl,
  (c) alkenyl,
  (d) alkynyl,
  (e) cycloalkyl,
  (f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
    (i) hydroxy,
    (ii) —COOH,
    (iii) —CN,
    (iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—(O)—NH—, —S(O)$_2$NH—, —NHS(O)$_2$—, —N(R[27]—, —C(NR[27])NHNH— and —NHNHC(NR[27])— wherein R[27] is hydrogen, loweralkyl, aryl or heterocyclic,
    (v) cycloalkyl,
    (vi) aryl,
    (vii) heterocyclic,
    (viii) —N(R[28])(R[29]) wherein R[28] and R[29] are independently selected from hydrogen, loweralkyl, hydroxyalkyl, aryl and heterocyclic,
    (ix) guanidino,
    (x) —S(O)$_2$R[11] wherein R[11] is loweralkyl, aryl or arylalkyl,
    (xi) —OS(O)$_2$R[11] wherein R[11] is defined as above,
    (xii) —SO$_3$H,
    (xiii) —S(O)$_2$NH$_2$,
    (xiv) —SR[28] wherein R[28] is defined as above,
    (xv) halogen,
    (xvi) oxo and
    (xvii) epoxy;
  (g) aryl,
  (h) heterocyclic,
  (i) —NHC(O)—O-loweralkyl,
  (j) —NHC(O)—aryl,
  (k) —NHC(O)-heterocyclic and
  (l) loweralkyl substituted by —OC(O)—R[f] wherein R[f] is carboxyalkyl or —N(R[24])(R[25]) taken together form a nitrogen-containing heterocyclic group,
(7) —OR[25] wherein R[25] is as defined above,
(8) a protected hydroxy group,
(9) —OC(O)N(OR[24])(R[25]) wherein R[24] and R[25] are defined as above,

(10) —O(CH$_2$)$_i$C(O)OR$^{20}$ wherein i is one or two and R$^{20}$ is independently defined as above,

(11) —O(CH(Si(CH$_3$)$_3$))—(CH$_2$)$_j$C(O)OR$^{20}$ wherein j is zero or one and R$^{20}$ is independently defined as above,

(12) —O(CH$_2$)$_i$C(O)N(R$^{24}$)(R$^{25}$) wherein i, R$^{24}$ and R$^{25}$ are defined as above,

(13) —O(CH$_2$)$_i$C(O)N(OR$^{24}$)(R$^{25}$) wherein i, R$^{24}$ and R$^{25}$ are defined as above,

(14) —O(CH$_2$)$_i$C(O)N(R$^{24}$)(N(R$^{24}$)(R$^{25}$)) wherein i, R$^{24}$ and R$^{25}$ are defined as above,

(15) —O(CH$_2$)$_i$NHC(O)N(R$^{24}$)(R$^{25}$) wherein i, R$^{24}$ and R$^{25}$ are defined as above,

(16) —O(CH$_2$)$_i$NHC(O)N(OR$^{24}$)(R$^{25}$) wherein i, R$^{24}$ and R$^{25}$ are defined as above,

(17) —O(CH$_2$)$_i$NHC(O)N(R$^{24}$)(N(R$^{24}$)(R$^{25}$)) wherein i, R$^{24}$ and R$^{25}$ are defined as above,

(18) —OS(O)$_2$N(R$^{24}$)(R$^{25}$) wherein R$^{24}$ and R$^{25}$ are defined as above,

(19) —O(CH$_2$)$_i$—NHC(O)R$^{24}$ wherein R$^{24}$ is defined as above,

(20) —OCH(R$^{24}$)—SH wherein R$^{24}$ is defined as above,

(21) —OCH(R$^{24}$) —S-loweralkyl wherein R$^{24}$ is defined as above,

(22) —OCH(R$^{24}$) —S-aryl wherein R$^{24}$ is defined as above,

(23) —N$_3$,

(24) —N=C=O,

(25) —N(R$^{24}$)(R$^{25}$) wherein R$^{24}$ and R$^{25}$ are defined as above,

(26) —NHC(O)—R$^{24}$ wherein R$^{24}$ is defined as above,

(27) —NHC(O)—N(R$^{24}$)(R$^{25}$) wherein R$^{24}$ and R$^{25}$ are defined as above,

(28) —S—R$^{24}$ wherein R$^{24}$ is defined as above and

(29) —S—q—R$^{24}$ wherein q is a divalent radical selected from the group consisting of —S—, —C(O)—, —C(O)—O—, —C(O)—NH— and —C(N(R$^{27}$))—NHNH— and R$^{24}$ and R$^{27}$ are defined as above, with the proviso that one of R$^8$ and R$^9$ is hydrogen and the other is not hydrogen and one of R$^{18}$ and R$^{19}$ is hydrogen and the other is not hydrogen; or R$^8$ and R$^9$ taken together are
(1) oxo,
(2) =N—O—R$^{24}$ wherein R$^{24}$ is defined as above or
(3) =N—N(R$^{24}$)(R$^{25}$) wherein R$^{24}$ and R$^{25}$ are defined as above; or R$^{18}$ and R$^{19}$ taken together are
(1) oxo,
(2) =N—O—R$^{24}$ wherein R$^{24}$ is independently defined as above or
(3) =N—N(R$^{24}$)(R$^{25}$) wherein R$^{24}$ and R$^{25}$ are independently defined as above; or one of R$^8$ and R$^9$ taken together with one of R$^{18}$ and R$^{19}$ form a heterocyclic ring with the others of R$^8$, R$^9$, R$^{18}$ and R$^{19}$ being hydrogen or together forming a bond; or R$^8$ and R$^{18}$ are hydrogen and R$^{8'}$ and R$^{19}$ form a bond; R$^{10a}$ is hydrogen and R$^{10b}$ is hydrogen, hydroxy, protected hydroxy, alkoxy, alkenyl, alkenyloxy, halogen or —SR$^{28}$ wherein R$^{28}$ is independently defined as above or R$^{10}$b is hydrogen and R$^{10}$a is hydrogen, hydroxy, protected hydroxy, alkoxy, alkenyl, alkenyloxy, halogen or —SR$^{28}$ wherein R$^{28}$ is independently defined as above or R$^{10a}$ and R$^{10b}$ are both alkoxy or —SR$^{28a}$ wherein R$^{28a}$ is loweralkyl, aryl or heterocyclic or R$^{10a}$ and R$^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula IV are those wherein:

Z is

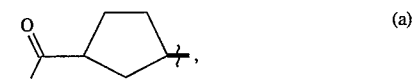

(a)

(b)

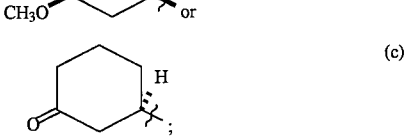

(c)

R$^1$ is methyl;

R$^2$ is hydrogen and R$^3$ is hydroxy;

R$^4$ is hydrogen and R$^5$ is hydroxy or R$^5$ is hydrogen and R$^4$ is hydroxy or R$^4$ and R$^5$ taken together are oxo;

R$^6$ and R$^7$ are defined as above;

R$^{10a}$ is hydrogen, methoxy or fluoro and R$^{10b}$ is hydrogen; and

X and Y taken together are oxo.

More preferred compounds of the formula IV are those wherein:

Z is

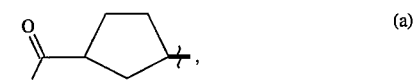

(a)

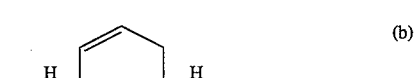

(b)

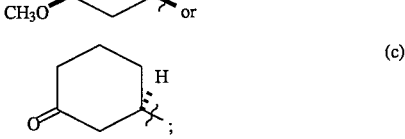

(c)

R$^1$ is methyl;

R$^2$ is hydrogen and R$^3$ is hydroxy;

R$^4$ is hydrogen and R$^5$ is hydroxy or R$^5$ is hydrogen and R$^4$ is hydroxy or R$^4$ and R$^5$ taken together are oxo;

R$^6$ and R$^7$ taken together are
(1) oxo,
(2) =N—OR$^{20}$ wherein R$^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein R$^{21}$ and R$^{22}$ are independently selected from hydrogen, loweralkyl, aryl, arylalkyl, heterocyclic and heterocyclicalkyl;

R$^{10a}$ is hydrogen, methoxy or fluoro and R$^{10b}$ is hydrogen; and and Y taken together are oxo.

Even more preferred compounds of the formula IV are those wherein:

Z is (a) [cyclopentane with CHO group]

(b) [cyclohexene with CH3O and H substituents] or (c) [cyclohexanone with H substituent]

$R^1$ is methyl;

$R^2$ is hydrogen and $R^3$ is hydroxy;

$R^4$ and $R^5$ taken together are oxo;

$R^6$ and $R^7$ taken together are (1) oxo,
(2) =N—$OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N($R^{21}$)($R^{22}$) wherein $R^{21}$ and $R^{22}$ are independently selected from hydrogen, loweralkyl, aryl, arylalkyl, heterocyclic and heterocyclicalkyl;

$R^{10a}$ is methoxy and $R^{10b}$ is hydrogen; and

X and Y taken together are oxo.

Most preferred compounds of the formula IV are those wherein:

Z is (a) [cyclopentane with CHO group]

(b) [cyclohexene with CH3O and H substituents] or (c) [cyclohexanone with H substituent]

$R^1$ is methyl;

$R^2$ is hydrogen and $R^3$ is hydroxy;

$R^4$ and $R^5$ taken together are oxo;

$R^6$ and $R^7$ taken together are oxo;

$R^{10a}$ is methoxy and $R^{10b}$ is hydrogen; and

X and Y taken together are oxo.

In another aspect of the present invention there are compounds of the formula V:

[Structure V]

wherein
$R^1$ is hydrogen, a hydroxy protecting group, loweralkyl or phenyl-substituted loweralkyl;

$R^2$ is hydrogen and $R^3$ is hydroxy or protected hydroxy or $R^2$ and $R^3$ taken together are oxo;

$R^4$ is hydrogen or phenyl-substituted loweralkyl and $R^5$ is hydroxy or protected hydroxy or $R^5$ is hydrogen or phenyl-substituted loweralkyl and $R^4$ is hydroxy or protected hydroxy or $R^4$ and $R_5$ taken together are oxo;

$R^6$ is hydrogen or phenyl-substituted loweralkyl and $R^7$ is hydrogen, hydroxy or protected hydroxy or $R^7$ is hydrogen or phenyl-substituted loweralkyl and $R^6$ is hydroxy or protected hydroxy or $R^6$ and $R^7$ taken together are (1) oxo,
(2) diazo,
(3) =CH$_2$
(4) —O—(CH$_2$)$_2$—O—,
(5) —S—(CH$_2$)$_2$—S—,
(6) —O—(CH$_2$)$_3$—O—,
(7) —S—(CH$_2$)$_3$—S—,
(8) =N—$OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or (9) =N—N($R^{21}$)($R^{22}$) wherein $R^{21}$ and $R^{22}$ are independently selected from hydrogen, loweralkyl, aryl, arylalkyl, heterocyclic and heterocyclicalkyl;

$R^8$ is
  (1) —OC(O)N(O$R^{20}$)($R^{24}$) or
  (2) —O—C(O)—NHN($R^{24}$)($R^{25}$) wherein $R^{20}$ is hydrogen, loweralkyl, alkenyl, cycloalkyl, cycloalkenyl, bicycloalkenyl, aryl or heterocyclic, each of which is optionally substituted with loweralkyl, hydroxy, aryl or heterocyclic and $R^{24}$ and $R^{25}$ are independently selected from
    (a) hydrogen,
    (b) loweralkyl,
    (c) alkenyl,
    (d) alkynyl,
    (e) cycloalkyl,
    (f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
      (i) hydroxy,
      (ii) —COOH,
      (iii) —CN,
      (iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N($R^{27}$)—, —C(N$R^{27}$)NHNH— and —NHNHC(N$R^{27}$)— wherein $R^{27}$ is hydrogen, loweralkyl, aryl or heterocyclic,
      (v) cycloalkyl,
      (vi) aryl,
      (vii) heterocyclic,
      (viii) —N($R^{28}$)($R^{29}$) wherein $R^{28}$ and $R^{29}$ are independently selected from hydrogen, loweralkyl, hydroxyalkyl, aryl and heterocyclic,
      (ix) guanidino,
      (x) —S(O)$_2$$R^{11}$ wherein $R^{11}$ is loweralkyl, aryl or arylalkyl,
      (xi) —OS(O)$_2$$R^{11}$ wherein $R^{11}$ is defined as above,
      (xii) —SO$_3$H,
      (xiii) —S(O)$_2$NH$_2$,
      (xiv) —S$R^{28}$ wherein $R^{28}$ is defined as above,
      (xv) halogen,
      (xvi) oxo and
      (xvii) epoxy;
    (g) aryl,
    (h) heterocyclic,
    (i) —NHC(O)—O-loweralkyl,
    (j) —NHC(O)-aryl,
    (k) —NHC(O)-heterocyclic or
    (l) loweralkyl substituted by —OC(O)—$R^f$ wherein $R^f$ is carboxyalkyl or —N($R^{24}$)($R^{25}$) taken together form a nitrogen-containing heterocyclic group;

$R^9$ is hydrogen;

$R^{10a}$ is hydrogen and $R^{10b}$ is hydrogen, hydroxy, protected hydroxy, alkoxy, alkenyl, alkenyloxy, halogen or —S$R^{28}$ wherein $R^{28}$ is independently defined as above or $R^{10b}$ is hydrogen and $R^{10a}$ is hydrogen, hydroxy, protected hydroxy, alkoxy, alkenyl, alkenyloxy, halogen or —S$R^{28}$ wherein $R^{28}$ is independently defined as above or $R^{10a}$ and $R^{10b}$ are both alkoxy or —S$R^{28a}$ wherein $R^{28a}$ is loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula V are those wherein:

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R^5$ taken together are oxo;

$R^6$ and $R^7$ are defined as above;

$R^8$ is defined as above;

$R^9$ is hydrogen;

$R^{10a}$ is hydrogen, methoxy or fluoro and $R^{10b}$ is hydrogen;

$R^{20}$ is defined as above;

$R^{24}$ is defined as above; and

X and Y taken together are oxo.

More preferred compounds of the formula V are those wherein:

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R_5$ taken together are oxo;

$R^6$ and $R^7$ taken together are
  (1) oxo,
  (2) =N—O$R^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
  (3) =N—N($R^{21}$)($R^{22}$) wherein $R^{21}$ and $R^{22}$ are independently selected from hydrogen, loweralkyl, aryl, arylalkyl, heterocyclic and heterocyclicalkyl;

$R^8$ is —OC(O)N(O$R^{20}$)($R^{24}$) wherein $R^{20}$ and $R^{24}$ are defined as above;

$R^{10a}$ is hydrogen, methoxy or fluoro and $R^{10b}$ is hydrogen; and

X and Y taken together are oxo.

Even more preferred compounds of the formula V are those wherein:

$R^1$ is methyl;

$R^2$ is hydrogen and $R^3$ is hydroxy;

$R^4$ and $R^5$ taken together are oxo;

$R^6$ and $R^7$ taken together are oxo;

$R^8$ is —OC(O)N(O$R^{20}$)($R^{24}$) wherein $R^{20}$ is hydrogen, loweralkyl or arylalkyl and $R^{24}$ is hydrogen, loweralkyl or cycloalkyl;

$R^{10a}$ is methoxy and $R^{10b}$ is hydrogen; and

X and Y taken together are oxo.

Most preferred compounds of the formula V are those wherein:

$R^1$ is methyl;

$R^2$ is hydrogen and $R^3$ is hydroxy;

$R^4$ and $R^5$ taken together are oxo;

$R^6$ and $R^7$ taken together are oxo;

$R^8$ is —OC(O)N(OR$^{20}$)(R$^{24}$) wherein $R^{20}$ is hydrogen, methyl or benzyl and $R^{24}$ is hydrogen or methyl;

$R^{10a}$ is methoxy and $R^{10b}$ is hydrogen; and

X and Y taken together are oxo.

In another aspect of the present invention there are compounds of the formula VI:

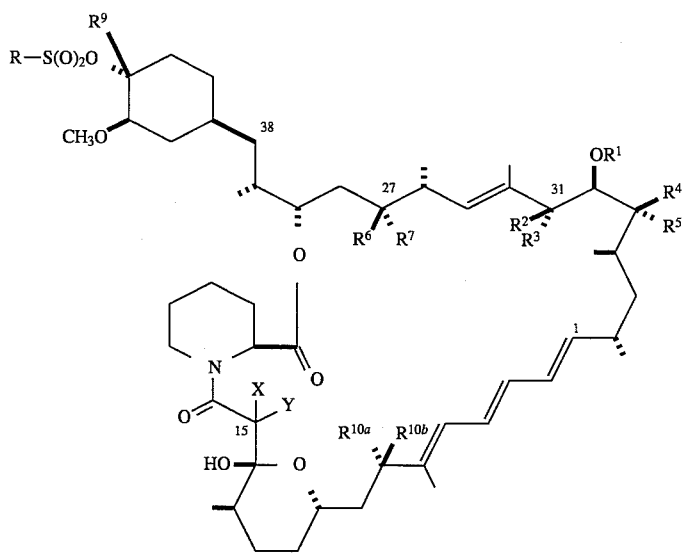

VI wherein

R is F;

$R^1$ is hydrogen, a hydroxy protecting group, loweralkyl or phenyl-substituted loweralkyl;

$R^2$ is hydrogen and $R^3$ is hydroxy or protected hydroxy or $R^2$ and $R^3$ taken together are oxo;

$R^4$ is hydrogen or phenyl-substituted loweralkyl and $R^5$ is hydroxy or protected hydroxy or $R^5$ is hydrogen or phenyl-substituted loweralkyl and $R^4$ is hydroxy or protected hydroxy or $R^4$ and $R^5$ taken together are oxo;

$R^6$ is hydrogen or phenyl-substituted loweralkyl and $R^7$ is hydrogen, hydroxy or protected hydroxy or $R^7$ is hydrogen or phenyl-substituted loweralkyl and $R^6$ is hydroxy or protected hydroxy or $R^6$ and $R^7$ taken together are
(1) oxo,
(2) diazo,
(3) =CH$_2$
(4) —O—(CH$_2$)$_2$—O—,
(5) —S—(CH$_2$)$_2$—S—,
(6) —O—(CH$_2$)$_3$—O—,
(7) —S—(CH$_2$)$_3$—S—,
(8) =N—OR$^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(9) =N—N(R$^{21}$)(R$^{22}$) wherein $R^{21}$ and $R^{22}$ are independently selected from hydrogen, loweralkyl, aryl, arylalkyl, heterocyclic and heterocyclicalkyl;

$R^9$ is hydrogen;

$R^{10a}$ is hydrogen and $R^{10b}$ is hydrogen, hydroxy, protected hydroxy, alkoxy, alkenyl, alkenyloxy, halogen or —SR$^{28}$ wherein $R^{28}$ is independently defined as above or $R^{10b}$ is hydrogen and $R^{10a}$ is hydrogen, hydroxy, protected hydroxy, alkoxy, alkenyl, alkenyloxy, halogen or —SR$^{28}$ wherein $R^{28}$ is independently defined as above or $R^{10a}$ and $R^{10b}$ are both alkoxy or —SR$^{28a}$ wherein $R^{28a}$ is loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula VI are those wherein:

R is F;

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R^5$ taken together are oxo;

$R^6$ and $R^7$ are defined as above;

$R^{10a}$ is hydrogen, methoxy or fluoro and $R^{10b}$ is hydrogen; and

X and Y taken together are oxo.

More preferred compounds of the formula VI are those wherein:

R is F;

$R^1$ is methyl;

$R^2$ is hydrogen and $R^3$ is hydroxy;

$R^4$ is hydrogen and $R^5$ is hydroxy or $R^5$ is hydrogen and $R^4$ is hydroxy or $R^4$ and $R^5$ taken together are oxo;

$R^6$ and $R^7$ taken together are
(1) oxo,
(2) =N—OR$^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein $R^{21}$ and $R^{22}$ are independently selected from hydrogen, loweralkyl, aryl, arylalkyl, heterocyclic and heterocyclicalkyl;

$R^{10a}$ is hydrogen, methoxy or fluoro and $R^{10b}$ is hydrogen; and

27

X and Y taken together are oxo.

Even more preferred compounds of the formula VI are those wherein:

R is F; $R^1$ is methyl;
$R^2$ is hydrogen and $R^3$ is hydroxy;
$R^4$ and $R^5$ taken together are oxo;
$R^6$ and $R^7$ taken together are
  (1) oxo,
  (2) =N—$OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
  (3) =N—$N(R^{21})(R^{22})$ wherein $R^{21}$ and $R^{22}$ are independently selected from hydrogen, loweralkyl, aryl, arylalkyl, heterocyclic and heterocyclicalkyl;
$R^{10a}$ is methoxy and $R^{10b}$ is hydrogen; and
X and Y taken together are oxo.

Most preferred compounds of the formula VI are those wherein:

R is F;
$R^1$ is methyl;
$R^2$ is hydrogen and $R^3$ is hydroxy;
$R^4$ and $R^5$ taken together are oxo;
$R^6$ and $R^7$ taken together are oxo;
$R^{10a}$ is methoxy and $R^{10b}$ is hydrogen; and
X and Y taken together are oxo.

In another aspect of the present invention there are compounds of the formula VII:

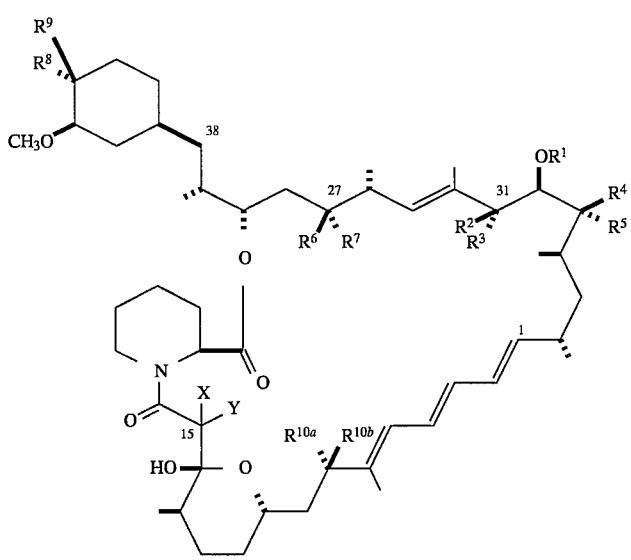

VII wherein
$R^1$ is hydrogen, a hydroxy protecting group, loweralkyl or phenyl-substituted loweralkyl;
$R^2$ is hydrogen and $R^3$ is hydroxy or protected hydroxy or $R^2$ and $R^3$ taken together are oxo;
$R^4$ is hydrogen or phenyl-substituted loweralkyl and $R^5$ is hydroxy or protected hydroxy or $R^5$ is hydrogen or phenyl-substituted loweralkyl and $R^4$ is hydroxy or protected hydroxy or $R^4$ and $R^5$ taken together are oxo;
$R^6$ is hydrogen or phenyl-substituted loweralkyl and $R^7$ is hydrogen, hydroxy or protected hydroxy or $R^7$ is hydrogen or phenyl-substituted loweralkyl and $R^6$ is

28 hydroxy or protected hydroxy or $R^6$ and $R^7$ taken together are
  (1) oxo,
  (2) diazo,
  (3) =$CH_2$
  (4) —O—$(CH_2)_2$—O—,
  (5) —S—$(CH_2)_2$—S—,
  (6) —O—$(CH_2)_3$—O—,
  (7) —S—$(CH_2)_3$—S—,
  (8) =N—$OR^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
  (9) =N—$N(R^{21})(R^{22})$ wherein $R^{21}$ and $R^{22}$ are independently selected from hydrogen, loweralkyl, aryl, arylalkyl, heterocyclic and heterocyclicalkyl;
$R^8$ is
  (1) —$O(CH_2)_iC(O)OR^{20}$ wherein i is one or two and $R^{20}$ is independently defined as above,
  (2) —$O(CH_2)_iC(O)N(R^{24})(R^{25})$ wherein i is one or two and $R^{24}$ and $R^{25}$ are independently selected from
    (a) hydrogen,
    (b) loweralkyl,
    (c) alkenyl,
    (d) alkynyl,
    (e) cycloalkyl,
    (f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
      (i) hydroxy,
      (ii) —COOH,
      (iii) —CN,
      (iv) —Q-loweralkyl, —Q-aryl, —Q-(arylalkyl), —Q-heterocyclic or —Q-(heterocyclicalkyl) wherein Q is —O—, —S—, —S(O)—, —$S(O)_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —$S(O)_2NH$—, —$NHS(O)_2$—, —$N(R^{27})$—, —$C(NR^{27})NHNH$— and —$NHNHC(NR^{27})$— wherein $R^{27}$ is hydrogen, loweralkyl, aryl or heterocyclic,
(v) cycloalkyl,
(vi) aryl,
(vii) heterocyclic,
(viii) —N($R^{28}$)($R^{29}$) wherein $R^{28}$ and $R^{29}$ are independently selected from hydrogen, loweralkyl, hydroxyalkyl, aryl and heterocyclic,
(ix) guanidino,
(x) —S(O)$_2$$R^{11}$ wherein $R^{11}$ is loweralkyl, aryl or arylalkyl,
(xi) —OS(O)$_2$$R^{11}$ wherein $R^{11}$ is defined as above,
(xii) —SO$_3$H,
(xiii) —S(O)$_2$NH$_2$,
(xiv) —S$R^{28}$ wherein $R^{28}$ is defined as above,
(xv) halogen,
(xvi) oxo and
(xvii) epoxy;
(g) aryl,
(h) heterocyclic,
(i) —NHC(O)—O-loweralkyl,
(j) —NHC(O)—aryl,
(k) —NHC(O)-heterocyclic and
(l) loweralkyl substituted by—OC(O)—$R^f$ wherein $R^f$ is carboxyalkyl or —N($R^{24}$)($R^{25}$) taken together form a nitrogen-containing heterocyclic group,
(3) —O(CH$_2$)$_i$C(O)N(O$R^{24}$)($R^{25}$) wherein i, $R^{24}$ and $R^{25}$ are defined as above,
(4) —O(CH$_2$)$_i$C(O)N($R^{24}$)(N($R^{24}$)($R^{25}$)) wherein i, $R^{24}$ and $R^{25}$ are defined as above,
(5) —O(CH$_2$)$_i$NHC(O)N($R^{24}$)($R^{25}$) wherein i, $R^{24}$ and $R^{25}$ are defined as above,
(6) —(CH$_2$)$_i$NHC(O)N(O$R^{24}$)($R^{25}$) wherein i, $R^{24}$ and $R^{25}$ are defined as above or
(7) —(CH$_2$)$_i$NHC(O)N($R^{24}$)(N($R^{24}$)($R^{25}$)) wherein i, $R^{24}$ and $R^{25}$ are defined as above;

$R^9$ is hydrogen;

$R^{10a}$ is hydrogen and $R^{10b}$ is hydrogen, hydroxy, protected hydroxy, alkoxy, alkenyl, alkenyloxy, halogen or —S$R^{28}$ wherein $R^{28}$ is independently defined as above or $R^{10b}$ is hydrogen and $R^{10a}$ is hydrogen, hydroxy, protected hydroxy, alkoxy, alkenyl, alkenyloxy, halogen or —S$R^{28}$ wherein $R^{28}$ is independently defined as above or $R^{10a}$ and $R^{10b}$ are both alkoxy or —S$R^{28a}$ wherein $R^{28a}$ is loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo;

or a pharmaceutically acceptable salt, ester, amide or prodrug thereof.

Preferred compounds of the formula VII are those wherein:

$R^1$ is methyl;
$R^2$ is hydrogen and $R^3$ is hydroxy;
$R^4$ is hydrogen and $R^5$ is hydroxy or $R^5$ is hydrogen and $R^4$ is hydroxy or $R^4$ and
$R^5$ taken together are oxo;
$R^6$ and $R^7$ are defined as above;
$R^8$ is defined as above;
$R^9$ is hydrogen;
$R^{10a}$ is hydrogen, methoxy or fluoro and $R^{10b}$ is hydrogen; and X and Y taken together are oxo.

More preferred compounds of the formula VII are those wherein:

$R^1$ is methyl;
$R^2$ is hydrogen and $R^3$ is hydroxy;
$R^4$ is hydrogen and $R^5$ is hydroxy or $R^5$ is hydrogen and $R^4$ is hydroxy or $R^4$ and
$R^5$ taken together are oxo;
$R^6$ and $R^7$ taken together are
(1) oxo,
(2) =N—O$R^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N($R^{21}$)($R^{22}$) wherein $R^{21}$ and $R^{22}$ are independently selected from hydrogen, loweralkyl, aryl, arylalkyl, heterocyclic and heterocyclicalkyl;

$R^8$ is
(1) —O(CH$_2$)$_i$C(O)N($R^{24}$)($R^{25}$) wherein i is one or two and $R^{24}$ and $R^{25}$ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
(i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)$_2$NH—, —NHS(O)$_2$—, —N($R^{27}$)—, —C(N$R^{27}$)NHNH— and —NHNHC(N$R^{27}$)— wherein $R^{27}$ is hydrogen, loweralkyl, aryl or heterocyclic,
(v) cycloalkyl,
(vi) aryl,
(vii) heterocyclic,
(viii) —N($R^{28}$)($R^{29}$) wherein $R^{28}$ and $R^{29}$ are independently selected from hydrogen, loweralkyl, hydroxyalkyl, aryl and heterocyclic,
(ix) guanidino,
(x) —S(O)$_2$$R^{11}$ wherein $R^{11}$ is loweralkyl, aryl or arylalkyl,
(xi) —OS(O)$_2$$R^{11}$ wherein $R^{11}$ is defined as above,
(xii) —SO$_3$H,
(xiii) —S(O)$_2$NH$_2$,
(xiv) —S$R^{28}$ wherein $R^{28}$ is defined as above,
(xv) halogen,
(xvi) oxo and
(xvii) epoxy;
(g) aryl,
(h) heterocyclic, (i) —NHC(O)—O-loweralkyl,
(j) —NHC(O)aryl,
(k) —NHC(O)-heterocyclic and
(l) loweralkyl substituted by —OC(O)—$R^f$ wherein $R^f$ is carboxyalkyl or —N($R^{24}$)($R^{25}$) taken together form a nitrogen-containing heterocyclic group or
(2) —O(CH$_2$)$_i$C(O)N(OR$^{24}$)(R$^{25}$) wherein i, $R^{24}$ and $R^{25}$ are defined as above, $R^9$ is hydrogen;

$R^{10a}$ is hydrogen, methoxy or fluoro and $R^{10b}$ is hydrogen; and

X and Y taken together are oxo.

Even more preferred compounds of the formula VII are those wherein:

$R^1$ is methyl;

$R^2$ is hydrogen and $R^3$ is hydroxy;

$R^4$ and $R^5$ taken together are oxo;

$R^6$ and $R^7$ taken together are
(1) oxo,
(2) =N—OR$^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein $R^{21}$ and $R^{22}$ are independently selected from hydrogen, loweralkyl, aryl, arylalkyl, heterocyclic and heterocyclicalkyl;

$R^8$ is —O(CH$_2$)$_i$C(O)N(R$^{24}$)(R$^{25}$) wherein i is one or two and $R^{24}$ and $R^{25}$ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
(i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—(O)—NH—, —S(O)$_2$NH—, —NHS(O)$_2$—, —N(R$^{27}$)—, —C(NR$^{27}$)NHNH— and —NHNHC(NR$^{27}$)— wherein $R^{27}$ is hydrogen, loweralkyl, aryl or heterocyclic,
(v) cycloalkyl,
(vi) aryl,
(vii) heterocyclic,
(viii) —N(R$^{28}$)(R$^{29}$) wherein $R^{28}$ and $R^{29}$ are independently selected from hydrogen, loweralkyl, hydroxyalkyl, aryl and heterocyclic,
(ix) guanidino,
(x) —S(O)$_2$R$^{11}$ wherein $R^{11}$ is loweralkyl, aryl or arylalkyl,
(xi) —OS(O)$_2$R$^{11}$ wherein $R^{11}$ is defined as above,
(xii) —SO$_3$H,
(xiii) —S(O)$_2$NH$_2$,
(xiv) —SR$^{28}$ wherein $R^{28}$ is defined as above,
(xv) halogen,
(xvi) oxo and
(xvii) epoxy;
(g) aryl,
(h) heterocyclic,
(i) —NHC(O)—O-loweralkyl,
(j) —NHC(O)-aryl,
(k) —NHC(O)-heterocyclic and
(l) loweralkyl substituted by —OC(O)—$R^f$ wherein $R^f$ is carboxyalkyl or —N($R^{24}$)($R^{25}$) taken together form a nitrogen-containing heterocyclic group, $R^9$ is hydrogen;

$R^{10a}$ is methoxy and $R^{10b}$ is hydrogen; and

X and Y taken together are oxo.

Even more preferred compounds of the formula VII are those wherein:

$R^1$ is methyl;

$R^2$ is hydrogen and $R^3$ is hydroxy;

$R^4$ and $R^5$ taken together are oxo;

$R^6$ and $R^7$ taken together are
(1) oxo,
(2) =N—OR$^{20}$ wherein $R^{20}$ is hydrogen, loweralkyl, alkenyl, cycloalkyl, cycloalkenyl, bicycloalkenyl, aryl, arylalkyl, heterocyclic or heterocyclicalkyl, each of which is optionally substituted with loweralkyl, halogen, hydroxy, aryl or heterocyclic; or
(3) =N—N(R$^{21}$)(R$^{22}$) wherein $R^{21}$ and $R^{22}$ are independently selected from hydrogen, loweralkyl; aryl, arylalkyl, heterocyclic and heterocyclicalkyl;

$R^8$ is —O(CH$_2$)$_i$C(O)N(OR$^{24}$)(R$^{25}$) wherein i is one or two and $R^{24}$ and $R^{25}$ are independently selected from
(a) hydrogen,
(b) loweralkyl,
(c) alkenyl,
(d) alkynyl,
(e) cycloalkyl,
(f) substituted loweralkyl, substituted alkenyl, substituted alkynyl or substituted cycloalkyl wherein the loweralkyl group, the alkenyl group, the alkynyl group or the cycloalkyl group is substituted by one or two substituents independently selected from
(i) hydroxy,
(ii) —COOH,
(iii) —CN,
(iv) —Q-loweralkyl, —Q-aryl, —Q-(arylalkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein $R^{27}$ is hydrogen, loweralkyl, aryl or heterocyclic,
(v) cycloalkyl,
(vi) aryl,
(vii) heterocyclic,
(viii) —N(R$^{28}$)(R$^{29}$) wherein $R^{28}$ and $R^{29}$ are independently selected from hydrogen, loweralkyl, hydroxyalkyl, aryl and heterocyclic, (ix) guanidino,
(x) —S(O)$_2$R$^{11}$ wherein R$^{11}$ is loweralkyl, aryl or arylalkyl,
(xi) —OS(O)$_2$R$^{11}$ wherein R$^{11}$ is defined as above,
(xii) —SO$_3$H,
(xiii) —S(O)$_2$NH$_2$,
(xiv) —SR$^{28}$ wherein R$^{28}$ is defined as above,
(xv) halogen,
(xvi) oxo and
(xvii) epoxy;
(g) aryl,
(h) heterocyclic,
(i) —NHC(O)—O-loweralkyl,
(j) —NHC(O)-aryl,
(k) —NHC(O)-heterocyclic and
(l) loweralkyl substituted by —OC(O)—R$^f$ wherein R$^f$ is carboxyalkyl or —N(R$^{24}$)(R$^{25}$) taken together form a nitrogen-containing heterocyclic group, R$^9$ is hydrogen;

R$^{10a}$ is methoxy and R$^{10b}$ is hydrogen; and

X and Y taken together are oxo.

Most preferred compounds of the formula VII are those wherein:

R$^1$ is methyl;

R$^2$ is hydrogen and R$^3$ is hydroxy;

R$^4$ and R$^5$ taken together are oxo;

R$^6$ and R$^7$ taken together are oxo;

R$^8$ is —O(CH$_2$)$_i$C(O)N(OR$^{24}$)(R$^{25}$) wherein i is one or two and R$^{24}$ is hydrogen, loweralkyl or arylalkyl and R$^{25}$ is hydrogen, loweralkyl or cycloalkyl;

R$^9$ is hydrogen;

R$^{10a}$ is methoxy and R$^{10b}$ is hydrogen; and

X and Y taken together are oxo.

When examined for immunomodulatory activity using a common in vitro biological assay, the compounds of the invention are seen to be potent immunosuppressive agents. The compounds of this invention possess immunosuppressive, antimicrobial, antifungal, antiviral, antiinflammatory and antiproliferative activity. Moreover, the compounds of the invention possess the ability to reverse chemotherapeutic drug resistance. As agents which block T-cell activation, a prerequisite for HIV proliferation, the compounds are useful as prophylactics for the prevention of HIV replication. While, the compounds of the invention are useful when used independently of other agents, combination therapy with other immunosuppressants is beneficial as well. These other immunosuppressant agents include but are not limited to FK-506, rapamycin, cyclosporin A, mycophenolic acid, azathioprine, prednisolone, cyclophosphamide, brequinar and leflunomide.

Accordingly, in another aspect of the present invention are disclosed pharmaceutical compositions comprising a compound of the present invention in combination with a pharmaceutically acceptable carrier. Suitable carriers and methods of formulation are also disclosed.

In a further aspect of the present invention are disclosed processes for the preparation of the above compounds, synthetic intermediates useful in the preparations of these and other immunomodulatory derivatives of rapamycin.

In yet another aspect of the present invention is disclosed a method of immunomodulatory treatment in a human or lower mammal, comprising administering to the patient a therapeutically effective amount of at least one compound of this invention.

Throughout this specification and in the appended claims, the following terms have the meanings specified:

The term "alkanoylamino" as used herein refers to —NHC(O)R$^{108}$ wherein R$^{108}$ is a loweralkyl group.

The term "alkenyl" as used herein refers to a straight or branched chain radical of 2 to 10 carbon atoms containing at least one carbon-carbon double bond including, but not limited to, ethenyl, 1-propenyl, 2-propenyl, 2-methyl-1-propenyl, 1-butenyl, 2-butenyl and the like.

The term "alkenyloxy" as used herein refers to —OR$^{100}$ wherein R$^{100}$ is an alkenyl group, including but not limited to, 2-propenyl-oxy and the like.

The term "alkoxy" as used herein refers to —OR$^{101}$ wherein R$^{101}$ is a loweralkyl group including, but not limited to, methoxy, ethoxy, isopropoxy, n-butoxy, sec-butoxy, tert-butoxy and the like.

The term "alkoxyalkoxy" as used herein refers to —OR$^{102}$OR$^{103}$ wherein R$^{103}$ is a loweralkyl group and R$^{102}$ is an alkylene group including, but not limited to, methoxymethoxy, ethoxymethoxy and the like.

The term "alkoxyalkyl" as used herein refers to an alkyl radical to which is appended an alkoxy group.

The term "alkoxycarbonyl" as used herein refers to —(O)OR$^{104}$ wherein R$^{104}$ is a loweralkyl group including, but not limited to, methoxycarbonyl, ethoxycarbonyl and the like.

The term "alkoxycarbonylalkenyl" as used herein refers to an alkenyl radical to which is appended an alkoxycarbonyl group.

The term "alkoxycarbonylthioalkoxy" as used herein refers to —S—R$^{105}$-R$^{106}$ wherein R$^{105}$ is an alkylene group and R$^{106}$ is an alkoxycarbonyl group.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-propylene, and the like.

The term "alkylamino" as used herein refers to —NHR$^{107}$ wherein R$^{107}$ is a loweralkyl group.

The term "alkylsulfonylamino" as used herein refers to —NHS(O)$_2$R$^{110}$ wherein R$^{110}$ is a loweralkyl group.

The term "alkynyl" as used herein refers to a straight or branched chain radical of 2 to 10 carbon atoms containing at least one carbon-carbon triple bond including, but not limited to, ethynyl, 1-propynyl, 2-propynyl, 1-butynyl, 2-butynyl and the like.

The term "aminocarbonyl" as used herein refers to —(O)NH$_2$.

The term "aminocarbonylalkoxy" as used herein refers to —O—R$^{109}$—(O)NH$_2$ wherein R$^{109}$ is an alkylene group.

The term "aryl" as used herein refers to a mono-, bi- or tricyclic carbocyclic ring system having one or two aromatic rings including, but not limited to, phenyl, naphthyl, tetrahydronaphthyl, indanyl, indenyl, fluorenyl and the like. Aryl groups can be unsubstituted or substituted with one, two or three substituents independently selected from loweralkyl, halo, haloalkyl, haloalkoxy, alkenyloxy, alkoxy, alkoxyalkoxy, alkoxycarbonyl, alkoxycarbonylalkenyl, (alkoxycarbonyl)thioalkoxy, thioalkoxy, amino, alkylamino, dialkylamino, aminocarbonyl, aminocarbonylalkoxy, alkanoylamino, arylalkoxy, aryloxy, mercapto, nitro, carboxaldehyde, carboxy, carboxyalkenyl, carboxyalkoxy., alkylsulfonylamino, cyanoalkoxy, (heterocyclic)alkoxy, hydroxy, hydroxyalkoxy, phenyl, phenyl-substituted alkenyl, phenyl-substituted alkynyl, heterocyclic, —S(O)$_2$NH$_2$ and tetrazolylalkoxy. In addition, substituted aryl groups include tetrafluorophenyl and pentafluorophenyl.

The term "arylalkoxy" as used herein refers to —OR¹¹³ wherein R¹¹³ is an arylalkyl group.

The term "arylalkyl" as used herein refers to an alkyl radical to which is appended an aryl group. Examples of arylalkyl include benzyl, 2-phenethyl and the like.

The term "aryloxy" as used herein refers to —OR¹¹⁴ wherein R¹¹⁴ is an aryl group.

The term "bicycloalkenyl" as used herein refers to a bicyclic carbocycle radical containing at least one double bond. Examples of bicycloalkenyl include 1,2-dihydronaphth-4-yl, 1,2,3,4-tetrahydronaphth-1-yl, and the like.

The term "carboxyalkenyl" as used herein refers to an alkenyl radical to which is appended a carboxy group.

The term "carboxyalkoxy" as used herein refers to —OR¹¹¹ wherein R¹¹¹ is a carboxyalkyl group.

The term "carboxyalkyl" as used herein refers to an alkyl radical to which is appended a carboxy (—(O)OH) group. Examples of carboxyalkyl include carboxymethyl, 2-carboxyethyl and the like.

The term "cyanoalkoxy" as used herein refers to —O—R¹¹²—CN wherein R¹¹² is a alkylene group. The term "cycloalkenyl" as used herein refers to a cycloalkyl group containing at least one double bond. Examples of cycloalkenyl include 1-cyclohexenyl, cyclohex-1-en-3-yl and the like.

The term "cycloalkyl" as used herein refers to a cyclic radical of 3 to 10 carbons including, but not limited to, cyclopropyl, cyclobutyl, cyclopentyl, cyclohexyl and the like.

The term "cycloalkylalkyl" as used herein refers to an alkyl radical to which is appended a cycloalkyl group. Examples of cycloalkylalkyl include cyclopropylmethyl, cyclobutylmethyl, cyclopentylmethyl and the like.

The term "dialkylamino" as used herein refers to —NR¹¹⁵R¹¹⁶ wherein R¹¹⁵ and R¹¹⁶ are independently selected from loweralkyl.

The term "diazo" as used herein refers to —N=N—.

The term "epoxy" as used herein refers to

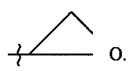

The term "guanidino" as used herein refers to

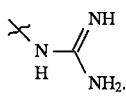

The term "halogen" or "halo" as used herein refers to —Cl, —Br, —F or —I.

The term "haloalkoxy" as used herein refers to —OR¹¹⁷ wherein R¹¹⁷ is a haloalkyl group.

The term "haloalkyl" as used herein refers to a loweralkyl radical bearing at least one halogen substituent, for example, chloromethyl, fluoroethyl or trifluoromethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl, dihydrobenzofuryl or benzothienyl and the like). Heterocyclics include: azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

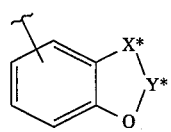

where X* is —CH₂— or —O— and Y* is —(O)— or [—C(R")₂—]ᵥ where R" is C₁-C₄-alkyl and v is 1, 2 or 3 such as 1,3-benzodioxolyl, 1,4-benzodioxanyl and the like.

Heterocyclics also include bicyclic spirocyclic heterocycles such as the ethylene ketal of pyridin-2-on-1-yl, the ethylene ketal of pyridin-4-on-1-yl and the like.

Heterocyclics also include hexose monosaccharides (for example, D-allose, D-altrose, D-glucose, D-mannose, D-gulose, D-idose, D-galactose, D-talose and the like) and pentose monosaccharides (for example, D-ribose, D-arabinose, D-xylose, D-lyxose and the like).

Heterocyclics can be unsubstituted or monosubstituted or disubstituted with substituents independently selected from hydroxy, halo, oxo (=O), amino, alkylamino, dialkylamino, alkoxy, alkoxyalkoxy, alkoxyalkyl, haloalkyl, hydroxy, hydroxyalkyl, cycloalkyl, aryl, arylalkyl, —COOH, —SO₃H, —C(O)NH₂ and loweralkyl. In addition, nitrogen containing heterocycles can be N-protected.

The term "(heterocyclic)alkyl" as used herein refers to a heterocyclic group as defined above appended to a loweralkyl radical as defined above.

The term "heterocyclicalkoxy" as used herein refers to —OR¹¹⁸ wherein R¹¹⁸ is a heterocyclicalkyl group.

The term "hydroxyalkyl" as used herein refers to an alkyl radical to which is appended an hydroxy group. Examples of hydroxyalkyl include hydroxymethyl, 2-hydroxyethyl, 2-hydroxypropyl and the like.

The term "hydroxyalkoxy" as used herein refers to —O—R¹¹⁹—OH wherein R¹¹⁹ is an alkylene group.

The term "hydroxy protecting group" as used herein refers to those radicals which are known in the art of organic synthesis to protect a hydroxyl group against undesirable reaction during synthetic procedures and to be selectively removable such as those hydroxy protecting groups disclosed in T. W. Greene and P. G. M. Wuts, Protective Groups in Organic Synthesis, 2nd ed., John Wiley & Son, Inc., 1991, which is hereby incorporated herein by reference. Examples include, but are not limited to, substituted methyl ethers, for example, methoxymethyl, methylthiomethyl, 2-methoxyethoxymethyl, benzyloxymethyl, 2-(trimethylsilyl)ethoxymethyl, t-butyl, benzyl and triphenylmethyl; tetrahydropyranyl ethers; substituted ethyl ethers, for example, 2,2,2-trichoroethyl; silyl ethers, for example, dimethylthexylsilyl, trisubstituted silyl such as tris(loweralkyl)silyl (e.g., trimethylsilyl, triethylsilyl, tributylsilyl, triisopropylsilyl, tert-butyldimethylsilyl, tri-tert-butylsilyl, triphenylsilyl, triphenylmethyldimethylsilyl, etc.), loweralkyldiarylsilyl (e.g., methyldiphenylsilyl, ethyldiphenylsilyl, propyldiphenylsilyl, tert-butyldiphenylsilyl, etc.), triarylsilyl (e.g., triphenylsilyl, trixylylsilyl, etc.) and triarylalkylsilyl (e.g., tribenzylsilyl, etc.); —C(O)H; —C(O)-loweralkyl (for example, acetyl, propionyl, pivaloyl, t-butylacetyl and the like); —C(O)-aryl (for example, benzoyl and the like); alkoxycarbonyl (for example, ethoxycarbonyl and the like); —S(O)$_2$—(loweralkyl); —S(O)$_2$—(aryl); and the like.

The term "loweralkyl" as used herein refers to a monovalent straight chain or branched chain radical of 1 to 10 carbon atoms including, but not limited to, methyl, ethyl, n-propyl, isopropyl, n-butyl, sec-butyl, isobutyl, tert-butyl, decyl and the like.

The term "oxo" as used herein refers to (=O).

The term "tetrazolylalkoxy" as used herein refers to —O—R$^{120}$-tetrazolyl wherein R$^{120}$ is an alkylene group.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge et al., "Pharmaceutical Salts," *J. Pharm. Sci.*, 66:1–19 (1977) which is incorporated herein by reference.)

Examples of pharmaceutically acceptable, non-toxic esters of the compounds of this invention include C$_1$–C$_6$ alkyl esters wherein the alkyl group is a straight or branched chain. Acceptable esters also include C$_5$–C$_7$ cycloalkyl esters as well as arylalkyl esters such as, but not limited to, benzyl. C$_1$–C$_4$ alkyl esters are preferred. Esters of the compounds of the present invention may be prepared according to conventional methods.

Examples of pharmaceutically acceptable, non-toxic amides of the compounds of this invention include amides derived from ammonia, primary C$_1$–C$_6$ alkyl amines and secondary C$_1$–C$_6$ dialkyl amines wherein the alkyl groups are straight or branched chain. In the case of secondary amines the amine may also be in the form of a 5 or 6 membered heterocycle containing one secondary nitrogen atom. Amides derived from ammonia, C$_1$–C$_3$ alkyl primary amides and di(C1–C2 alkyl) secondary amides are preferred.

Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Cbz), o-chlorobenzyloxycarbonyl ((2-Cl)Cbz)), p-nitrobenzyloxycarbonyl (Cbz(NO$_2$)), p-methoxybenzyloxycarbonyl(Cbz(OMe)), t-amyloxycarbonyl (Aoc), isobornealoxycarbonyl, adamantyloxycarbonyl (Adoc), 2-(4-biphenyl)-2-proploxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

Examples of protecting groups for carboxyl groups include, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine add the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethyl-benzenesulfonyl (Mts) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

The term "protected hydroxy" as used herein refers to the oxygen atom of a hydroxy radical to which has been appended a "hydroxy protecting group" as defined above.

The compounds of the invention may be prepared using one or more of the processes which follow. The starting materials for use in these processes are preferably one of the macrolides isolated from culture media obtained in accordance with known methods by fermentation of *Streptomyces*

*hydroscopicus*, which are disclosed in U.S. Pat. Nos. 3,929, 992 and 3,993,749; *Journal of Antibiotics* 1975, 28 (10), 721–726, 727–732 and *Journal of Antibiotics* 1978, 31 (6), 539–545. One or more of the processes discussed below may be then employed to produce the desired compound of the invention.

Such processes comprise:

(a) producing by selective activation a compound of formula I or VI comprising reacting a corresponding precursor in which one of $R^8$ and $R^9$ is hydrogen and the other is hydroxy with an appropriate amount of fluorosulfonyl anhydride under conditions suitable for the production of the desired product;

(b) producing by selective activation a compound of formula I or VI comprising reacting a corresponding precursor in which one of $R^8$ and $R^9$ is hydrogen and the other is hydroxy with an appropriate amount of trifluoromethanesulfonyl anhydride under conditions suitable for the production of the desired product;

(c) producing a compound of formula I in wherein $R^8$ is hydrogen and $R^9$ is —OC(=O)—O-aryl, —OC(=O)—O—(N-succinimidyl), —OC(=O)-triazole, —OC(=O)-imidazolyl, or —OC(=O)—O-benzotriazolyl by reacting a corresponding precursor in which $R^8$ is hydrogen and $R^9$ is hydroxy with appropriate chloroformates or activated carbonyl compounds;

(d) producing a compound of formula I wherein $R^8$ is hydrogen and and $R^9$ is —OC(=O)—$NR^{24}R^{25}$ by reacting a corresponding precursor in which $R^8$ is hydrogen and $R^9$ is —OC(=O)—O-aryl, —OC(=O)—O—(N-succinimidyl), —OC(=O)—triazolyl, —OC(=O)-imidazolyl, or —OC(=O)—(hydroxybenzotriazolyl) with appropriate amines ($HNR^{24}R^{25}$);

(e) producing a compound of formula I in which $R^8$ is hydrogen and $R^9$ is hydroxy by reacting a corresponding precursor in which $R^9$ is hydrogen and $R^8$ is —$OS(O)_2F$ or —O—$S(O)_2CF_3$ with water in an appropriate solvent;

(f) producing a compound of formula I in which $R^8$ is hydrogen and $R^9$ is —O-formyl by reacting a corresponding precursor in which $R^9$ is hydrogen and $R^8$ is —$OS(O)_2F$ or —$OS(O)_2CF_3$ with N,N-dimethylformamide and water;

(g) producing a compound of formula II or III in which $R^8$ is hydrogen and $R^9$ is —$SR^{24}$ or —$NR^{24}R^{25}$ by reacting a corresponding precursor in which $R^9$ is hydrogen and $R^8$ is —$OS(O)_2F$ or —$OS(O)_2CF_3$ with H—$SR^{24}$, $H_2NC(S)NH_2$, or H—$NR^{24}R^{25}$;

(h) producing a compound of formula I or VII in which one of $R^8$ and $R^9$ is hydrogen and the other is —$OCH_2C(O)OR^{20}$, where $R^{20}$ is as defined above, by etherification of the corresponding hydroxy compound;

(i) producing a compound of formula I or VII in which one of $R^8$ and $R^9$ is hydrogen and the other is —$OCH_2C(O)NR^{24}R^{25}$, where $NR^{24}R^{25}$ is as defined above, by etherification of the corresponding hydroxy compound;

(j) producing a compound of formula I or VII in which one of $R^8$ and $R^9$ is hydrogen and the other is —$OCH_2C(O)N(OR^{24})R^{25}$, where $R^{24}$ and $R^{25}$ are as defined above, by etherification of the corresponding hydroxy compound;

(k) producing a compound of formula I or VII in which one of $R^8$ and $R^9$ is hydrogen and the other is —$OCH_2C(O)NR^{24}NR^{24}R^{25}$, where $R^{24}$ and $R^{25}$ are as defined above, by etherification of the corresponding hydroxy compound;

(l) producing a compound of formula I or VII in which one of $R^8$ and $R^9$ is hydrogen and the other is —$OCH_2$—$NHC(O)R^{24}$, where $R^{24}$ is as defined above, by etherification of the corresponding hydroxy compound;

(m) producing a compound of formula I or VII in which one of $R^8$ and $R^9$ is hydrogen and the other is —$OCH_2$—$NHC(O)NR^{24}R^{25}$, wherein —$NR^{24}R^{25}$ is as defined above, by etherification of the corresponding hydroxy compound;

(n) producing a compound of formula I or VII in which one of $R^8$ and $R^9$ is hydrogen and the other is —$OCH_2$—$NHC(O)N(OR^{24})(R^{25})$, wherein —$NR^{24}R^{25}$ is as defined above, by etherification of the corresponding hydroxy compound;

(o) producing a compound of formula I or VII in which one of $R^8$ and $R^9$ is hydrogen and the other is —$OCH_2$—$NHC(O)NR^{24}NR^{24}R^{25}$, wherein —$NR^{24}R^{25}$ is as defined above, by etherification of the corresponding hydroxy compound;

(p) producing a compound of formula I or VII in which one of $R^8$ and $R^9$ is —$OCH_2$—$NHC(O)R^{24}$ and the other is hydrogen by (i) activating a corresponding —$OCH_2C(O)OH$ functionality, (ii) generating therefrom, directly or in a subsequent synthetic step, a —$OCH_2C(O)N_3$ functionality, (iii) performing a Curtius rearrangement, (iv) trapping with a carboxylic acid having the formula $R^{24}CO_2H$, and (v) heating to generate the desired —$OCH_2$—$NHC(O)R^{24}$ moiety; and (q) producing a compound of formula I or VII in which one of $R^8$ and $R^9$ is hydrogen and the other is —$OCH_2$—$NHC(O)NR^{24}R^{25}$, wherein —$NR^{24}R^{25}$ is as defined above, by formation of a —$OCH_2$—N=C=O isocyanate group followed by addition of an amine $HNR^{14}R^{15}$;

(r) producing a compound of formula I or VII in which one of $R^8$ and $R^9$ is hydrogen and the other is —$OCH_2C(O)NR^{24}R^{25}$, where $R^{24}$ and $R^{25}$ are as defined above, by condensation of $NHR^{24}R^{25}$ with a —$OCH_2C(O)OR^{20}$ group in a corresponding compound;

(s) producing a compound of formula I or VII in which one of $R^8$ and $R^9$ is hydrogen and the other is —$OCH_2C(O)N(OR^{24})R^{25}$, where $R^{24}$ and $R^{25}$ are as defined above, by condensation of $NH(OR^{24})R^{25}$ with a —$OCH_2C(O)OR^{20}$ group in a corresponding compound;

(t) producing a compound of formula I or VII in which one of $R^8$ and $R^9$ is hydrogen and the other is —$OCH_2C(O)NR^{24}NR^{24}R^{25}$, where $R^{24}$ and $R^{25}$ are as defined above, by condensation of $NHR^{24}NR^{24}R^{25}$ with a —$OCH_2C(O)OR^{20}$ group in a corresponding compound;

(u) producing a compound of formula I or VII in which one of $R^8$ and $R^9$ is hydrogen and the other is —$OCH_2$—$NHC(O)N(OR^{24})R^{25}$, wherein $R^{24}$ and $R^{25}$ are as defined above, by formation of a —$OCH_2$—N=C=O isocyanate group followed by addition of $HN(OR^{24})R^{25}$;

(v) producing a compound of formula I or VII in which one of $R^8$ and $R^9$ is hydrogen and the other is —$OCH_2$—$NHC(O)NR^{24}NR^{24}R^{25}$, wherein —NR²⁴R²⁵ and R²⁴ are as defined above, by formation of a —OCH₂—N=C=O isocyanate group followed by addition of HNR²⁴NR²⁴R²⁵;

(w) producing a compound of formula I, wherein $R^9$ is —N₃, by displacement of an —OS(O)₂F or —OS(O)₂CF₃ group in a corresponding compound;

(x) producing a compound of formula III, wherein $R^9$ is —NH₂, by reduction of the —N₃ group in a corresponding compound;

(y) producing a compound of formula III, wherein $R^9$ is —NHCOR*, by acylation of the corresponding amine;

(z) producing a compound of formula III, wherein $R^9$ is —NHC(O)NR$^a$R$^b$, by acylation of the corresponding amine;

(aa) producing a compound of formula III, wherein $R^9$ is a —NH—SO₂R* group, by selective sulfonylation of the corresponding amine;

(bb) producing a compound of formula III, wherein $R^9$ is —NH—C(=O)OR group, by acylation of the corresponding amine;

(cc) producing a compound of formula II, wherein $R^9$ is —NH—SR*, by sulfenylation of the corresponding amine;

(dd) producing a compound of formula III, wherein $R^9$ is —N=C=O, by isocynate formation from the corresponding amine;

(ee) producing a compound of formula III, wherein $R^9$ is —Se-Ph, by displacement of a corresponding —OS(O)₂F or —OS(O)₂CF₃ group;

(ff) producing a compound of formula II, wherein $R^9$ is —Se(O)-Ph, by oxidation of a corresponding —SePh group;

(gg) producing a compound of formula IV, where one of $R^8$ and $R^9$ with one of $R^{18}$ and $R^{19}$ taken together form a bond, the others of $R^8$, $R^9$, $R^{18}$ and $R^{19}$ are hydrogen, by selective 1,2-elimination of an H-OSePh group in a corresponding compound containing an —Se(O)Ph group;

(hh) producing a compound of formula IV, where one of $R^8$ and $R^9$ is OH and one of $R^{18}$ and $R^{19}$ is OH, and the others of $R^8$, $R^9$, $R^{18}$ and $R^{19}$ are hydrogen by selective 1,2-dihydroxylation of an olefin of a corresponding compound;

(ii) producing a compound of formula IV, where $R^8$ or $R^9$ and $R^{18}$ or $R^{19}$ taken together form a —OC(=O)O—, —OS(=O)O—, —OS(O)₂—, —O(CH₂)O— or —CO(CH₂)$_m$CO—, where m=0 to 6, and the others of $R^8$, $R^9$, $R^{18}$ and $R^{19}$ are hydrogen by selective functionalization of a 1,2-dihydroxy group of a corresponding compound;

(jj) producing a compound of formula I-VII, where $R^{10a}$=$R^{10b}$=H from a corresponding compound;

(kk) producing a compound of formula I-VII, where $R^{10a}$=H, $R^{10b}$=OCH₃, or $R^{10a}$=allyl, $R^{10b}$=H from a corresponding compound;

(ll) producing a compound of formula IVc where $R^8$ and $R^9$ taken together are oxo, by reacting a compound of formula I wherein $R^8$ is hydrogen and $R^9$ is —OH or $R^8$ is OH and $R^9$ is hydrogen with fluorosulfonyl anhydride or trifluoromethylsulfonyl anhydride, followed by reaction of the resulting sulfonate with silica gel or an appropriate base to produce the enol ether, followed by hydrolysis of the enol ether; or (mm) producing a compound of formula IVd by rearrangement of a compound of formula I where $R^8$ is —OSO₂F or —OSO₂CF₃ and $R^9$ is hydrogen, in the presence of silica gel or appropriate mild acid under conditions suitable for the production of the desired product and hydrolysis of the enol ether.

In process (a), a suitable reagent for activation of an alcohol is fluorosulfonyl anhydride (prepared according to the procedure described by S. Kongpricha, W. G. Preusse and R. Schwarer, in Inorganic Synthesis, 1968, 11, pp. 151–155). The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from –100° to 30° C., and more preferably from –78° to 0° C. The reaction may require 20 minutes to 24 hours to complete, depending on the reagent chosen.

In process (b), a suitable reagent for activation of an alcohol is trifluoromethanesulfonyl anhydride (Aldrich). The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from –100° to 30° C., and more preferably from –78° to 0° C. The reaction may require 20 minutes to 24 hours to complete, depending on the reagent chosen.

In process (c), a suitable reagent for the formation of an activated alcohol derivative is an aryl chlorofomate, heterocyclic chloroformate, 1,1'-carbonyldiimidazole, di-(N-succinimidyl)carbonate, or carbonyldi(hydroxybenzotriazole). The activation may be carried out in a solvent which does not adversely affect the reaction (e.g. diethyl ether, dichloromethane, tetrahydrofuran, chloroform or N-methylpyrrolidone, pyridine or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferable from 0° C. to 100° C. The reaction may require 20 minutes to 24 hours to complete, depending on the reagent chosen.

In process (d), a suitable reagent for the formation of a carbamate is any suitable amine. The reaction may be carried out in a solvent which does not adversely affect the reaction (e.g. diethyl ether, dichloromethane, tetrahydrofuran, chloroform or N-methylpyrrolidone, pyridine or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from 0° C. to 100° C. The reaction may require 20 minutes to 24 hours to complete, depending on the reagent chosen.

In process (e), a suitable reagent for inversion is water. The reaction may be carried out in a solvent which does not adversely affect the reaction (e.g. dioxane, DMSO, acetonitrile, tetrahydrofuran, or N-methylpyrrolidone, pyridine or a mixture thereof). The reaction may require cooling or heating, depending on the method used. The reaction temperature is preferably from 0° C. to 100° C. The reaction may require 20 minutes to 24 hours to complete, depending on the solvent chosen.

In process (f), a suitable reagent and solvent for inversion is N,N-dimethylformamide. The reaction temperature is preferably from 0° C. to 100° C. The reaction may require 20 minutes to 24 hours to complete.

In process (g), suitable reagents are H—$SR^{21}$, H—$NR^{24}R^{25}$, or $H_2NC(S)NH_2$ and a secondary- or tert-amine base such as morpholine or Hunig's base. The reaction may be carried out in a solvent which does not adversely affect the reaction (e.g. methylene chloride, dioxane, acetonitrile, tetrahydrofuran, N,N,N,N,-tetraalkylurea, or N-methylpyrrolidone, pyridine or a mixture thereof). The reaction temperature is preferably from 0° C. to 100° C. The reaction may require 20 minutes to 24 hours to complete.

In processes (h), (i), (j), (k), (l), (m), (n) and (o), ether formation may be carried out using, for example, appropriately substituted alkyl halides in the presence of KY-zeolite (Onaka, M.; Kawai, M.; Izumi, Y. *Chem. Lett.* 1983, 1101), polymeric materials (Kimura, Y.; Kirszensztejn, P.; Regen, S. L. *J. Org. Chem.* 1983, 48,385), nickel-catalysis (Camps, F.; Coll, J.; Moreto, J. M. *Synthesis* 1982, 186; Yamashita. *Synthesis* 1977, 803), arylalkyl-O-p-toluenesulfonate (Dewick, P. M. *Synth. Commun.* 1981, 11,853), potassium or sodium alkoxides (Bates, R. B.; Janda, K. D. *J. Org. Chem.* 1982, 47, 4374), pyridine or other bases (*Chem. Lett.* 1978, 57), tetraalkylammonium halide (Miller, J. M.; So, K. H.; Clark, J. H. *Can. J. Chem.* 1979, 1887), mercury perchlorate (McKillop, A.; Ford, M. E. *Tetrahedron* 1974, 30, 2467), silver triflate or silver oxide (Kuhn, R.; Löw, I.; Trischmann, H. *Chem. Ber.* 1957, 90, 203. Croon, I.; Lindberg, B. *Acta Chem. Scand.*, 1959, 13, 593) or a phase transfer catalyst (McKillop, A.; Fiaud, J.-C.; Hug, R. P. *Tetrahedron* 1974, 30, 1379). The ether formation may also be carried out with dialkyl- or diarylphosphoric acid in the presence of p-toluenesulfonic acid (Kashman, Y. *J. Org. Chem.* 1972, 37, 912), with diazo compounds with tin(II) chloride (Christensen, L. F.; Broom, A.D. *J. Org. Chem.* 1972, 37, 3398), or with 2,2,2-trichloroalkanols in the presence of base (Corey, E. J.; Link, J. O. *J. Am. Chem. Soc.* 1992, 114, 1906; Corey, E. J.; Link, J. O. *Tetrahedron Lett.* 1992, 33, 3431). Additionally, ether formation may be accomplished with a suitable trichloroacetimidate in the presence of an acid catalyst (Wessel, H. P.; Iversen, T.; Bundle, D. R. *J. Chem. Soc. Perk Trans.* 1985, 1, 2247.) The ether formation may be carried out in a solvent which does not adversely affect the reaction (e.g. acetone, dichloromethane, tetrahydrofuran, pyridine, N,N-dimethylformamide, ether, acetonitrile, cyclohexane, etc. or a mixture thereof). The reaction may be conducted above, at, or below ambient temperature.

O-Alkylation may be carried out using substituted alkyl halides, substituted alkyl trifluoromethanesulfonates, substituted fluorosulfonates, and the like in the presence of an appropriate base such as triethylamine, potassium fluoride, silver carbonate, silver triflate or silver(I) oxide. The reaction is performed in an inert solvent such as N,N-dimethylformamide, acetonitrile or dichloromethane, preferably between −78° C. and 80° C. Alternatively, alkylation can be carried out using substituted diazoalkanes, such as diazomethane, ethyl diazoacetate, and the like, in the presence of a metal catalyst, for example $Rh(OAc)_2$ in an inert solvent such as dichloromethane preferably between −20° C. and 80° C.

In process (p), —$OCH_2$—$NHC(O)R^{24}$ formation may be carried out by first forming an —O—$CH_2$—$C(O)N_3$ by activating a —O—$CH_2$—C(O)OH in the molecule with a chloroformate, such as isobutyl chloroformate, in the presence of a tertiary amine, such as N-methyl-morpholine or N-methyl-piperidine, and treating with an azide source, such as sodium azide, hydrazoic acid, trimethylsilylazide, or tetramethylguanidinium azide. The acyl azide may also be formed directly using diphenylphophorylazide in the presence of a tertiary amine. The reaction mixture is then heated at from 40° C. to 100° C. for 0.5 to 6 hours, whereupon $R^{24}CO_2H$ is added and the reaction is heated between 40° C. and 120° C. in a inert solvent to form —$OCH_2NHC(O)R^{24}$.

In process (q), the —O—$CH_2$—$NHC(O)NR^{24}R^{25}$ formation may be carried out by first forming an —O—$CH_2$—$C(O)N_3$ by activating a —O—$CH_2$—C(O)OH in the molecule with a chloroformate, such as isobutyl chloroformate, in the presence of a tertiary amine, such as N-methyl-morpholine or N-methyl-piperidine, and treating with an azide source, such as sodium azide, hydrazoic acid, trimethylsilylazide, or tetramethylguanidinium azide. The acyl azide may also be formed directly using diphenylphophorylazide in the presence of a tertiary amine. The reaction mixture is then heated at from 40° C. to 100° C. for 0.5 to 6 hours, whereupon the amine $HNR^{24}R^{25}$ is added at a temperature at from 23° C. to 100° C. The reaction is conducted in an inert organic solvent such as diethyl ether, tetrahydrofuran, 1,4-dioxane, chloroform, methylene chloride, benzene or toluene; alternatively the —O—$CH_2$—$NHC(O)NR^{24}R^{25}$ moiety may be formed by alkylation of the C42 hydroxyl group with LG—$CH_2$—$NHC(O)NR^{24}R^{25}$, where LG may be halogen or activated hydroxyl, such as mesylate, triflate, fluorosulfonate and the like.

In process (r) condensation of an amine with a group of formula —O—$(CH_2)_tC(O)OH$, may be performed using the mixed or symmetrical anhydride of said acid, the acyl cyanide of the carboxylic acid, or acyl azide of the carboxylic acid. Alternatively, in a group of formula —O—$(CH_2)_tC(O)OR^{20a}$, where $R^{20a}$ is defined as $R^{20}$ excluding hydrogen, $OR^{20a}$ is displaced by $NR^{24}R^{25}$, where the exchange is conducted in an inert solvent, such as dichloromethane, and may be facilitated by $Al(CH_3)_3$, $Sn[N(Si(CH_3)_3)_2]_2$, a Grignard reagent and the like.

In process (s) condensation of $NH(OR^{24})R^{25}$, where $R^{24}$ and $R^{25}$ are as defined above, with a group of formula —O—$(CH_2)_tC(O)OH$, may be performed using the mixed or symmetrical anhydride of said acid, the acyl cyanide of the carboxylic acid, or acyl azide of the carboxylic acid. Alternatively, in a group of formula —O—$(CH_2)_tC(O)OR^{20a}$, where $R^{20a}$ is defined as $R^{20}$ excluding hydrogen, $OR^{20a}$ is displaced by $N(OR^{24})R^{25}$, where the exchange is conducted in an inert solvent, such as dichloromethane, and may be facilitated by $Al(CH_3)_3$, $Sn[N(Si(CH_3)_3)_2]_2$, a Grignard reagent and the like.

In process (t) condensation of $NHR^{24}NR^{24}R^{25}$, where $R^{24}$ and $R^{25}$ are as defined above, with a group of formula —O—$(CH_2)_tC(O)OH$, may be performed using the mixed or symmetrical anhydride of said acid, the acyl cyanide of the carboxylic acid, or acyl azide of the carboxylic acid. Alternatively, in a group of formula —O—$(CH_2)_tC(O)OR^{20a}$, where $R^{20a}$ is defined as $R^{20}$ excluding hydrogen, $OR^{20a}$ is displaced by $NR^{24}NR^{24}R^{25}$, where the exchange is conducted in an inert solvent, such as dichloromethane, and may be facilitated by $Al(CH_3)_3$, $Sn[N(Si(CH_3)_3)_2]_2$, a Grignard reagent and the like.

In process (u), the —O—$CH_2$—$NHC(O)N(OR^{24})R^{25}$ formation may be carried out by first forming an —O—$CH_2$—$C(O)N_3$ by activating a —O—$CH_2$—C(O)OH in the molecule with a chloroformate, such as isobutyl chloroformate, in the presence of a tertiary amine, such as N-methyl-morpholine or N-methylpiperidine, and treating with an azide source, such as sodium azide, hydrazoic acid, trimethylsilylazide, or tetramethylguanidinium azide. The acyl azide may also be formed directly using diphenylphophorylazide in the presence of a tertiary amine. The reaction mixture is then heated at from 40° C. to 100° C. for 0.5 to 6 hours, whereupon the amine $HN(OR^{24})R^{25}$ is added at a temperature at from 23° C. to 100° C. The reaction is conducted in an inert organic solvent such as diethyl ether, tetrahydrofuran, 1,4-dioxane, chloroform, methylene chloride, benzene or toluene; alternatively the $—O—CH_2—NHC(O)N(OR^{24})R^{25}$ moiety may be formed by alkylation of the C42 hydroxyl group with $LG—CH_2—NHC(O)N(OR^{24})R^{25}$, where LG may be halogen or activated hydroxyl, such as mesylate, triflate, fluorosulfonate and the like.

In process (v), the $—O—CH_2—NHC(O)NR^{24}NR^{24}R^{25}$ formation may be carried out by first forming an $—O—CH_2—C(O)N_3$ by activating a $—O—CH_2—C(O)OH$ in the molecule with a chloroformate, such as isobutyl chloroformate, in the presence of a tertiary amine, such as N-methyl-morpholine or N-methylpiperidine, and treating with an azide source, such as sodium azide, hydrazoic acid, trimethylsilylazide, or tetramethylguanidinium azide. The acyl azide may also be formed directly using diphenylphophorylazide in the presence of a tertiary amine. The reaction mixture is then heated at from 40° C. to 100° C. for 0.5 to 6 hours, whereupon the amine $HNR^{24}NR^{24}R^{25}$ is added at a temperature at from 23° C. to 100° C. The reaction is conducted in an inert organic solvent such as diethyl ether, tetrahydrofuran, 1,4-dioxane, chloroform, methylene chloride, benzene or toluene; alternatively the $—O—CH_2—NHC(O)NR^{24}NR^{24}R^{25}$ moiety may be formed by alkylation of the C42 hydroxyl group with $LG—CH_2—NHC(O)NR^{24}NR^{24}R^{25}$, where LG may be halogen or activated hydroxyl, such as mesylate, triflate, fluorosulfonate and the like.

In process (w), suitable azide reagents include well-established alkali metal azides such as sodium or lithium azides ($NAN_3$ or $LiN_3$) in the presence or absence of crown ethers, more reactive tetraalkylammonium azides (Danishefski, S. J.; DeNinno, M. P.; Chen, S.-H. *J. Am. Chem. Soc.* 1988, 110, 3929), a copper-assisted azide reaction (Yamamoto, Y.; Asao, N. *J. Org. Chem.* 1990, 55, 5303) and a hydrogen azide-amine system (Saito, S.; Yokoyama, H.; Ishikawa, T.; Niwa, N.; Moriwake, T. *Tetrahedron Lett.* 1991, 32, 663; Saito, S.; Takahashi, N.; Ishikawa, T.; Moriwake, T. *Tetrahedron Lett.* 1991, 32, 667). The azide displacement reaction may be carried out in a solvent which does not adversely affect the reaction (e.g. chloroform, acetone dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature.

In process (x), the reduction may be carried out catalytically using hydrogen. Suitable catalysts include, but are not limited to platinum catalysts (e.g. platinum oxide, platinum black), palladium catalysts (e.g. palladium oxide, palladium on charcoal, palladium black, palladium hydroxide on charcoal, palladium on calcium carbonate poisoned with lead, palladium on barium carbonate with quinoline), nickel catalysts (e.g. nickel oxide, Raney nickel), rhodium catalysts (e.g. rhodium on alumina). Reduction may also be carried out using metal reducing reagents (see Review; Scriven, E. F. V.; Turnbull, K. *Chem Rev.* 1988, 88, 321; Patai, S., Ed., "The Chemistry of the Azido Group," Interscience Publishers, New York, 1971; Scriven, E. F. V., Ed., "Azides and Nitrenes Reactivity and Utility," Academic Press, Inc., New York, 1984) such as sodium borohydride under phase-transfer conditions, borohydride supported on an ion exchange resin, lithium aluminum hydride and the like, furthermore, 1,3-propanedithiol-triethylamine method (Bayley, H.; Staudring, D. N.; Knowles, J. R. *Tetrahedron Lett.* 1978, 3633), triphenylphosphine (Vaultier, M.; Knouzi, N.; Carrie, R. *Tetrahedron Lett.* 1983, 24, 763), and sodium tellurium hydride (Suzuki, H.; Takaoka, K. *Chem Lett.* 1984, 1733).

The reduction may be carried out in a solvent which does not adversely affect the reaction (e.g., alcohols, water, acetone, dichloromethane, tetrahydrofuran, pyridine or N,N-dimethylformamide or a mixture thereof). The reaction may be conducted above, at, or below ambient temperature.

In process (y), suitable N-acylations may be carried out using the methods of symmetric carboxylic acid anhydrides, carboxylic acid halides, mixed carbonic-carboxylic anhydrides, active esters (p-nitrophenylester, trichlorophenyl ester, pentafluorophenyl ester, N-hydroxysuccinimide, cyanoethyl and the like), and carboxylic acid with suitable condensing reagents such as DCC (N,N-dicyclohexylcarbodiimide and its related condensing agents), DCC-HOB t (N,N-dicyclohexylcarbodiimide-1-hydroxybenzotriazole), Woodward reagent K method, N,N-carbonyldiimidazole and phosphonium containing reagents (e.g. benzotriazolyloxytris[dimethylamino]phosphonium hexafluorophosphate, N,N-bis[2-oxo-3-ox-azolidinyl]phosphorodiamidic chloride, diethylphosphorobromidate, diphenylphosphoryl azide, bromo tris[dimethylamino]phosphonium hexafluorophosphate, and the like). Suitable reagents for amide formation include, but are not limited to formyl derivatives, acetyl halides (chloroacetyl, trichloroacetyl, o-nitrophenylacetyl, o-nitrophenoxyacetyl, acetoacetyl, [N'-dithiobenzyloxycarbonylamino]acetyl and the like), and substituted propionyl derivatives (3-phenylpropionyl, isobutyryl, picolinoyl, and the like). Other groups may be found in volume 3 of *The Peptides* Gross, E. and Meinhofer, J. Academic Press, 1981 and *Protective Groups in Organic Synthesis* Greene, T. W. John Wiley & Sons, New York, Chapter 7, 1981. Typically used coupling conditions are described by Gross, E.; Meinhofer, J. *"The Peptides"* vol. 3, Academic Press, 1981. The N-acylation may be carried out in a solvent which does not adversely affect the reaction (e.g. acetone, dichloromethane, chloroform, tetrahydrofuran, N,N-dimethylformamide, dimethylsulfoxide, diethylether, and the like, or a mixture thereof). The reaction may be conducted above, at, or below ambient temperature.

In process (z), urea formation may be carried out from the following reactions; reaction with silicon tetraisocyanate or silicon tetraisothiocyanate (Neville, R. G.; McGee, J. J. *Can. J. Chem.* 1963, 41, 2123), reaction with N,N-carbonyldiimidazole or N,N-thiocarbonyldiimidazole, followed by N-substituted primary or secondary amines or ammonia (Staab, H. A.; Wendel, K. *Org. Synth.* 1968, 48, 44), and reaction with phosgene or thiophosgene in the presence of tert-amine, followed by N-substituted primary or secondary amines or ammonia. The ureido formation may be carried out in a solvent which does not adversely affect the reaction (e.g. acetone, toluene, dichloromethane, tetrahydrofuran, pyridine, N,N-dimethylformamide, etc. or a mixture thereof). The reaction may be conducted above, at, or below ambient temperature.

In process (aa), N-sulfonylation may be carried out using substituted sulfonylhalides in the presence of suitable tertamines such as trialkylamine, pyridine, and the like (Remers, W. A.; Roth, R. H.; Gibs, G. J.; Weiss, M. J. *J. Org. Chem.* 1971, 36, 1232). Suitable reagents include, but are not limited to benzenesulfonyl halide, p-methyoxybenzenesulfonyl halide, 2,4,6-trimethylbenzenesulfonyl halide, toluenesulfonyl halide, benzylsulfonyl halide, p-methoxybenzylsulfonyl halide, trifluoromethylsulfonyl halide, phenacylsulfonyl halide, and the like. Some other representative groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-aryl- or alkylsulfonylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (bb), N-carbamate formations may be carried out using common protecting groups for amino group such as, but not limited to methylcarbamates (cyclopropylmethyl, 9-fluorenylmethyl, and the like), substituted ethylcarbamates (2,2,2-trichloroethyl, 2-phosphonoethyl, 2methylthioethyl, and the like), substituted propyl and isopropylcarbamates (1,1-dimethylpropynyl, 1-methyl-1-(4-biphenylyl)ethyl, tert-butyl, phenyl, p-nitrobenzyl, 8-quinolyl, N-hydroxypiperidinyl, benzyl, dimethoxybenzyl, 9-anthrylmethyl, 1-adamantyl, cyclohexyl, tert-amyl, cinnamoyl, isobutyl, N'-p-phenylaminothiocarbonyl, N'-piperidinylcarbonyl, diphenylmethyl, and the like). Preparations of N-carbamates and other groups may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-carbamate formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (cc), N-sulfenamides may be prepared from an amine and a sulfenyl halide (Davis, F. A.; Nadir, U. K. *Org. Prep. Proc. Int.* 1979, 11, 33; Kobayashi, T.; Iino, K.; Hiraoka, T. *J. Am. Chem. Soc.* 1977, 99, 5505; Zervas, L.; Borovas, D.; Gazis, E. *J. Am. Chem. Soc.* 1963, 85, 3660). Suitable reagents include, but are not limited to benzenesulfenyl halide, o-nitrobenzenesulfenyl halide, 2,4-dinitrosulfenyl halide, pentachlorobenzenesulfenyl halide, 2-nitro-4-methoxybenzenesulfenyl halide, triphenylmethylsulfenyl halide, and the like. Other groups may be found in volume 3 of *The Peptides*, Gross, E. and Meinhofer, J. Academic Press, 1981 *and Protective Groups in Organic Synthesis*, Greene, T. W. John Wiley & Sons, New York, Chapter 7, 1981. The N-sulfenylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (dd), —N=C=O may be prepared from an amine and oxalyl chloride, phosgene, diphosgene or triphosgene with or without the presence of a base (Weisenfeld, R. B., J. *Org. Chem.*, 51 (13): 2434–2436, 1986; Eckert, H., Forster, B., *Angew. Chemie*, IE, 26(9): 894–895, 1987; Arnold-Stanton, R., Lemal, D. J., *J. Org. Chem.*, 56(1), 146–151, 1991; Danda, H., Chino, K., Wake, *S., Chem. Exp.*, 6(4), 261–264, 1991). Suitable base for the reaction are triethylamine, diisopropylethylamine, pyridine, 2,6-lutidine etc.

The reaction may be carried out in a solvent which does not adversely affect the reaction (e.g. ether, toluene, dichloromethane, chloroform, chlorobenzene etc.). The reaction may be conducted above, at, or below room temperature.

In process (ee), a —SePh group may be prepared by selective displacement of an —OS(O)$_2$F or —OS(O)$_2$CF$_3$ with benzeneselenol in the presence of a base.

Suitable bases for the reaction are triethylamine, diisopropylethylamine, pyridine, 2,6-lutidine etc. The reaction may be carried out in a solvent which does not adversely affect the reaction (e.g. ether, toluene, dichloromethane, chloroform, chlorobenzene etc.). The reaction may be conducted above; at, or below room temperature.

In process (ff), a —Se(O)Ph group may be prepared by selective oxidation of an —Se-Ph group with appropriate peroxides in the presence of a base.

Suitable peroxides are hydrogen peroxide, trifluoroperacetic acid, peracetic acid, or m-chloroperbenzoic acid, etc. Suitable base for the reaction are sodium bicarbonate, potassium bicarbonat, or cesium bicarbonate, etc. The reaction may be carried out in a solvent which does not adversely affect the reaction (e.g. ether, toluene, dichloromethane, chloroform, chlorobenzene etc.). The reaction may be conducted above, at, or below room temperature.

In process (gg), a compound of formulae IV, where one of $R^8$ and $R^9$ with one of $R^{18}$ and $R^{19}$ taken together form a bond, the others of $R^8$, $R^9$, $R^{18}$ and $R^{19}$ are hydrogen, by selective 1,2-elimination of an H-OSePh group in a corresponding compound containing an —Se(O)Ph group with or without the presence of base.

Suitable base for the reaction are sodium bicarbonate, potassium bicarbonat, or cesium biccarbonate, etc. The reaction may be carried out in a solvent which does not adversely affect the reaction (e.g. ether, toluene, dichloromethane, chloroform, chlorobenzene etc.). The reaction may be conducted at or above room temperature.

In process (hh), selective oxidation of a double bond to form a 1,2-diol may be carried out using tertiary amine N-oxide-osmium tetraoxide (VanRheenen, V., Kelly, R. C. and Cha, D. Y. *Tetrahedron Lett.*, 1976, 25, 1973–1976; Fraser-Reid, B., Molino, B. F., Magdzinski, L. and Mootoo, D. R. *J. Org. Chem.*, 1987, 52, 4505–4511); pyridine-osmium tetraoxide (Cimino, G., Gavagnin, M., Sodano, G., Spinnella, A., Strazzullo, G., Schmitz, F. J. and Yalamanchili, G. *J. Org. Chem.*, 1987, 52,2301–2303.). chiral amine-osmium tetraoxide (Yamada, T. and Narasaka, K. *Chem. Lett.*, 1986, 13 1; Tokles, M. and Snyder, J. K. *Tetrahedron Lett.*, 1986, 27, 3957).

The reaction may be carried out in a solvent which does not adversely affect the reaction (e.g., diethylether, dichloromethane, tetrahydrofuran, acetonitrile, chloroform or N,N-dimethylformamide or a mixture thereof). The reaction may require cooling or heating, depending on the method chosen.

In process (ii), protection and derivatization for 1,2-diol may be carried out as cyclic acetals, cyclic ketals, cyclic ortho esters, cyclic boronates, cyclic carbonates, or as cyclic silyl derivatives. Suitable cyclic acetal and cyclic ketal formations may be carried out using a reaction of the diol and a carbonyl compound in the presence of an acid catalyst (Fletcher, Jr. H. G *Methods Carbohydr. Chem.,* 1963, H, 307; Amarnath, V. and Broom, A.D. *Chem. Rev.,* 1977, 77, 183; Reese, C. B. *Tetrahedron,* 1978,34, 3143; Clode, D. M. *Chem. Rev.* 1979, 79, 491; Hanessian, S., Chung, G. Y., Lavallee, P. and Pernet, A. G. *J. Am. Chem. Soc.,* 1972, 94, 8929; Yuceer, L. *Carbohydr. Res.,* 1977, 56, 87.). Cyclic ortho ester formation, including cyclic orthoformates, may be carried out using a wide variety of reagents, but not limited to tetramethyl orthocarbonate-p-toluenesulfonic acid method (Niaz, G. R. and Reese, C. B. *J. Chem. Soc. Chem. Commun.*, 1969, 552), or acid catalized transketalization (Reese, C. B. *Tetrahedron*, 1978, 34, 3143; Amarnath, V. and Broom, A.D. *Chem. Rev.*, 1977, 77, 183; Ahmad, M., Bergstrom, R. G., Cashen, M. J., Kresge, A. J., MaClelland, R. A. and Powell, M. F. *J. Am. Chem. Soc.*, 1977, 99, 4827). Cyclic carbonate may be prepared from 1,2-diol and phosgene or a chloroformate (Hough, L., Priddle, J. E. and Theobald, R. S. *Adv. Carbohydr. Chem.*, 1960, 15, 91–158; Amarnath, V. and Broom, A.D. *Chem. Rev.*, 1977, 77, 183; Letsinger, R. L. and Ogilvie, K. K. *J. Org. Chem.*, 1967, 32,296; Kutney, J. P. and Ratcliffe, A. H. *Synth. Commun.*, 1975, 5, 47.). Cyclic silyl derivatives of 1,2-diol may be prepared from the reaction using bis-(tert-butyl)dichlorosilane-triethylamine (*Tetrahedron Lett.*, 1981, 22, 4999), or diisopropylsilyl bis(trifluotomethanesulfonate)-tert-amine (*Tetrahedron Lett.*, 1982, 23,4871), and the like. Cyclic boronates formation may be carried out using following references (Ferrier, R. *J. Adv. Carbohydr. Chem. Biochem.*, 1978, 35, 31–80; Frechet, J. M. J., Nuyens, L. J. and Seymour, E. *J. Am. Chem. Soc.*, 1979, 101, 432).

The reaction may be carried out in a solvent which does not adversely affect the reaction (e.g., diethylether, dichloromethane, tetrahydrofuran, acetonitrile, chloroform or N,N-dimethylformamide or a mixture thereof). The reaction may require cooling or heating, depending on the method chosen.

In process (jj), suitable reducing agents are trialkylsilanes. Suitable acids are toluenesulfonic acid, trifluroacetic acid, borotrifluoride etherate etc. The reaction may be carried out in a solvent which does not adversely affect the reaction (e.g., diethylether, dichloromethane, tetrahydrofuran, or chloroform or a mixture thereof). The reaction may be conducted at –50° to 0° C.

In process (kk), suitable alkylating agents are allyltrimethylsilane or alkyl alcohol. Suitable acids are toluenesulfonic acid, trifluroacetic acid, borotrifluoride etherate etc. The reaction may be carried out in a solvent which does not adversely affect the reaction (e.g., diethylether, dichloromethane, tetrahydrofuran, or chloroform or a mixture thereof). The reaction may be conducted at –50° to 0° C.

In process (11), a suitable reagent for activation of the alcohol of formula is fluorosulfonyl anhydride (prepared according to the procedure described by S. Kongpricha, W. G. Preusse and R. Schwarer, in Inorganic Synthesis, 1968, 11, p 115-155) or trifluoromethanesulfonyl anhydride. The activation may be carried out in a solvent which does not adversely affect the reaction (e.g. diethyl ether, dichloromethane, tetrahydrofuran, chloroform or N-methylpyrrolidone or a mixture thereof). The reaction may require cooling or heating, depending on the method used. Further, the reaction is preferably conducted in the presence of an organic or inorganic base such as cesium bicarbonate, pyridine, lutidine, picoline, quinoline, diisopropylethylamine and the like. The reaction temperature is preferably from –100° to 30° C., and more preferably from –78° to 0° C. The reaction may require 20 minutes to 24 hours to complete, depending on the reagent chosen.

A suitable reagent for the dehydration of an activated alcohol is silica gel or triethylamine. The reaction may be carried out in a solvent which does not adversely affect the reaction (e.g. diethyl ether, dichloromethane, tetrahydrofuran, chloroform or toluene or a mixture thereof). The reaction may require cooling or heating, depending on the method used. The reaction temperature is preferably from –100° to 30° C., and more preferably from –20° to 0° C. The reaction may require 20 minutes to 24 hours to complete, depending on the conditions chosen. The hydrolysis of the dehydrated enol ether

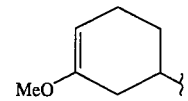

may be carried out in dilute aqueous acid at room temperature.

In process (mm), a suitable acid for the rearrangement of the activated alcohol is silica gel. The reaction may be carried out in a solvent which does not adversely affect the reaction (e.g. diethyl ether, dichloromethane, tetrahydrofuran, chloroform or toluene or a mixture thereof). The reaction may require cooling or heating, depending on the method used. The reaction temperature is preferably from –100° to 30° C., and more preferably from –20° to 0° C. The reaction may require 20 minutes to 24 hours to complete, depending on the conditions It should be noted that numerous asymmetric centers may exist in the compounds of the present invention. Except where otherwise specified, the present invention contemplates the various stereoisomers and mixtures thereof. It should also be noted that certain variable elements of the structural formulae herein, such as the radicals $R^{11}$, $R^{20}$, $R^{24}$, $R^{25}$, $R^{26}$ and $R^{27}$ or the subscript integers m and s, may appear more than once in a particular formula. In such instances, it is intended that, within a single formula, the values of these variables may be the same or different at each occurrence.

The present invention can be illustrated by the following non-limiting, representative examples. In the following examples, unless states otherwise, $R^{10a}$=—$OCH_3$ and $R^{10b}$=H.

The following abbreviations are used: DDQ for 2,3-dichloro-5,6-dicyano-1,4-benzoquinone, EDAC for 1-ethyl-3-(3'-dimethylamino)-propylcarbodiimide, EtOAc for ethyl acetate, EtOH for ethanol, HOBt for 1-hydroxybenzotriazole, and MeOH for methanol.

EXAMPLE 1

Formula VI: $R^1$=methyl; $R^2$=—H; $R^3$=—OH; $R^4$ and $R^5$ taken together=O; $R^6$ and $R^7$ taken together=O; X and Y taken together=O; R=F; $R^9$=H Fluorosulfonyl anhydride (0.17 g, in 1 mL of dry $CH_2Cl_2$) was added into a stirred solution of rapamycin (0.457 g) and 2,6-lutidine (0.22 g) in dry dichloromethane (5 mL) at –70° C. After being stirred at –70° C. for 1 hour, the reaction mixture was partitioned between ether and ice-cold 0.1N hydrochloric acid. The organic phase was washed once with saturated brine, dried over magnesium sulfate and filtered through silica gel (2 g) eluting with ether. The solvent was removed in vacuo, and the product was storm in the freezer.

EXAMPLE 2

Formula VII: $R^1$=methyl: $R^2$=—H; $R^3$=—OH; $R^4$ and $R^5$taken together=O; $R^6$ and $R^7$ taken together=O: X and Y taken together=O; $R^8$=—OC(=O)—O(p-Nitro-phenyl); $R^9$=—H 4-Nitrophenyl chloroformate (0.5 g) was added into a stirred solution of rapamycin (0.9 g) in dry pyridine (2 mL) at room temperature. After being stirred at 40°–50° C. for 0.5 hour, the reaction was cooled to 0° C. and partitioned between ether and ice-cold 0.4N hydrochloric acid. The organic phase was washed once with brine, dried over magnesium sulfate and solvent removed in vacuo. The product was purified by silica gel chromatography (20 g) eluting with 20% acetone/hexanes to afford 0.72 g of the title compound. MS (FAB) m/z: M+K=1117.

EXAMPLE 3

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)-morpholine; $R^9$=—H To the compound resulting from Example 2 (514.5 mg) dissolved in 3.5 mL of anhydrous dichlormethane at 0° C. was added morpholine (250 μL). The reaction mixture was allowed to warm to room temperature and stirred for 2 hours. The reaction mixture was purified by silica gel chromatography (70 g) eluting with 25% acetone/hexanes to give 343.2 mg of the title compound. m.p. 115°–199° C. MS (FAB)m/z: M+K=1065.

EXAMPLE 4

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—O(N-succinimidyl); $R^9$=—H The title compound is prepared from rapamycin and di-(N-succinimidyl)carbonate in pyridine according to the procedure described in Example 2.

EXAMPLE 5

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—(N-triazole); $R^9$=—H The title compound is prepared from rapamycin and 1,1'-carbonyldiimidazole in pyridine according to the procedure described in Example 2.

EXAMPLE 6

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—(N-imidazole); $R^9$=—H The title compound is prepared from rapamycin and 1,1'-carbonyldiimidazole in pyridine according to the procedure described in Example 2.

EXAMPLE 7

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—O(hydroxy-benzotriazole); $R^9$=—H The title compound is prepared from rapamycin and 1,1'-carbonyldi(hydroxybenzotriazole) in pyridine according to the procedure described in Example 2.

EXAMPLE 8

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—piperidine; $R^9$=—H The title compound is prepared from the compound resulting from Example 2 and piperidine according to the procedure described in Example 3.

EXAMPLE 9

Formula I: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—O-formyl The title compound of Example 1 is dissolved in N,N-dimethylformamide and stirred at room temperature overnight. The reaction mixture is partitioned between ether and water. The organic phase is washed once with brine, dried over magnesium sulfate, and solvent removed in vauco. The product is purified by silica gel chromatography eluting with 30% acetone/hexanes.

EXAMPLE 10

Formula I: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—OH To a solution of rapamycin (505.4 mg) in 4 mL of methylene chloride cooled to −78° C. was added 140 μL of 2,6-lutidine followed by 100 μL of $(FSO_2)_2O$ in 1 mL of methylene chloride. The reaction mixture was stirred at −78° C. for 15 minutes after the addition was complete. The reaction mixture was partitioned between ether and 0.1N HCl. The organic layer was washed with 20 mL of water and 20 mL of saturated NaCl solution, dried over magnesium sulfate and passed through a silica gel plug eluting with cold ether. The solvent was removed in vacuo, and the residue was dissolved in 10 mL of a 1:1 mixture of THF and DMSO. After stirring at room temperature for 10 minutes, the reaction mixture was stored in the refrigerator for 2 days. Water (2 mL) was added, and the reaction mixture was stirred at room temperature for 1 hour. A solution was 500 mg of $NaHCO_3$ in water (50 mL) was added, and the mixture was extracted with $Et_2O$ (3×70 mL). The combined organic extracts were washed with 50 mL of dilute $NaHCO_3$ solution, 50 mL of water, and 50 mL of saturated NaCl solution, dried over $MgSO_4$ and concentrated in vacuo. The residue obtained was chromatographed on a silica gel (15 g) column eluting with 4% isopropanol in dichlormethane to give 271 mg of the title compound. m.p. 90°–93° C. MS (FAB) m/z: M+K=952. Selected CMR ($CDCl_3$): 215.2, 208.1, 192.8, 169.7, 169.3, 166.7, 140.5, 140.1,136.0, 135.7, 133.6, 133.3, 130.2, 129.5, 129.0, 126.7, 126.4, 98.7, 98.5, 86.4, 84.9, 84.3, 80.6, 77.2, 75.6, 67.8, 67.2, 65.5, 59.3, 59.0, 56.4, 55.9, 51.3, 46.5, 46.0, 44.2, 41.4, 40.7, 40.2, 39.0, 38.7, 35.6, 35.2, 34.4, 33.8, 33.1, 32.9, 32.4, 31.4, 30.9, 29.6, 27.2, 27.1, 25.3, 24.4, 21.5, 20.7, 16.3, 16.2, 16.0, 15.9,13.7, 13.2 and 10.2.

EXAMPLE 11

Formula I: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—OC(=O)—O(p-Nitro-phenyl)

The title compound is prepared from the compound resulting from Example 10 and 4-nitrophenyl chloroformate according to the procedure described in Example 2.

EXAMPLE 12

Formula I: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—OC(=O)-morpholine The title compound is prepared from the compound resulting from Example 11 and morpholine according to the procedure described in Example 3.

EXAMPLE 13

Formula VI: $R^1$=methyl; $R^2$=—H; $R^3$=—OH; $R^4$ and $R^5$ taken together=O; $R^6$ and $R^7$ taken together=O; X and Y taken together=O; $R^9$=H; R=—$CF_3$ Trifluoromethanesulfonyl anhydride (0.2 g) in 1 mL of dry $CH_2Cl_2$ was added into a stirred solution of rapamycin (0.457 g) and 2,6-lutidine (0.22 g) in dry dichloromethane (5 mL) at −70° C. After being stirred at that temperature for 1 hour, the reaction mixture was partitioned between ether and ice-cold 0.1N hydrochloric acid. The organic phase was washed once with saturated brine, dried over magnesium sulfate and filtered through silica gel (2 g) eluting with ether. The solvent was removed in vacuo, and the product was stored in the freezer.

EXAMPLE 14

Formula I: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—$OS(O)_2F$ The title compound is prepared from the compound resulting from Example 10 and fluorosulfonyl anhydride according to the procedure described in Example 1.

EXAMPLE 15

Formula I: $R^1$=—methyl; $R^2$=—H; $R^3$=—OH; $R^4$ and $R^5$ taken together=O; $R^6$ and $R^7$ taken together=O; X and Y taken together=O; $R^8$=—H; $R^9$=—$OS(O)_2CF_3$ The title compound is prepared from the compound resulting from Example 10 and trifluoromethanesulfonyl anhydride according to the procedure described in Example 1.

EXAMPLE 16

Formula V: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—NMe(OH); $R^9$=—H The title compound was prepared from the compound resulting from Example 2 and N-methyl hydroxylamine according to the procedure described in Example 3.

EXAMPLE 17

Formula V: $R^1$=methyl; $R^2$=—H; $R^3$=—OH; $R^4$ and $R^5$ taken together=O; $R^6$ and $R^7$ taken together=O; X and Y taken together=O: $R^8$=—OC(=O)—NMe(OMe): $R^9$=—H To N,O-dimethylhydroxylamine hydrochloride 449.8 mg, 4.6 mmol) was added pyridine (5 mL), and the mixture was stirred at room temperature for 1 hour. To this solution was added the compound resulting from Example 2 (826.2 mg, 0.701 mmol) at 0° C. under nitrogen. The reaction mixture was stirred at room temperature overnight. The reaction mixture was partitioned between 0.5 N HCl and $Et_2O$. The organic phase was washed with saturated NaCl solution, dried over $MgSO_4$ and passed through a short column of silica gel (10 g). The partially purified compound was further purified by HPLC (Rainin Microsorb silica gel) eluting with 75% acetone in hexane to afford the title compound. m.p. 105°–109° C. MS (FAB) m/z: M+K=1039. Selected CMR ($CDCl_3$): 215.5 208.1, 207.6, 192.5, 169.8, 169.2, 166.8, 156.9, 140.8, 140.2, 136.1, 135.5, 133.7, 133.4, 130.1, 130.0, 129.6, 129.3, 126.7, 126.4, 98.5, 86.5, 84.9, 84.4, 81.1, 78.1, 77.2, 75.5, 67.8, 67.2, 61.5, 59.3, 57.6, 56.2, 55.9, 51.3, 46.6, 46.1, 44.2, 41.4, 40.7, 40.2, 38.9, 38.3, 36.1, 35.6, 35.1, 34.6, 33.8, 33.3, 33.0, 32.9, 31.6, 31.3, 30.1, 27.9, 27.3, 27.0, 25.3, 24.3, 22.6, 21.7, 21.5, 20.7, 16.2, 16.1, 15.9, 15.0, 14.1, 13.8, 13.1 and 10.2.

EXAMPLE 18

Formula V: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—NH(OBn); $R^9$=—H The title compound is prepared from the compound resulting from Example 2 and O-benzylhydroxylamine according to the procedure described in Example 3.

EXAMPLE 19

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—(N-methylpiperazine): $R^9$=—H The title compound is prepared from the compound resulting from Example 2 and N-methyl piperazine according to the procedure described in Example 3.

EXAMPLE 20

Formula I: $R^1$=methyl; $R^2$=—H; $R^3$=—OAc; $R^4$ and $R^5$ taken together=O; $R^6$ and $R^7$ taken together=O; X and Y taken together=O; $R^8$=—OH; $R^9$=—H The title compound is prepared according to EP 0507556 (Example 4).

EXAMPLE 21

Formula I: $R^1$=methyl; $R^2$=—H; $R^3$=—O—(tert-butyldimethylsilyl); $R^4$ and $R^5$ taken together=O; $R^6$ and $R^7$ taken together=O; X and Y taken together=O; $R^8$=—O-(tert-butyldimethylsilyl); $R^9$=—H The title compound is prepared from rapamycin according to EP 0507556 (Example 4).

EXAMPLE 22

Formula I: $R^1$=methyl; $R^2$=—H; $R^3$=—OH; $R^4$ and $R^5$ taken together=O; $R^6$ and $R^7$ taken together=$NNMe_2$; X and Y taken together=O; $R^8$=—OH; $R^9$=—H.

The title compound is prepared from rapamycin according to EP 0507556 (Example 1).

EXAMPLE 23

Formula I: $R^1$=methyl; $R^2$=—H; $R^3$=—OH; $R^4$ and $R^5$ taken together=O; $R^6$ and $R^7$ taken together=$NNMe_2$; X and Y taken together=O; $R^8$=—H; $R^9$=—OH The title compound is prepared from the compound resulting from Example 10 (42-epi-rapamycin) and N,N-dimethylhydrazine according to the procedure described in Example 5 of U.S. Pat. No. 5,120,726, which is incorporated herein by reference.

EXAMPLE 24

Formula I: $R^1$=methyl; $R^2$=—H; $R^3$=—OH; $R^4$ and $R^5$ taken together $R^6$ and $R^7$ taken together=N-OMe; X and Y taken together=O; $R^8$=—H; $R^9$=—OH The title compound is prepared from rapamycin and O-methylhydroxylamine according to the procedure described in Example 5 of U.S. Pat. No. 5,120,726 and UK Patent GB 2,247,017 A which are incorporated herein by reference.

EXAMPLE 25

Formula I: $R^1$=methyl; $R^2$=—H; $R^3$=—O—(tert-butyldimethylsilyl); $R^4$ and $R^5$ taken together=O; $R^6$ and $R^7$ taken together=O; X and Y taken together=O; $R^8$=—OH; $R^9$=—H.

Two equivalents of 48% aquous HF in acetonitrile is added dropwise into a stirred solution of the compound resulting from Example 21 in acetonitrile at 0° C. After being stirred at that temperature for 1 hour, powdered sodium bicarbonate is added and stirred for another 0.5 hour. The solids are filtered off and the product is purified by silica gel chromatography.

EXAMPLE 26

Formula I: $R^1$=methyl; $R^2$=—H; $R^3$=—OH; $R^4$ and $R^5$ taken together=O; $R^6$ and $R^7$ taken together=N-OMe; X and Y taken together=O; $R^8$=—H; $R^9$=—OS(O)$_2$F The title compound is prepared from the compound resulting from Example 24 and fluorosulfonyl anhydride according to the procedure described in Example 1.

EXAMPLE 27

Formula VI: $R^1$=methyl; $R^2$=—H; $R^3$=tert-butyldimethylsiloxy; $R^4$ and $R^5$ taken together=O; $R^6$ and $R_7$ taken together=O; X and Y taken together=O; R=F; $R^9$=H The title compound is prepared from the compound resulting from Example 25 and fluorosulfonyl anhydride according to the procedure described in Example 1.

EXAMPLE 28

Formula VI: $R^1$=methyl; $R^2$=—H; $R^3$=—OAc; $R^4$ and $R^5$ taken together=O; $R^6$ and $R^7$ taken together=O; X and Y taken together=O; R=F; $R^9$=—H The title compound is prepared from the compound resulting from Example 20 and fluorosulfonyl anhydride according to the procedure described in Example 1.

EXAMPLE 29

Formula I: $R^1$=methyl; $R^2$=—H; $R^3$=—OH; $R^4$ and $R^5$ taken together=O; $R^6$ and $R^7$ taken together=N-OMe; X and Y taken together=O; $R^8$=—H; $R^9$=—OC(=O)—O(p-Nitrophenyl).

The title compound is prepared from the compound resulting from Example 24 and 4-nitrophenyl chloroformate according to the procedure described in Example 2.

EXAMPLE 30

Formula VII: $R^1$=methyl; $R^2$=—H; $R^3$=——(tert-butyldimethylsilyl); $R^4$ and $R^5$ taken together=O; $R^6$ and $R^7$ taken together=O; X and Y taken together=O; $R^6$=—OC(=O)—O—(p-Nitro-phenyl); $R^9$=—H The title compound is prepared from the compound resulting from Example 25 and 4-nitrophenyl chloroformate according to the procedure described in Example 2.

EXAMPLE 31

Formula VII: $R^1$=methyl; $R^2$=—H; $R^3$=—OAc; $R^4$ and $R^5$ taken together=O; $R^6$ and $R^7$ taken together=O; X and Y taken together=O; $R^8$=—OC(=O)—O—(p-Nitro-phenyl): $R^9$=—H The title compound is prepared from the compound resulting from Example 20 and 4-nitrophenyl chloroformate according to the procedure described in Example 2.

EXAMPLE 32

Formula VII: $R^1$=methyl; $R^2$=—H; $R^3$=—OH; $R^4$ and $R^5$ taken together=O; $R^6$ and $R^7$ taken together=N-OMe; X and Y taken together=O; $R^8$=—OC(=O)-morpholine; $R^9$=—H The title compound is prepared from the compound resulting from Example 29 and morpholine according to the procedure described in Example 3.

EXAMPLE 33

Formula VII: $R^1$=methyl; $R^2$=—H; $R^3$=—O-(tert-butyldimethylsilyl); $R^4$ and $R^5$ taken together=O; $R^6$ and $R^7$ taken together=O; X and Y taken together=O; $R^8$=—OC(=O)-morpholine; $R^9$=—H The title compound is prepared from the compound resulting from Example 30 and morpholine according to the procedure described in Example 3.

EXAMPLE 34

Formula VII: $R^1$=methyl: $R^2$=—H; $R^3$=—OAc; $R^4$ and $R^5$ taken together=O; $R^6$ and $R^7$ taken together=O; X and Y taken together=O; $R^8$=—OC(=O)-morpholine; $R^9$=—H The title compound is prepared from the compound resulting from Example 31 and morpholine according to the procedure described in Example 3.

EXAMPLE 35

Formula IVc: $R^1$=methyl; $R^2$=—H; $R^3$=—OH; $R^4$ and $R^5$ taken together=O; $R^6$ and $R^7$ taken together=O; X and Y taken together=O; $R^8$ and $R^9$ taken together=O Silica gel (25 g) was added to a solution of the compound resulting from Example 13 (prepared from 0.53 g of rapamycin) in ether at 0° C. The solvent was then removed in vacuo, and the resulting powder was refrigerated for 8 days at 8° C. The product on silica gel was eluted with acetone and the solvent removed in vacuo. The crude product was purified by HPLC (Rainin Microsorb silica gel) eluting with 30% acetone/hexanes. MS (FAB) m/z: M+K=920.

EXAMPLE 36

Formula IVa: $R^1$=methyl; $R^2$=—H; $R^3$=—OH; $R^4$ and $R^5$ taken together=O; $R^6$ and $R^7$ taken together=O; X and Y taken together=O Silica gel (25 g) was added to a solution of the compound resulting from Example 13 (prepared from 0.53 g of rapamycin) in ether at 0° C. The solvent was then removed in vacuo, and the resulting powder was refrigerated for 8 days at 8° C. The product on silica gel was eluted with acetone and solvent removed in vacuo. The crude product was purified by HPLC (Rainin Microsorb silica gel) eluting with 30% acetone/hexanes. MS (FAB) m/z: M+K=934.

EXAMPLE 37

Formula IVb: $R^1$=methyl; $R^2$=—H; $R^3$=—OH; $R^4$ and $R^5$ taken together=O; $R^6$ and $R^7$ taken together=O; X and Y taken together=O; $R^8$=$R^{18}$=—H; $R^9$ and $R^{19}$ taken together form a bond The title compound was isolated from the reaction mixture on silica gel of Example 36. MS (FAB) m/z: M+K=934.

EXAMPLE 38

Formula II: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—S—(2'-imidazole)

To a solution of rapamycin (838 mg, 0.917 mmol) in 5 mL of methylene chloride was added 450 μL of 2,6-lutididine at −78° C. followed by (FSO$_2$)$_2$O (200 μL). The reaction mixture was stirred for 20 minutes under a nitrogen atmosphere and then 204 mg of 2-mercaptoimidazole in 5 mL of THF was added. The reaction mixture was allowed to warm to room temperature and stirred overnight under nitrogen. The reaction mixture was partitioned between 150 mL of water and a mixture of 21:1 EtOAc and Et$_2$O. The aqueous phase was extracted with two 100 mL portions of the organic solvent mixture. The combined organic extracts were washed twice with water and once with saturated sodium chloride solution, dried over MgSO$_4$ and concentrated in vacuo. The residue was purified on a silica gel column eluting with 1:1 acetone-hexane to give 380 mg of partially purified material which was further purified by HPLC eluting with 5% isopropanol in methylene chloride. m.p. 122°–126° C. MS (FAB) m/z: M+K=1034.

EXAMPLE 39

Formula II: $R^1$=methyl; $R^2$=—H; $R^3$=—OH; $R^4$ and $R^5$ taken together=O; $R^6$ and $R^7$ taken together=O; X and Y taken together=O; $R^8$=—H; $R^9$=—S -(2'-N-methyl-imidazole)

To a solution of rapamycin (639 mg, 0.699 mmol) in 10 mL of methylene chloride was added 250 μL of 2,6-lutididine at −78° C. followed by (FSO$_2$)$_2$O (160 μL). The reaction mixture was stirred for 20 minutes under a nitrogen atmosphere and then partitioned between ether and 0.1N HCl. The organic phase was passed through a silica gel plug eluting with Et$_2$O. This activated intermediate was dissolved in methylene chloride (8 mL), cooled to −78° C., and treated with 2,6-lutidine (250 μL) followed by 1-methyl-2-mercaptoimidazole (171.4 mg). The reaction mixture was stirred under a nitrogen overnight and then partitioned between Et$_2$O and 0.1N HCl. The organic phase was concentrated in vacuo, and the residue obtained purified on a silica gel column eluting with 4% isopropanol in methylene chloride to give 159 mg of the title compound. m.p. 111°–116° C. MS (FAB) m/z: M+K=1048.

EXAMPLE 40

Formula VII: $R^1$=methyl; $R^2$=$R^9$=H, $R^3$=OH, $R^4$ and $R^5$ taken together are oxo; $R^6$ and $R^7$ taken together are oxo; X and Y taken together are oxo; $R^8$=OCH$_2$C(O)NHPh A solution of rapamycin (0.58 g, 0.63 mmol) in dichloromethane (10 mL) containing rhodium(II)acetate dimer (3 mg) is refluxed while N-phenyl-diazoacetamide (101 mg, 0.63 mmol) in dichloromethane (1 mL) is added dropwise. After complete addition the reaction is refluxed for 30 minutes and additional N-phenyl-diazoacetamide (202 mg, 1.26 mmol) in dichloromethane (1.5 mL) is added dropwise with reflux continuing 30 minutes after complete addition. The solvent is removed in vacuo and the residue purified by HPLC on silica gel. Fractions containing desired product are pooled, and concentrated, to constant weight under high vacuum to give the desired product.

EXAMPLE 41

Formula VII: $R^1$=methyl; $R^2$=$R^9$=H, $R^3$=OH, $R^4$ and $R^5$ taken together are oxo; $R^6$ and $R^7$ taken together are oxo; X and Y taken together are oxo; $R^8$=OCH2C(O)N(CH$_2$CH$_2$)$_2$O A solution of rapamycin (0.58 g, 0.63 mmol) in dichloromethane (10 mL) containing rhodium(II)acetate dimer (3 mg) is refluxed while morpholinodiazoacetate (98 mg, 0.63 mmol) in dichloromethane (1 mL) is added dropwise. After complete addition the reaction is refluxed for 30 minutes and additional morpholino-diazoacetate (196 mg, 1.26 mmol) in dichloromethane (1.5 mL) is added dropwise with reflux continuing 30 minutes after complete addition. The solvent is removed in vacuo and the residue purified by HPLC on silica gel. Fractions containing desired product are pooled, and concentrated, to constant weight under high vacuum to give the desired product.

EXAMPLE 42

Formula VII: $R^1$=methyl; $R^2$=$R^9$=—H; $R^3$=—OH; $R^4$ and $R^5$ taken together=O; $R^6$ and $R^7$ taken together=O; X and Y taken together=O; $R^8$=—OCH$_2$C(O)NH(4-Cl-Ph)

A solution of rapamycin (0.58 g, 0.63 mmol) in dichloromethane (10 mL) containing rhodium(II)acetate dimer (3 mg) is stirred at 0° C. while N-p-Cl-phenyl diazoacetamide (101 mg, 0.63 mmol) in dichloromethane (1 mL) is added dropwise (24 hours). After complete addition the reaction is maintained at 0° C. for an additional 24 hours. The solvent is removed in vacuo and the residue purified by chromatography on silica gel to provide the title compound.

EXAMPLE 43

Formula VII: $R^1$=methyl; $R^2$=$R^9$=—H; $R^3$=—OH; $R^4$ and $R^5$ taken together=O; $R^6$ and $R^7$ taken together=O; X and Y taken together=O; $R^8$=—OCH$_2$C(O)NR$^{24}$R$^{25}$, where $R^{24}R^{25}$ taken together is (CH$_2$CH$_2$)$_2$O.

The title compound is prepared using the procedure described in Example 42 and substituting 4-(2-diazo-1-oxoethyl)-morpholine for N-phenyl diazoacetamide.

EXAMPLE 44

Formula VII: $R^1$=methyl; $R^2$=$R^9$=—H; $R^3$=—OH; $R^4$ and $R^5$ taken together=O: $R^6$ and $R^7$ taken together=O; X and Y taken together=O; $R^8$=—OCH$_2$C(O)NHCH$_2$CH$_2$CH$_2$OC(O)CH$_3$.

The title compound is prepared using the procedure described in Example 42 and substituting N-(3-acetyloxypropyl)-diazoacetamide for N-phenyl diazoacetamide.

EXAMPLE 45

Formula VII: $R^1$=methyl; $R^2$=$R^9$=—H; $R^3$=—OH; $R^4$ and $R^5$ taken together=O; $R^6$ and $R^7$ taken together=O; X and Y taken together=O; $R^8$=—OCH$_2$C(O)NH(4-pyridyl).

The title compound is prepared using the procedure described in Example 42 and substituting N-(4-pyridyl)-diazoacetamide for N-phenyl diazoacetamide.

EXAMPLE 46

Formula VII: $R^1$=methyl; $R^2$=$R^9$=—H; $R^3$=—OH; $R^4$ and $R^5$ taken together=O; $R^6$ and $R^7$ taken together=O; X and Y taken together=O; $R^8$=—OCH$_2$C(O)NHCH$_2$C(O)O(fluorenylmethyl).

The title compound is prepared using the procedure described in Example 42 and substituting N-(2-(fluorenylmethyloxy)-2-oxo-ethyl)-diazoacetamide for N-phenyl diazoacetamide.

EXAMPLE 47

Formula VII: $R^1$=methyl; $R^2$=$R^9$=—H; $R^3$=—OH; $R^4$ and $R^5$ taken together=O; $R^6$ and $R^7$ taken together=O; X and Y taken together=O; $R^8$=—OCH$_2$C(O)NHCH$_2$C(O)OH The compound resulting from Example 46 is dissolved in dichloromethane and treated with 1 equivalent of piperidine. After complete consumption of starting material, as evidenced by TLC, the material is purified by chromatography on silica gel to provide the title compound.

EXAMPLE 48

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—N(2'-pyridylmethyl)(N,N-dimethylaminopropyl); $R^9$=—H The title compound is prepared from the compound resulting from Example 2 and N-(2'-pyridylmethyl),N-(N,N-dimethylaminopropyl)amine according to the procedure described in Example 3.

EXAMPLE 49

Formula VII: $R^1$=methyl; $R^2$=—H; $R^3$=—OH; $R^4$ and $R^5$ taken together=O; $R^6$ and $R^7$ taken together=O; X and Y taken together=O; $R^8$=—OC(=O)—N(phenyl)-(N,N-dimethylaminopropyl); $R^9$=—H The title compound is prepared from the compound resulting from Example 2 and N-(phenyl)-N-(N,N-dimethylaminopropyl)amine according to the procedure described in Example 3.

EXAMPLE 50

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=N$_3$; $R^{10a}$=OCH$_3$; $R^{10b}$=H To a solution of the compound resulting from Example 13 (937.2 mg, 1.02 mmol) in 5 mL of acetone was added sodium azide (355.6 mg, 5.47 mmol) in 0.5 mL of water. The reaction mixture was stirred overnight at room temperature. Additional water (1 mL) was added, and the reaction mixture was stirred at room temperature for an additional 1 day. Anhydrous sodium sulfate (2 g) was added and stirring was continued for 30 minutes. The crude mixture was then passed through a silica gel column. This partially purified material was rechromatographed on silica gel eluting with 35% acetone in hexane to obtain the title compound (380 mg, 40%) which was recrystallized from ether. m.p. 141°–146° C. (dec). MS (FAB) m/z: M+K=977.

EXAMPLE 51

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NH$_2$; $R^{10a}$=OCH$_3$; $R^{10b}$=H To a solution of the compound resulting from Example 50 (100 mg, 0.107 mmol) in 1 mL of THF containing 0.2 mL of water was added triphenylphosphine (0.25 g, 0.954 mmol). The reaction mixture was stirred at room temperature for 3 days and then concentrated in vacuo. The residue was partitioned between Et$_2$O and water. The organic phase was dried over magnesium sulfate, concentrated in vacuo and purified by silica gel chromatography to afford the title compound. MS (FAB) m/z: M+K=951.

EXAMPLE 52

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NHAc; $R^{10a}$=OCH$_3$; $R^{10b}$=H Acetic anhydride (0.15 mL) is added into a solution of the compound resulting from Example 51 (1 g) in dichloromethane (5 mL) followed by N-methylmorpholine (0.5 mL) at 0° C. After stirring at that temperature for 30 minutes, the reaction mixture is partitioned between ether and 0.1N hydrochloric acid. The organic phase is washed once with brine, dried over magnesium sulfate and the solvent removed in vacuo. The crude product is purified by silica gel chromatography eluting with 50% acetone in hexanes.

EXAMPLE 53

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NCO; $R^{10a}$=OCH$_3$; $R^{10b}$=H A solution of triphosgene (0.15 g) in 2 mL dry dichloromethane is added into a stirred solution of the compound resulting from Example 51 (1 g) in pyridine (10 mL) at 0° C. After being stirred at that temperature for 3 hours, the reaction is partitioned between ether and 0.1N hydrochloric acid. The organic phase is washed once with brine, dried over magnesium sulfate and solvent removed in vacuo. The product is purified by silica gel chromatography eluting with 50% acetone in hexanes.

EXAMPLE 54

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NHSO$_2$Ph; $R^{10a}$=OCH$_3$; $R^{10b}$=H The title compound is prepared from the compound resulting from Example 52, benzenesulfonyl chloride and N-methylmorpholine in dichloromethane according to the procedure described in Example 52.

EXAMPLE 55

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NHC(O)NHPh; $R^{10a}$=OCH$_3$; $R^{10b}$=H Phenyl isocyanate (0.15 mL) is added into a solution of the compound resulting from Example 51 (1 g) in tetrahydrofuran (5 mL) followed by N-methylmorpholine (0.3 mL) at 50° C. After being stirred at that temperature for 30 minutes, the reaction mixture is partitioned between ether and 0.1N hydrochloric acid. The organic phase is washed once with brine, dried over magnesium sulfate and solvent removed in vacuo. The crude product is purified by silica gel chromatography eluting with 50% acetone in hexanes.

EXAMPLE 56

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=NHC(=O)NH-NMe$_2$; $R^{10a}$=OCH$_3$; $R^{10b}$=H 1,1-Dimethylhydrazine (0.07 g) is added into a solution of the compound resulting from Example 54 (1 g) in pyridine (5 mL) at 0° C. and refrigerated overnight. Pyridine is removed in vacuo, and the crude mixture is purified by silica gel chromatography eluting with 65% acetone in hexanes.

EXAMPLE 57

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=Se-Ph; $R^{10a}$=OCH$_3$; $R^{10b}$=H Benzeneselenol (0.2 mL) is added into a stirred solution of the title compound of Example 1 (1 g) and diisopropylethylamine (0.2 mL) in dry tetrahydrofuran (5 mL) at 0° C. After being stirred at that temperature for 2 hours, the reaction mixture is partitioned between ether and 0.1N hydrochloric acid. The organic phase is washed once with brine, dried over magnesium sulfate and solvent removed in vacuo. The product is purified by silica gel chromatography eluting with 40% acetone in hexanes.

EXAMPLE 58

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=Se(O)-Ph; $R^{10a}$=OCH$_3$; $R^{10b}$=H 3-Chloroperoxybenzoic acid (50–60%, 0.5 g) is added into a stirred suspension of the compound resulting from Example 56 (1 g) and powdered cesium carbonate (1 g) in dichloromethane (10 mL) at 0° C. After being stirred at that temperature for 1 hour, the reaction mixture is partitioned between ethyl acetate and 0.1N sodium bicarbonate. The organic phase is washed once with brine, dried over magnesium sulfate and solvent removed in vacuo. The product is purified by silica gel chromatography eluting with 50% acetone in hexanes.

EXAMPLE 59

Formula IVb: $R^1$=methyl; $R^2$=H; $R^3$=OH; $R^4$ and $R^5$ taken together=O; $R^6$ and $R^7$ taken together=O; X and Y taken together=O; $R^{10a}$=OCH$_3$; $R^{10b}$=H; $R^8$=$R^{18}$=OH, $R^9$=$R^{19}$=H N-Methylmorpholine N-oxide (0.26 g) is added into a stirred mixture of the compound resulting from Example 37 (0.9 g) and osmium tetroxide (0.03 mL, 4% solution in water) in tetrahydrofuran (20 mL) at room temperature for 7 days. The reaction mixture is partitioned between ether and 1N sodium hydrogen sulfite. The organic phase is washed once with brine, dried over magnesium sulfate and the solvent removed in vacuo. The product is purified by silica gel chromatography eluting with 50% acetone in hexanes.

EXAMPLE 60

Formula IVb: $R^1$=methyl; $R^2$=H; $R^3$=OH; $R^4$ and $R^5$ taken together=O; $R^6$ and $R^7$ taken together=O; X and Y taken together=O; $R^{10a}$=OCH$_3$; $R^{10b}$=H; $R^8$=$R^{18}$=H; $R^9$ and $R^{19}$ taken together form a cyclic carbonate A solution of triphosgene (0.15 g) in 2 mL dry dichloromethane is added into a stirred solution of the compound resulting from Example 58 (1 g) in pyridine (10 mL) at 0° C. After stirring at that temperature for 3 hours, the reaction is partitioned between ether and 0.1N hydrochloric acid. The organic phase is washed once with brine, dried over magnesium sulfate and the solvent removed in vacuo. The product is purified by silica gel chromatography eluting with 50% acetone in hexanes.

EXAMPLE 61

Formula IVb: $R^1$=methyl; $R^2$=H; $R^3$=OH; $R^4$ and $R^5$ taken together=O; $R^6$ and $R^7$ taken together=O; X and Y taken together=O; $R^{10a}$=OCH$_3$; $R^{10b}$=H; $R^8$=$R^{18}$=H; $R^9$ and $R^{19}$ taken together form a cyclic sulfate The title compound is prepared from the compound resulting from Example 58 and sulfuryl chloride in pyridine according to the procedure described in Example 59.

EXAMPLE 62

Formula IVb: $R^1$=methyl; $R^2$=H; $R^3$=OH; $R^4$ and $R^5$ taken together=O; $R^6$ and $R^7$ taken together=O; X and Y taken together=O; $R^{10a}$=OCH$_3$; $R^{10b}$=H; $R^8$=$R^{18}$=H; $R^9$ and $R^{19}$ taken together form a cyclic sulfite The title compound is prepared from the compound resulting from Example 58 and thionyl chloride in pyridine according to the procedure described in Example 59.

EXAMPLE 63

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—SC(=NH)NH$_2$; $R^{10a}$=OCH$_3$;$R^{10b}$=H Powdered thiourea (0.106 g) was added into a stirred solution of the compound resulting from Example 13 (0.94 g) and 2,6-lutidine (0.3 mL) at –78° C. and allowed to warm up to room temperature. After stirring at room temperature for 16 hours, the solvent was removed in vacuo, and the product was used in next step without further purification.

EXAMPLE 64

Formula II: $R^1$=methyl; $R^2$=H; $R^3$=OH; $R^4$ and $R^5$ taken together=O; $R^6$ and $R^7$ taken together=O; X and Y taken together=O; $R^8$H; $R^9$=SH; $R^{10a}$=OCH$_3$; $R^{10b}$=H The compound resulting from Example 63 was added 85 μL (1 equivalent) of morpholine at room temperature. After stirring for two hours, an additional 20 μL of morpholine was added and stirring was continued for an additional hour. An additional aliquot of morpholine (60 μL) was added and stirring was continued for an additional 30 minutes. The reaction mixture was partitioned between ethyl acetate and water. The organic phase was dried over magnesium sulfate and concentrated in vacuo. The residue was purified by silica gel chromatography to give the title compound (189 mg). m.p. 105°–111° C. MS (FAB) m/z: M+K=968.

EXAMPLE 65

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—SC(=NNH$_2$)NH$_2$; $R^{10a}$=OCH$_3$;$R^{10b}$=H Powdered thiosemicarbazide (0.106 g) is added into a stirred solution of the compound resulting from Example 13 (0.94 g) and 2,6-lutidine (0.3 mL) at –78° C. and allowed to warm to room temperature. After stirring at room temperature for 16 hours, the solvent is removed in vacuo, and the product is purified by silica gel chromatography eluting with 5% isopropanol in dichloromethane.

EXAMPLE 66

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—SCH$_2$CO$_2$Et; $R^{10a}$=OCH$_3$; $R^{10b}$=H Ethyl bromoacetate (0.2 mL) is added into a stirred solution of the compound resulting from Example 64 (1 g) and 2,6-lutidine (0.2 g) in acetonitrile under nitrogen at room temperature. After stirring at room temperature for 5 hours, the solvent is removed in vacuo, and the product is purified by silica gel chromatography eluting with 40% acetone in hexane.

EXAMPLE 67

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=4'-pyridylCH$_2$S—; $R^{10a}$=OCH$_3$; $R^{10b}$=H The title compound is prepared from the compound resulting from Example 64, 4-picolyl chloride hydrochloride and 2,6-lutidine in acetonitrile at 60° C. according to the procedure described in Example 66.

EXAMPLE 68

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=3'-pyridylCH$_2$S—; $R^{10a}$=OCH$_3$; $R^{10b}$=H.

The title compound is prepared from the compound resulting from Example 64, 3-picolyl chloride hydrochloride and 2,6-lutidine in acetonitrile at 60° C. according to the procedure described in Example 66.

EXAMPLE 69

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=2'-PyridylCH$_2$S—; $R^{10a}$=OCH$_3$ $R^{10b}$=H The title compound is prepared from the compound resulting from Example 64, 2-picolyl chloride hydrochloride and 2,6-lutidine in acetonitrile at 60° C. according to the procedure described in Example 66.

EXAMPLE 70

Formula II: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—SCH$_2$COCO$_2$Et; $R^{10a}$=OCH$_3$; $R^{10b}$=H The title compound is prepared from the compound resulting from Example 64, ethyl bromopyruvate and 2,6-lutidine in acetonitrile at 60° C. according to the procedure described in Example 66.

EXAMPLE 71

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=-(pyridin-4-on-1-yl); $R^{10a}$=OCH$_3$; $R^{10b}$=H To a solution of the compound resulting from Example 13 (1.01 mmol) and 2,6-lutidine (0.2 mL) in methylene chloride (2 mL) was added 4-hydroxypyridine (0.5132 g) in 2 mL of THF containing 0.5 mL of methanol. The reaction mixture was stirred at room temperature for 36 hours and then chromatographed on silica gel eluting with 50% acetone in hexanes to afford 0.277 g of the title compound. m.p. 126°–131° C. MS (FAB) m/z: M+K=1029.

EXAMPLE 72

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=-(pyridin-2-on-1-yl); $R^{10a}$=OCH$_3$; $R^{10b}$=H To a solution of the compound resulting from Example 13 (924 mg, 0.88 mmol) in 5 mL of THF was added 0.25 mL of 2,6-lutidine followed by 511.2 g of 2-hydroxypyridine (0.5112 g) in dichloromethane-tetrahydrofuran (1:1, 4 mL). The reaction mixture was stirred at room temperature overnight and then chromatographed on silica gel eluting with 50% acetone in hexanes to afford 0.45 g of the title compound. m.p. 101°–106° C. MS (FAB) m/z: M+K=1029.

EXAMPLE 73

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=the ethylene ketal of pyridin-4-on-1yl; $R^{10a}$=OCH$_3$; $R^{10b}$=H A suspension of 4-(hydroxethoxy)pyridine (0.51 g) in 1:1 dichloromethane-tetrahydrofuran (4 mL) is added into a stirred solution of the compound resulting from Example 13 (0.95 g) and 2,6-lutidine (0.2 mL) in dry tetrahydrofuran at room temperature. After stirring at room temperature for 36 hours, the reaction mixture is chromatographed on silica gel eluting with 50% acetone in hexanes to afford the title compound.

EXAMPLE 74

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OCH$_3$; $R_{10a}$=OCH$_3$; $R^{10b}$=H To a solution of the compound resulting from Example 13 (1.21 g, 1.11 mmol) in 5 mL of THF was added 0.25 mL of 2,6-lutidine followed by 0.87 g (6.26 mmol) of 4-(2-hydroxyethyl)pyridine and 0.5 mL of methanol. The reaction mixture was stirred at room temperature under nitrogen overnight and then poured onto a silica gel column and eluted with 35% acetone in hexanes to give partially purified material. This material was rechromatographed on silica gel eluting with 25% acetone in hexanes to afford 462 mg. This material was rechromatographed on silica gel eluting with 1:1 ethyl acetate-hexane to afford 108 mg of pure title compound. m.p. 102°–106° C. MS (FAB) m/z: M+K=966.

EXAMPLE 75

Formula VII: $R^1$=methyl; $R^2$=H; $R^3$=OH; $R^4$ and $R^5$ taken together=O; $R^6$ and $R^7$ taken together=O; X and Y taken together=O; $R^8$=OCH$_2$SCH$_3$; $R^9$=H; $R^{10a}$=OCH$_3$; $R^{10b}$=H To a solution of rapamycin (1.0349 g) in DMSO (3 mL) was added acetic anydride (3 mL) and 0.5 mL methylene chloride. The reaction mixture was stirred one day at room temperature and then partitioned between ether and water. The organic phase was dried over magnesium sulfate and concentrated in vacuo. The residue was purified by silica gel column chromatography eluting with 25% acetone in hexanes to afford partially purified compound which was rechromatographed on silica gel eluting with 2% isopropanol in methylene chloride to give pure title compound (270.7 mg). m.p. 94°–98° C. MS (FAB) m/z: M+K=1012.

EXAMPLE 76

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OCH$_2$SCH$_3$; $R^{10a}$=OCH$_3$; $R^{10b}$=—H The compound resulting from Example 1 (1 g) is dissolved in anhydrous dimethyl sulfoxide (1.5 mL), and the mixture is stirred at room temperature for 14 hours. The reaction mixture is partitioned between ether and water. The organic phase is washed once with brine, dried over magnesium sulfate and solvent removed in vacuo. The product is purified by silica gel chromatography eluting with 40% acetone in hexanes.

EXAMPLE 77

Formula VII: $R^1$=methyl; $R^2$=H; $R^3$=OH; $R^4$ and $R^5$ taken together=O; $R^6$ and $R^7$ taken together=O; X and Y taken together=O; $R^8$=OH; $R^9$=H; $R^{10a}$=—O—n-Butyl; $R^{10b}$=—H Toluenesulfonic acid (0.256 g) was added to a stirred solution of rapamycin (1.13 g) in a solution of methylene chloride (20 mL) and n-butanol (20 mL) at 0° C. After stirring at 0° C. for 2 hours, the reaction mixture was stirred at room temperature overnight. It was partitioned between ether and water. The organic phase was washed once with brine, dried over magnesium sulfate and solvent removed in vacuo. The product was purified by silica gel chromatography eluting with 40% acetone in hexanes to afford 0.41 g of the title compound. MS (FAB)m/z: M+K=994.

EXAMPLE 78

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OH; $R^{10a}$=—O-n-Butyl; $R^{10b}$=H The title compound is prepared from the compound resulting from Example 10, n-butanol and toluenesulfonic acid according to the procedure described in Example 77.

EXAMPLE 79

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OH; $R^{10a}$=—H; $R^{10b}$=OCH$_3$ The title compound is prepared from the compound resulting from Example 10, methanol and toluenesulfonic acid according to the procedure described in Example 77.

EXAMPLE 80

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OH; $R^{10a}$=—H; $R^{10a}$=H.

Triethylsilane (0.2 g) is added to a stirred solution of the compound resulting from Example 10 (1 g) and trifluoroacetic acid (1.2 g) in dichloromethane at −45° C. After being stirred at that temperature for 1 hour, the reaction mixture is partitioned between ether and sodium bicarbonate. The organic phase is washed once with brine, dried over magnesium sulfate and solvent removed in vacuo. The product is purified by silica gel chromatography eluting with 40% acetone in hexanes.

EXAMPLE 81

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OH; $R^{10a}$=-Allyl; $R^{10b}$=H The title compound is prepared from the compound resulting from Example 10, allytrimethylsilane and trifluoroacetic acid according to the procedure described in Example 77.

EXAMPLE 82

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=OH; $R^{10a}$ and $R^{10b}$ taken together=O A solution of the compound resulting from Example 10 (1 g) and DDQ (2 equivalent) is stirred in wet dichloromethane at room temperature overnight. The product is purified by silica gel chromatography eluting with 40% acetone in hexanes.

EXAMPLE 83

Alternate Preparation of Formula IVb: $R^1$=methyl; $R^2$=H; $R^3$=OH; $R^4$ and $R^5$ taken together=O; $R^6$ and $R^7$ taken together=O; X and Y taken together=O; $R^{10a}$=OCH$_3$; $R^{10b}$=H; $R^8$=$R^{18}$=H, $R^9$ and $R^{19}$ taken together form a bond A solution of the compound resulting from Example 58 (1 g) in chloroform is stirred at 50°–60° C. for 4 hours. The product is purified by silica gel chromatography eluting with 40% acetone in hexanes.

EXAMPLE 84

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—O—C(O)—CH$_3$;

The compound resulting from Example 1 is treated with acetic acid and Hünig's base in methylene chloride to afford the title compound.

EXAMPLE 85

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—O—C(O)-phenyl;

The compound resulting from Example 1 is treated with benzoic acid and Hünig's base in methylene chloride to afford the title compound.

EXAMPLE 86

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—O—C(O)-(4-pyridyl);

The compound resulting from Example 1 is treated with isonicotinic acid and Hünig's base in methylene chloride to afford the title compound.

EXAMPLE 87

Formula I: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—O—C(O)—N(OCH$_3$)(CH$_3$);

The title compound is prepared from the compound resulting from Example 11 and N,O-dimethylhydroxylamine according to the procedures described in Example 3.

EXAMPLE 88

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—NH—C(O)-phenyl;

The title compound is prepared from the compound resulting from Example 51 and benzoyl chloride in the presence of N-methylmorpholine in dichloromethane according to the procedure described in Example 52.

EXAMPLE 89

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—NH—C(O)—CH$_2$—CO$_2$H;

The title compound is prepared from the compound resulting from Example 51 and malonyl chloride in the presence of N-methylmorpholine in dichloromethane according to the procedure described in Example 52.

EXAMPLE 90

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—NH—C(O)—(CH$_2$)$_2$—CO$_2$H;

The title compound is prepared from the compound resulting from Example 51 and succinic anhydride in the presence of N-methylmorpholine in dichloromethane according to the procedure described in Example 52.

EXAMPLE 91

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—NH—C(O)—(CH$_2$)$_3$—CO$_2$H;

The title compound is prepared from the compound resulting from Example 51 and glutaric anhydride in the presence of N-methylmorpholine in dichloromethane according to the procedure described in Example 52.

EXAMPLE 92

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=—NH—C(O)—(CH$_2$)$_4$—CO$_2$H;

The title compound is prepared from the compound resulting from Example 51 and adipoyl chloride in the presence of N-methylmorpholine in dichloromethane according to the procedure described in Example 52.

EXAMPLE 93

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=ethylene ketal of pyridin-2-on-1-yl;

The title compound is prepared from the compound resulting from Example 1 and 2-(2'-hydroxyethoxy)pyridine in the presence of N-methylmorpholine in dichloromethane according to the procedure described in Example 72.

EXAMPLE 94

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=ethylene ketal of piperidin-4-on-1-yl The title compound is prepared from the compound resulting from Example 1 and the ethylene ketal of piperidin-4-one in the presence of N-methylmorpholine in dichloromethane according to the procedure described in Example 72.

EXAMPLE 95

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=-(piperidin-4-ol-1-yl)

The title compound is prepared from the compound resulting from Example 1 and 4-hydroxypiperidine in the presence of N-methylmorpholine in dichloromethane according to the procedure described in Example 72.

EXAMPLE 96

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=-(piperidin-4-on-1-yl)

The title compound is prepared from the compound resulting from Example 1 and piperidin-4-one in the presence of N-methylmorpholine in dichloromethane according to the procedure described in Example 72.

EXAMPLE 97

Formula III: $R^1$=methyl; $R^2$=H; $R^3$=OH; $R^4$ and $R^5$ taken together=O; $R^6$ and $R^7$ taken together=O; X and Y taken together=O; $R^8$=H; $R^9$=-(piperidin-2-on-1-yl)

The title compound is prepared from the compound resulting from Example 72 by catalytic hydrogenation in ethanol using a palladium on carbon catalyst.

EXAMPLE 98

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)OC$_2$H$_5$ A solution of rapamycin (304 mg, 0.33 mmol) and ethyl iodoacetate (276 μL, 2.33 mmol) in acetonitrile (300 μL) at 0° C. was treated with Ag$_2$O (308 mg, 1.33 mmol) in small portions over 5 minutes. The reaction was then warmed to ambient temperature and stirred for 5 days. The mixture was adsorbed onto silica gel by dilution of the mixture with CH$_2$Cl$_2$ (5 mL) followed by addition of silica gel (70–230 mesh, 60 A, 5 mL) and solvent evaporation. The adsorbed silica bed was placed on a fresh pad of silica and eluted with mixtures of CH$_2$Cl$_2$:CH$_3$CN (9:1, 4:1, 2:1, 1:1). Fractions containing product were pooled, concentrated and further purified by HPLC on YMC 15 micron spherical 60 A silica, eluting with a mixture of 3:1 hexane:acetone to provide desired product (112 mg). MS (FAB) m/z: M+K=1038. Anal. calc'd. for $C_{55}H_{85}NO_{15}$: C, 66.04; H, 8.56; N, 1.40. Found: C, 65.83; H, 8.51; N, 1.36.

EXAMPLE 99

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)OCH$_2$Ph(4-OMe)

The title compound is prepared using the procedure of Example 98 substituting p-methoxy-benzyl iodoacetate for ethyl iodoacetate.

EXAMPLE 100

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)OH.

The resultant product of Example 99 is treated with dichlorodicyanobenzoquinone in warm benzene. The mixture is concentrated and purified by chromatography on silica gel to provide pure title compound.

EXAMPLE 101

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=OCH$_2$C(O)NR$^{24}$R$^{25}$; $R^{24}$=OCH$_3$; $R^{25}$=benzyl The resultant product of Example 100 (912 mg, 0.94 mmol) is dissolved in THF (3 mL) and cooled to 0° C. before adding N-methylmorpholine (103.4 µL, 0.94 mmol) followed by isobutyl chloroformate (122.2 µL, 0.94 mmol). The resulting suspension is stirred for 20 minutes at 0° C. after which time N-benzyl,O-methyl-hydroxylamine (257 mg, 1.88 mmol) is added, and stirring is continued overnight. The reaction mixture is purified by chromatography on silica gel to provide the title compound.

EXAMPLE 102

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=CH_3$; $R^{25}=$benzyl The title compound is prepared using the procedure of Example 101 and substituting N-methyl-O-benzyl-hydroxylamine for N-benzyl-O-methylhydroxylamine.

EXAMPLE 103

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NHOCH_3$ The title compound is prepared using the procedure of Example 101 and substituting O-methyl-hydroxylamine for N-benzyl-O-methyl-hydroxylamine.

EXAMPLE 104

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=OCH_3$; $R^{25}=CH_3$ The title compound is prepared using the procedure of Example 101 and substituting N-methyl-O-methyl-hydroxylamine for N-benzyl-O-methyl-hydroxylamine.

EXAMPLE 105

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=H$; $R^{25}=$cyclopropyl The title compound is prepared using the procedure of Example 101 and substituting cyclopropylamine for N-benzyl-O-methyl-hydroxylamine.

EXAMPLE 106

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=OCH_3$; $R^{25}=$cyclopropyl The title compound is prepared using the procedure of Example 101 and substituting N-cyclopropyl-O-methyl-hydroxylamine for N-benzyl-O-methylhydroxylamine.

EXAMPLE 107

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=OCH_3$; $R^{25}=$cyclohexyl The title compound is prepared using the procedure of Example 101 and substituting N-cyclohexyl-O-methyl-hydroxylamine for N-benzyl-O-methylhydroxylamine.

EXAMPLE 108

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=OCH_3$; $R^{25}=CH_2CH_2OH$.

The title compound is prepared using the procedure of Example 101 and substituting N-(2-hydroxyethyl)-O-methyl-hydroxylamine for N-benzyl-O-methyl-hydroxylamine.

EXAMPLE 109

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=H$; $R^{25}=CH_2CO_2CH_2Ph(4-OMe)$.

The title compound is prepared using the procedure of Example 101 and substituting glycine p-methoxybenzyl ester for N-benzyl-O-methylhydroxylamine.

EXAMPLE 110

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=H$; $R^{25}=CH_2CO_2H$ The title compound is prepared by the procedure described in Example 100 substituting the product from Example 109 for the product from Example 99.

EXAMPLE 111

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=H$; $R^{25}=$3-biphenylyl The title compound is prepared using the procedure of Example 101 and substituting 3-biphenylamine for N-benzyl-O-methyl-hydroxylamine.

EXAMPLE 112

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=CH_2CH_2OH$; $R^{25}=$3-biphenylyl The title compound is prepared using the procedure of Example 101 and substituting N,N-(ethanol-2-yl)-(3-biphenyl)-amine for N-benzyl-O-methyl-hydroxylamine.

EXAMPLE 113

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=CH_2CH_2N(CH_3)(CH_2CH_2OH)$; $R^{25}=$phenyl The title compound is prepared using the procedure of Example 101 and substituting N-phenyl-N'-methyl-N'-(ethanol-2-yl)-ethyldiamine for N-benzyl-O-methyl-hydroxylamine.

EXAMPLE 114

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=OCH_2C(O)NR^{24}R^{25}$; $R^{24}=CH_2CH_2N(CH_3)_2$; $R^{25}=$phenyl The title compound is prepared using the procedure of Example 101 and substituting N-phenyl-N',N'-dimethyl-ethyldiamine for N-benzyl-O-methylhydroxylamine.

EXAMPLE 115

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=CH_2(3$-pyridyl); $R^{25}=CH_2(3$-pyridyl); $R^{25}=CH_2(3$-pyridyl)

The title compound is prepared using the procedure of Example 101 and substituting substituting 3,3'-dipipicolylamine for N-benzyl-O-methylhydroxylamine.

EXAMPLE 116

Formula VII: $R^1=Ch_3$; $R^2=R^9=H$; $R^3=OH$; $R^4$ and $R^5$ taken together=O; $R^6$ and $R^7$ taken together=O; X and Y taken together=O; $R^8=-OCH_2C(O)NH$-(4-morpholinyl)

The compound resulting from Example 100 is activated as in Example 101 and then treated with 1 equivalent of 4-aminomorpholine and 0.1 equivalents of 4-dimethylaminopyridine instead of N-benzyl-O-methyl-hydroxylamineto give the title compound.

EXAMPLE 117

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; where $R^{24}$ and $R^{25}$ taken together=$-CH_2CH_2SCH_2CH_2-$, thus forming a six membered ring incorporating the nitrogen to which they are attached The compound resulting from Example 100 is activated as in Example 101 and then treated with thiomorpholine instead of N-benzyl-O-methyl-hydroxylamine to give the title compound.

EXAMPLE 118

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=4$-$CF_3$-phenyl The compound resulting from Example 100 is activated as in Example 101 and then treated with 4-aminobenzotrifluoride instead of N-benzyl-O-methyl-hydroxylamineto give the title compound.

EXAMPLE 119

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=4$-F-phenyl The compound resulting from Example 100 is activated as in Example 101 and then treated with 4-fluoroaniline instead of N-benzyl-O-methylhydroxylamine to give the title compound.

EXAMPLE 120

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=4$-(4-morpholino)-phenyl The compound resulting from Example 100 is activated as in Example 101 and then treated with 4-morpholinoaniline instead of N-benzyl-O-methyl-hydroxylamine to give the title compound.

EXAMPLE 121

Formula VII: $R^1=CH_3$; $R^2=R^9=H$; $R^3=OH$; $R^4$ and $R^5$ taken together=O; $R^5$ and $R^7$ taken together=O; X and Y taken together=O; $R^8=-OCH_2C(O)NR^{24}R^{25}$; $R^{24}=H$; $R^{25}=4$-HO-phenyl The compound resulting from Example 100 is activated as in Example 101 and then treated with p-aminophenol instead of N-benzyl-O-methyl-hydroxylamine to give the title compound.

EXAMPLE 122

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=3$-pyridyl The compound resulting from Example 100 is activated as in Example 101 and then treated with 3-aminopyridine instead of N-benzyl-O-methyl-hydroxylamine to give the title compound.

EXAMPLE 123

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=4$-pyridyl The compound resulting from Example 100 is activated as in Example 101 and then treated with 4-aminopyridine instead of N-benzyl,O-methyl-hydroxylamine to give the title compound.

EXAMPLE 124

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R^{25}=2$-pyridyl The compound resulting from Example 100 is activated as in Example 101 and then treated with 2-aminopyridine instead of N-benzyl-O-methyl-hydroxylamine to give the title compound.

EXAMPLE 125

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)NR^{24}R^{25}$; $R^{24}=H$; $R_{25}=NHCO_2CH_3$ The compound resulting from Example 100 is activated as in Example 101 and then treated with methylcarbazate instead of N-benzyl-O-methyl-hydroxylamine to give the title compound.

EXAMPLE 126

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O$-(L-prolinecarboxamide)

The compound resulting from Example 100 is activated as in Example 101 and then treated with L-prolinecarboxamide instead of N-benzyl-O-methyl-hydroxylamineto give the title compound.

EXAMPLE 127

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=-OCH_2C(O)$—(D-prolinecarboxamide)

The compound resulting from Example 100 is activated as in Example 101 and then treated with D-Prolinecarboxamide instead of N-benzyl-O-methyl-hydroxylamineto give the title compound.

EXAMPLE 128

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)$—(L-prolinol).

The compound resulting from Example 100 is activated as in Example 101 and then treated with L-prolinol instead of N-benzyl-O-methyl-hydroxylamineto give the title compound.

EXAMPLE 129

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)$—(D-prolinol)

The compound resulting from Example 100 is activated as in Example 101 and then treated with D-prolinol instead of N-benzyl-O-methyl-hydroxylamineto give the title compound.

EXAMPLE 130

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)N(CH_2CH_2OH)NH(CO_2CH_3)$ The compound resulting from Example 100 is activated as in Example 101 and then treated with N-(ethanol-2-yl)-N'-carbomethoxy-hydrazine instead of N-benzyl-O-methyl-hydroxylamine to give the title compound.

EXAMPLE 131

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=H$; $R^{25}=$3-(phenylethynyl)phenyl The compound resulting from Example 100 is activated as in Example 101 and then treated with 3-phenylethynylaniline instead of N-benzyl-O-methyl-hydroxylamineto give the title compound.

EXAMPLE 132

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=CH_2CH_2CH_2OH$; $R^{25}=$4-fluorophenyl The compound resulting from Example 100 is activated as in Example 101 and then treated with (4-fluoroanilino)-1-propanol instead of N-benzyl-O-methyl-hydroxylamineto give the title compound.

EXAMPLE 133

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=CH_2CH_2CH_2OCOCH_2CH_2CO_2H$; $R^{25}=$4-fluorophenyl.

The compound resulting from Example 132 is treated with succinic anhydride, by the procedure described in Tetrahedron Letters, 30: 5045–48 (1989), to give the title compound.

EXAMPLE 134

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$, $R^{24}$ and $R^{25}$ are taken together as the following diradical, —$CH_2CH_2C(OCH_2CH_2O)CH_2CH_2$—

The compound resulting from Example 100 is activated as in Example 101 and then treated with 1,4-dioxa-8-azaspiro[4.5]decane instead of N-benzyl--methyl-hydroxylamineto give the title compound.

EXAMPLE 135

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NHNH$—CO—(4-pyridyl)

The compound resulting from Example 100 is activated as in Example 101 and then treated with isonicotinic acid hydrazide instead of N-benzyl-O-methyl-hydroxylamineto give the title compound.

EXAMPLE 136

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=H$; $R^{25}=$3-fluorophenyl The compound resulting from Example 100 is activated as in Example 101 and then treated with m-fluoroaniline instead of N-benzyl-O-methyl-hydroxylamine to give the title compound.

EXAMPLE 137

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=H$; $R^{25}=$3-hydroxy-phenyl The compound resulting from Example 100 is activated as in Example 101 and then treated with m-aminophenol instead of N-benzyl-O-methyl-hydroxylamineto give the title compound.

EXAMPLE 138

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$, $R^{24}$ and $R^{25}$ are taken together as the following diradical: —$CH_2CH_2$—$N(CH_3)$—$CH_2CH_2$—.

The compound resulting from Example 100 is activated as in Example 101 and then treated with N-methylpiperazine instead of N-benzyl-O-methyl-hydroxylamine to give the title compound.

EXAMPLE 139

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=H$; $R^{25}=$1,4-benzodioxan-6-yl The compound resulting from Example 100 is activated as in Example 101 and then treated with 1,4-benzodioxan-6-amine instead of N-benzyl-O-methyl-hydroxylamine to give the title compound.

EXAMPLE 140

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=1,3-benzodioxol-5-yl The compound resulting from Example 100 is activated as in Example 101 and then treated with 3,4-(methylenedioxy)-aniline instead of N-benzyl-O-methyl-hydroxylamine to give the title compound.

EXAMPLE 141

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=1-naphthalenyl The compound resulting from Example 100 is activated as in Example 101 and then treated with 1-naphthylamine instead of N-benzyl-O-methyl-hydroxylamine to give the title compound.

EXAMPLE 142

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$ =—$OCH_2C(O)$- (1-pyrrolidinyl)

The compound resulting from Example 100 is activated as in Example 101 and then treated with pyrrolidine instead of N-benzyl-O-methyl-hydroxylamine to provide the title compound.

EXAMPLE 143

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)$—(1-piperidinyl)

The compound resulting from Example 100 is activated as in Example 101 and then treated with piperidine instead of N-benzyl-O-methyl-hydroxylamine to provide the title compound.

EXAMPLE 144

Formula VII: $R^1$=$CH_3$ ; $R^2$=$R^9$=H; $R^3$=OH; $R^4$ and $R^5$ taken together=O; $R^6$ and $R^7$ taken together=O; X and Y taken together=O; $R^8$=—$OCH_2C(O)OCH_2$-(9-fuorenyl)

Rapamycin (11.0 g, 0.012 mmol) is dissolved in distilled $CH_2Cl_2$ (50 mL). Rhodium (II) acetate dimer (100 mg) is added and the mixture cooled to 0° C. 9-Fluorenylmethyl diazoacetate (3.35 g, 0.012 mol) is dissolved in $CH_2Cl_2$ (10 mL) and the solution added to the reaction via syringe pump at a rate of approximately 0.5 mL/hour. Addition is complete in approximately 24 hours. The reaction is stirred at 0° C. for an additional 24 hours then loaded onto silica (230–400 mesh, 400 g) and the solvent evaporated by airflow in the hood. The adsorbed silica is layered over fresh silica (800 g) in a 1 L fritted glass funnel and eluted with mixtures of $CH_2Cl_2$ and $CH_3CN$. Fractions containing product are combined and concentrated to provide title compound.

EXAMPLE 145

Alternate Preparation of Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)OH$ The resultant product of Example 144 is dissolved in $CH_2Cl_2$, whereupon piperidine is added. The solution is stirred at room temperature for 2 hours then transferred to a separatory funnel, diluted with additional $CH_2Cl_2$ (100 mL), then washed with 1N HCl(2×100 mL) and brine (2×100 mL). The organic layer is dried ($Na_2SO_4$), filtered, and the solvent removed in vacuo to give crude title compound with is purified by chromatography on silica gel.

EXAMPLE 146

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$CH_2CH_2C_6H_5$ The compound resulting from Example 145 is dissolved in dichloromethane and the solution cooled to 0° C. $HOBT.H_2O$ is added followed by EDAC then phenethylamine. The reaction is warmed to room temperature and stirred overnight. Dichloromethane is added and the organic phase washed with 1N HCl, saturated sodium bicarbonate solution, and then brine. The organic layer is dried ($Na_2SO_4$), filtered, and solvent removed in vacuo to give crude product. This is purified by HPLC (20×300 mm silica column) eluting with 3:1 hexane-acetone. Fractions containing product are combined and solvent removed in vacuo to give the title compound.

EXAMPLE 147

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=$OCH_3$; $R^{25}$=—$CH_2CH_2C_6H_5$ The title compound is prepared using the procedures described in Example 146 and substituting N,N-methyloxy, 2-phenylethyl amine for 2-phenylethylamine.

EXAMPLE 148

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NH(CH_2)_5NH$-dansyl The title compound is prepared using the procedures described in Example 146 and substituting dansyl cadaverine for 2-phenylethylamine.

EXAMPLE 149

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$C_6H_5$ The title compound is prepared using the procedures described in Example 146 and substituting aniline for 2-phenylethylamine.

EXAMPLE 150

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$ =—$OCH_2C(O)NH(CH_2)_2N(CH_2CH_2)_2O$ The title compound is synthesized in the manner described for Example 101 substituting 2-(4-morpholino)-ethylamine for N-benzyl-O-methyl-hydroxylamine.

EXAMPLE 151

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NH(CH_2)_3N(CH_2CH_2)_2O$ The title compound is prepared using the procedures described in Example 146 and substituting 3-(4-morpholino)-propylamine for 2-phenylethylamine.

EXAMPLE 152

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NH(CH_2)_2N(CH_3)_2$ The title compound is synthesized in the manner described for Example 101 substituting 2-dimethylaminoethylamine for N-benzyl-O-methyl-hydroxylamine.

EXAMPLE 153

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$(CH_2)_3N(CH_3)_2$ The title compound is prepared using the procedures described in Example 146 and substituting 3-dimethylamino-propylamine for 2-phenylethylamine.

EXAMPLE 154

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$ —$OCH_2C(O)$—[(S)—$HNCH(CH_2C_6H_5)CO_2CH_2ph(4-OMe)]$ The title compound is prepared using the procedures described in Example 146 and substituting L-phenylalanine p-methoxybenzylester for 2-phenylethylamine.

EXAMPLE 155

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)$—[(S)—$HNCH(CH_2C_6H_5)CO_2H]$ The title compound is synthesized in the manner described in Example 100 substituting the product from Example 154 for the product from Example 99.

EXAMPLE 156

Formula VII: $R^1$=$CH_3$; $R^2$=$R^9$=H; $R^3$=OH; $R^4$ and $R^5$ taken together=O: $R^6$ and $R^7$ taken together=O; X and Y taken together=O; $R^8$=—$OCH_2C(O)$—[(R)—$HNCH(CH_2C_6H_5)CO_2CH_2Ph(4-OMe)]$ The title compound is synthesized in the manner described for Example 146 substituting D-phenylalanine p-methoxybenzylester for 2-phenylethylamine.

EXAMPLE 157

Formula VII: $R^1$=$CH_3$; $R^2$=$R^9$=H; $R^3$=OH; $R^4$ and $R^5$ taken together=O: $R^6$ and $R^7$ taken together=O; X and Y taken together=O; $R^8$=—$OCH_2C(O)$—[(R)—$HNCH(CH_2C_6H_5)CO_2H]$ The title compound is synthesized in the manner described in Example 100 substituting the product from Example 156 for the product from Example 99.

EXAMPLE 158

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$(CH_2)_2SH$ The product of Example 100 (1.4 g, 1.4 mmol) is dissolved in THF (4.5 mL) and the solution cooled to 0° C. before adding N-methylmorpholine (155.1 µL, 1.4 mmol) followed by isobutyl chloroformate (122.2 µL, 1.4 mmol). The resulting suspension is stirred for 20 minutes at 0° C. then 2-aminoethanethiol hydrochloride (320.8 mg, 2.8 mmol) is added. The mixture is stirred for 3 hours at room temperature before addition of more N-methylmorpholine (387.8 µL, 3.5 mmol). The reaction is stirred overnight, loaded onto silica (40 mL) in a fritted funnel, then eluted with dichloromethane (100 mL), 1:1 hexane/acetone (200 mL), followed by acetone (100 mL). Fractions containing product are combined and solvent removed in vacuo to give crude product. This material is further purified by HPLC (30×300 mm silica column) eluting with 2:1 hexane/acetone to provide the title compound.

EXAMPLE 159

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$(CH_2)_3SH$ The title compound is synthesized in the manner described for Example 158 substituting 3-amino-propanethiol for 2-aminoethanethiol.

EXAMPLE 160

Formula VII: $R^1$=$CH_3$; $R^2$=$R^9$=H; $R^3$=OH; $R^4$ and $R^5$ taken together=O: $R^6$ and $R^7$ taken together=O; X and Y taken together=O; $R^8$=—$OCH_2C(O)O(t-butyl)$ Silver (I) oxide (926 mg, 4.0 mmol) is added to rapamycin (791 mg, 1.0 mmol) dissolved in acetonitrile (0.8 mL) and t-butyl iodoacetate (828 µL, 7.0 mmol). The mixture is stirred at room temperature for 5 days, volatiles are removed in vacuo. The product is isolated by chromatography on silica gel as described in Example 98.

EXAMPLE 161

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=2-naphthyl The compound resulting from Example 100 is activated by the procedure described in Example 101 and then treated with 2-naphthylamine instead of N-benzyl-O-methyl-hydroxylamine to give the title compound.

EXAMPLE 162

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=4-($H_2NSO_2$)phenyl The compound resulting from Example 100 is activated by the procedure described in Example 101 and then treated with sulfanilamide instead of N-benzyl-O-methyl-hydroxylamine to give the title compound.

EXAMPLE 163

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)$-(4-(2-hydroxyethyl)piperzin-1-yl)

The compound resulting from Example 100 is activated by the procedure described in Example 101 and then treated with N-(2-hydroxyethyl)-piperazine instead of N-benzyl-O-methyl-hydroxylamine to give the title compound.

EXAMPLE 164

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=$CH_3$; $R^{25}$-phenyl The compound resulting from Example 100 is activated by the procedure described in Example 101 and then treated with N-methylaniline instead of N-benzyl-O-methyl-hydroxylamine to give the title compound.

EXAMPLE 165

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=$R^{25}$=—$CH_2CH_2OH$ The compound resulting from Example 100 is activated by the procedure described in Example 101 and then treated with N,N-bis-(2-hydroxyethyl)-amine instead of N-benzyl-O-methyl-hydroxylamine to give the title compound.

EXAMPLE 166

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=$CH_3 R^{25}$=—$CH_2CH_2CH_2N(CH_3)_2$ The compound resulting from Example 100 is activated by the procedure described in Example 101 and then treated with N,N'-methyl-(3-dimethylaminopropyl)-amine instead of N-benzyl-O-methyl-hydroxylamine to give the title compound.

EXAMPLE 167

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=phenyl $R^{25}$=—$CH_2CH_2CH_2OH$ The compound resulting from Example 100 is activated by the procedure described in Example 101 and then treated with N,N-phenyl-(3-hydroxypropyl)-amine instead of N-benzyl-O-methyl-hydroxylamine to give the title compound.

EXAMPLE 168

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=—$CH(CH_2OH)_2$ The compound resulting from Example 100 is activated by the procedure described in Example 101 and then treated with serinol instead of N-benzyl-O- methyl-hydroxylamine to give the title compound.

EXAMPLE 169

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=H; $R^{25}$=3-($CF_3$)-phenyl The compound resulting from Example 100 is activated by the procedure described in Example 101 and then treated with 3-trifluoromethylaniline instead of N-benzyl-O-methyl-hydroxylamine to give the title compound.

EXAMPLE 170

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)NR^{24}R^{25}$; $R^{24}$=$R^{25}$=—$CH_2CN$ The compound resulting from Example 100 is activated by the procedure described in Example 101 and then treated with iminodiacetonitrile instead of N-benzyl-O-methyl-hydroxylamine to give the title compound.

EXAMPLE 171

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2C(O)$-(1-aziridinyl)

The compound resulting from Example 100 is activated by the procedure described in Example 101 and then treated with aziridine instead of N-benzyl-O-methyl-hydroxylamine to give the title compound.

EXAMPLE 172

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2NHC(O)$-(4-morpholinyl)

The compound resulting from Example 100 (564 mg, 0.58 mmol) in THF (6 mL) is stirred together with N-methylpiperidine (73 μL, 0.58 mmol) and diphenylphosphorylazide (73 μL, 0.58 mmol) at ambient temperature for 5 minutes, then at reflux for 3 hours. The stirring solution is cooled to ambient temperature and treated with morpholine (157 μL, 1.8 mmol). The mixture is purified by HPLC on a column 20×300 mm (YMC 15 u, 60 Å spherical $SiO_2$) eluting with a step gradient of hexane:acetone (1:1) then hexane:acetone (2:3), to provide title compound.

EXAMPLE 173

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2NHC(O)NR^{24}R^{25}$; $R^{24}$=H; $R^{25}$=phenyl The compound resulting from Example 100 is activated as in Example 172 and then treated with aniline instead of morpholine to give the title compound.

EXAMPLE 174

Formula VII: $R^1$=$CH_3$; $R^2$=$R^9$=H; $R^3$=OH; $R^4$ and $R^5$ taken together=O; $R^6$ and $R^7$ taken together=O; X and Y taken together=O; $R^8$=—$OCH_2NHC(O)$-phenyl The compound resulting from Example 100 is activated as in Example 172 and then treated with benzoic acid instead of morpholine, whereupon the mixture is heated. Purification by chromatography on silica gel provides the title compound.

EXAMPLE 175

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$NHC(O)NR$^{24}$R$^{25}$; $R^{24}$=H; $R^{25}$=—CH$_2$CH$_2$CH$_2$OH The compound resulting from Example 100 is activated as in Example 172 and then treated with 3-aminopropanol instead of morpholine to give the title compound.

EXAMPLE 176

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$; $R^{24}$=H; $R^{25}$=6-carbomethoxymethylmercaptopurine hydrazid-yl The compound resulting from Example 100 is activated as in Example 101 and then treated with 6-carbomethoxymethylmercaptopurine hydrazide instead of N-benzyl-O-methyl-hydroxylamine to give the title compound.

EXAMPLE 177

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$, $R^{24}$ and $R^{25}$ are taken together as the following diradical: —CH$_2$CH$_2$SO$_2$CH$_2$CH$_2$—

The compound resulting from Example 100 is activated as in Example 101 and then treated with thiomorpholine sulfone instead of N-benzyl-O-methyl-hydroxylamine to give the title compound,

EXAMPLE 178

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$; $R^{24}$=H; $R^{25}$=CH$_2$CH$_2$-(4-F-phenyl)

The compound resulting from Example 100 is activated as in Example 101 and then treated with 4-fluorophenethylamine instead of N-benzyl-O-methyl-hydroxylamine to give the title compound,

EXAMPLE 179

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$; $R^{24}$=H; $R^{25}$=4-Cl-phenyl The compound resulting from Example 100 is activated as in Example 101 and then treated with 4-chloroaniline instead of N-benzyl-O-methyl-hydroxylamine to give the title compound

EXAMPLE 180

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$; $R^{24}$=H; $R^{25}$=4-(OCH$_3$)-phenyl The compound resulting from Example 100 is activated as in Example 101 and then treated with 4-methoxyaniline instead of N-benzyl-O-methyl-hydroxylamine to give the title compound.

EXAMPLE 181

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)NR$^{24}$R$^{25}$; $R^{24}$=H; $R^{25}$=3-I-phenyl The compound resulting from Example 100 is activated as in Example 101 and then treated with 3-iodoaniline instead of N-benzyl-O-methyl-hydroxylamine to give the title compound.

EXAMPLE 182

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)O—CH$_2$-[(1R)-(+)-alpha-pinen-10-yl)]

(a) A three-neck 2 L roundbottom flask equipped with an overhead stirrer was charged with diethylether (800 mL), chloroacetyl chloride (40 mL, 0.5 mol) and (1R)-(−)-nopol (85.3 mL, 0.5 mol). At 0° C., triethylamine (69.5 mL, 0.5 mol) was added dropwise over 15 minutes. After stirring at 0° C. for 1 hour, the mixture was warmed to ambient temperature and stirred for 18 hours. The mixture was vacuum filtered through a Buchner funnel and the white cake was extracted with ether (2×200 mL). The filtrates were then washed sequentially with 0.5.N HCl(500 mL), water (500 mL) and brine (500 mL). After drying the organics (Na$_2$SO$_4$), the mixture was filtered and concentrated to a pale tan oil (104 g). The resultant nopol chloroacetate was sufficiently pure to carry forward in the next step.

(b) Sodium Iodide (20.1 g, 134 mmol) was refluxed in acetone (55 mL) for 5 minutes and cooled to room temperature. Nopol chloroacetate from step (a) (5.85 g, 24.17 mmol) was added, and the reaction was stirred for 30 minutes. The solvent was removed in vacuo, and the resulting slurry was partitioned between water (30 mL) and ethyl acetate (20 mL). The aqueous portion was extracted with additional ethyl acetate (20 mL). The combined organics were washed sequentially with saturated sodium bicarbonate (30 mL) and 10% sodium bisulfite (30 mL), dried (sodium sulfate) and concentrated in vacuo to an amber oil (7 g). The resulting nopol iodoacetate was sufficiently pure to use in the next step.

(c) Rapamycin (2.9 g, 3.16 mmol) and nopol iodoacetate from step (b) (5.70 g, 17.1 mmol, 5.4 eq) are dissolved in acetonitrile (1.5 mL). After a homogeneous solution is obtained, it is cooled to 0° C. and silver(I) oxide (3.13 g, 13.4 mmol) is added portionwise (15 minutes). The solution is brought to room temperature by gradual melting of the ice and is stirred for 5 days. The reaction is diluted in diethyl ether and poured onto silica gel (70–230 mesh, 20 mL) and allowed to air dry. The adsorbed silica is layered on fresh silica (70–230 mesh, 100 mL) and eluted with methylene chloride (150 mL); methylene chloride:acetonitrile (9:1,450 mL); (3:1,300 mL); (1:1,200 mL); acetone (200 mL). 50 mL fractions are collected. Fractions containing product are pooled, concentrated, further purification by HPLC on silica eluting with 3:1 hexane:acetone provides pure title compound.

EXAMPLE 183

Formula VII: $R^1$=CH$_3$; $R^2$=$R^9$=H; $R^3$=OH; $R^4$ and $R^5$ taken together=O; $R^6$ and $R^7$ taken together=O; X and Y taken together=O; $R^8$=—OCH$_2$C(O)O—CH$_2$-[4-nitrophenyl]

(a) A three-neck 2 L roundbottom flask equipped with an overhead stirrer was charged with diethylether (800 mL), chloroacetyl chloride (40 mL, 0.5 mol) and 4-nitrobenzylalcohol (76.5 g, 0.5 mol) and cooled to 0° C. Triethylamine (69.5 mL, 0.5 mol) was added dropwise over 15 minutes. After stirring at 0° C. for 1 hour, the mixture was warmed to ambient temperature and stirred for 18 hours. The mixture was vacuum filtered through a Buchner funnel and the white cake was extracted with ether (2×200 mL). The filtrates were then washed sequentially with 0.5N HCl(500 mL), water (500 mL) and brine (500 mL). After drying the organics ($Na_2SO_4$), the mixture was filtered and concentrated to a pale tan solid (74.8 g). The crude product was recrystallized from diethylether. m.p. 71°–72° C.

(b) Sodium Iodide (39.5 g, 260 mmol) was refluxed in acetone (104 mL) for 3 minutes and cooled to room temperature. 4-Nitrobenzyl chloroacetate from step (a) (10.7 g, 47 mmol) was added, and the reaction was stirred for 30 minutes. The solvent was removed in vacuo, and the resulting slurry was partitioned between water (50 mL) and ethyl acetate (50 mL). The aqueous phase was extracted with additional ethyl acetate (50 mL), and the combined organics were washed sequentially with saturated sodium bisulfite (2×50 mL) and brine (50 mL). The organics were dried (sodium sulfate) and concentrated in vacuo to pure product (15.6 g).

(c) Rapamycin (5.8 g, 6.3 mmol) and 4-nitrobenzyl iodoacetate from step (b) (15.6 g, 48.6 mmol, 7.7 eq) are dissolved in acetonitrile (2.5 mL). After a homogeneous solution is obtained, it is cooled to 0° C. and silver(I) oxide (5.9 g, 25.6 mmol) is added portionwise (15 minutes). The solution is brought to room temperature by gradual melting of the ice and is stirred for 5 days. The reaction is diluted in diethyl ether (25 mL), poured onto silica gel (70–230 mesh, 40 mL) and allowed to air dry. The adsorbed silica is layered on fresh silica (70–230 mesh, 200 mL) and eluted with methylene chloride (500 mL); methylene chloride:acetonitrile (9:1,400 mL); (6:1,300 mL); (3:1, 1000 mL); (1:1,500 mL); (1:2,300 mL). 100 mL fractions are collected. Fractions containing desired product ($CH_2Cl_2:CH_3CN$ 3:1) are pooled and concentrated in vacuo to provide the title compound.

EXAMPLE 184

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8=$—$OCH_2C(O)NR^{24}R^{25}$; $R^{24}=$—$(CH_2)_2N(CH_2CH_2)_2O$; $R^{25}=$—$CH_2CH_2OH$ The title compound is synthesized by the procedures described in Example 101 substituting N,N-[2-hydroxyethyl][2-(4-morpholino)-ethyl]amine for N-benzyl-O-methyl-hydroxylamine.

EXAMPLE 185

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8$=2,3,4,6-tetra-O-acetyl-beta-D-glucopyranosyloxy Alpha-D-glucopyranosyl bromide tetraacetate (2.46 g, 6 mmol) and rapamycin (913 mg, 1.0 mmol) in acetonitrile (1 mL) at 0° C. is treated with $Ag_2O$ (928 mg, 4 mmol). The mixture is warmed to ambient temperature and stirred for 5 days. Purification of the mixture by chromatography on silica gel provides the title product.

EXAMPLE 186

Formula VII: $R^1=CH_3$; $R^2=R^9=H$; $R^3=OH$; $R^4$ and $R^5$ taken together=O; $R^6$ and $R^7$ taken together=O; X and Y taken together=O; $R^8$=2,3,4,6-tetra-O-acetyl-beta-D-glucopyranosyloxy Alpha-D-glucopyranosyl bromide tetraacetate (1.23 g, 3 mmol), rapamycin (913 mg, 1.0 mmol) and crushed 4 Å molecular sieves (2 g) in anhydrous methylene chloride (150 mL) at −78° C. is treated with $AgCO_3$ (1.7 g, 10 mmol) followed by $Ag(OSO_2CF_3)$ (257 mg, 1.0 mmol). The mixture is warmed to ambient temperature over 8 hours and is stirred for an additional 5 hours. Purification of the mixture by chromatography on silica gel provides title product.

EXAMPLE 187

Formula VII: $R^1=CH_3$; $R^2=R^8=H$; $R^3=OH$; $R^4$ and $R^5$ taken together=O; $R^6$ and $R^7$ taken together=O; X and Y taken together=O; $R^8$ —$OCH_2C(O)OCH_2CCl_3$ The title compound is prepared using the procedures described in Example 183 substituting 2,2,2-trichloroethanol for p-nitrobenzylalcohol.

EXAMPLE 188

In vitro Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6 (1987).

The results of the assay, shown below in Table 1, demonstrate that the compounds tested are effective immunomodulators at nanomolar concentrations.

TABLE 1

| Mixed Leukocyte Response (MLR) | |
|---|---|
| Example | $IC_{50}$ (nM) |
| 3 | 0.13 |
| 10 | 0.03 |
| 17 | 0.15 |
| 38 | 0.03 |
| 50 | 0.96 |
| 39 | 0.14 |
| 71 | 0.12 |
| 72 | 0.99 |
| 74 | 1.81 |

The compounds of the invention, including but not limited to those specified in the examples, possess immunomodulatory activity in mammals (especially humans). As immunosuppressants, the compounds of the present invention are useful for the treatment and prevention of immune-mediated diseases such as the resistance by transplantation of organs or tissue such as heart, kidney, liver, small-bowel, and the like; grat-versus-host diseases; autoimmune diseases, such as rheumatoid arthritis, thyroiditis, multiple sclerosis, myasthenia gravis, type I diabetes, uveitis, allergic encephalomyelitis, glomerulonephritis, and the like. Further uses include the treatment and prophylaxis of inflammatory and hyperproliferative skin diseases and cutaneous manifestations of immunologically-mediated illnesses, such as psoriasis, atopical dermatitis, and Epidermolysis bullosa. Further instances where a compound of the invention would be useful include various eye diseases (autoimmune and otherwise) such as ocular pemphigus, Scleritis, and Graves' opthalmopathy, etc.

Other treatable conditions would include but are not limited to intestinal inflammations/allergies such as Crohn's disease and ulcerative colitis; renal diseases such as interstitial nephritis; skin diseases such as dermatomyositis;

hematic diseases such as aplastic anemia, idiopathic thrombocytopenic purpura, and autoimmune hemolytic anemia; circulatory diseases such as myocardosis, arteriosclerosis, and atherosclerosis; collagen diseases such as Wegener's granuloma; nephrotic syndrome such as glomerulonephritis; Pyoderma; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis).

When used in the above or other treatments, a therapeutically effective amount of one of the compounds of the present invention may be employed in pure form or, where such forms exist, in pharmaceutically acceptable salt, ester or prodrug form. Alternatively, the compound may be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drags used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. The phrase "pharmaceutically acceptable carrier" means a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carder comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A pharmaceutical composition for immunomodulatory treatment comprising a compound having the formula:

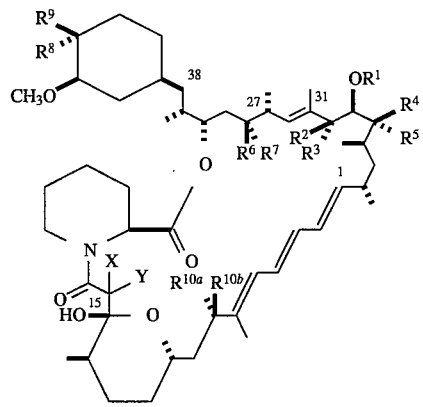

or a pharmaceutically acceptable salt, ester, amide or prodrug thereof wherein $R^1$ is hydrogen, a hydroxy protecting group, $C_1$–$C_{10}$-loweralkyl or phenyl-substituted $C_1$–$C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1$–$C_{10}$ loweralkyl and $R^5$ is hydroxy or protected hydroxy or $R^5$ is hydrogen or phenyl-substituted $C_1$–$C_{10}$-loweralkyl and $R^4$ is hydroxy or protected hydroxy or $R^4$ and $R^5$ taken together are oxo;

$R^6$ is hydrogen or phenyl-substituted $C_1$–$C_{10}$-loweralkyl and $R^7$ is hydrogen, hydroxy or protected hydroxy or $R^7$ is hydrogen or phenyl-substituted $C_1$–$C_{10}$-loweralkyl and $R^6$ is hydroxy or protected hydroxy or $R^6$ and $R^7$ taken together are (1) oxo,
(2) diazo,
(3) =$CH_2$
(4) —O—$(CH_2)_2$—O—,
(5) —S—$(CH_2)_2$—S—,
(6) —O—$(CH_2)_3$—O—,
(7) —S—$(CH_2)_3$—S—,
(8) =N—$OR^{20}$ wherein $R^{20}$ is hydrogen, $C_1$–$C_{10}$-loweralkyl, $C_2$–$C_{10}$-alkenyl, $C_3$–$C_{10}$-cycloalkyl, $C_3$–$C_{10}$-cycloalkenyl, $C_3$–$C_{10}$-bicycloalkenyl, aryl, aryl-$C_1$–$C_{10}$-alkyl, heterocyclic or heterocyclic-$C_1$–$C_{10}$-alkyl, each of which is optionally substituted with $C_1$–$C_{10}$-loweralkyl, halogen, hydroxy, aryl or heterocyclic; or
(9) =N—N($R^{21}$)($R^{22}$) wherein $R^{21}$ and $R^{22}$ are independently selected from hydrogen, $C_1$–$C_{10}$-loweralkyl, aryl, aryl-$C_1$–$C_{10}$-alkyl, heterocyclic and heterocyclic-$C_1$–$C_{10}$-alkyl;

$R^8$ is hydrogen;

$R^9$ is (1) —OS(O)$_2$CF$_3$,
(2) —OS(O)$_2$F,
(3) —SO(O)$_2$$R^{21a}$ wherein $R^{21a}$ is $C_1$–$C_{10}$-loweralkyl, aryl, aryl-$C_1$–$C_{10}$-alkyl, heterocyclic or heterocyclic-$C_1$–$C_{10}$-alkyl,
(4) —OC(O)$R^{23}$ wherein $R^{23}$ is $C_1$–$C_{10}$-loweralkyl, $C_{3-10}$-cycloalkyl, $C_3$–$C_{10}$-cycloalkyl-$C_1$–$C_{10}$-alkyl, aryl, aryl-$C_2$–$C_{10}$-alkyl, heterocyclic, heterocyclic-$C_1$–$C_{10}$-alkyl, alkoxy, —O—$C_3$–$C_{10}$-cycloalkyl, —O-aryl, —O-heterocyclic, —O-(N-succinimidyl) or 5-tetrazolyl;
(5) —OC(O)—N($R^{24}$)($R^{25}$) wherein $R^{24}$ and $R^{25}$ are independently selected from
  (a) hydrogen,
  (b) $C_1$–$C_{10}$-loweralkyl,
  (c) $C_2$–$C_{10}$-alkenyl,
  (d) $C_2$–$C_{10}$-alkynyl,
  (e) $C_3$–$C_{10}$-cycloalkyl,
  (f) substituted $C_1$–$C_{10}$-loweralkyl, substituted $C_2$–$C_{10}$-alkenyl, substituted $C_2$–$C_{10}$-alkynyl or substituted $C_{3-10}$-cycloalkyl wherein the $C_1$–$C_{10}$-loweralkyl group, the $C_2$–$C_{10}$-alkenyl group, the $C_2$–$C_{10}$-alkynyl group or the $C_{3-10}$-cycloalkyl group is substituted by one or two substituents independently selected from
    (i) hydroxy,
    (ii) —COOH,
    (iii) —CN,
    (iv) —Q—$C_1$–$C_{10}$-loweralkyl, —Q-aryl, —Q-(aryl-$C_1$–$C_{10}$-alkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH—C(O)O—, —NH—C(O)—NH—, —S(O)$_2$NH—, —NHS(O)$_2$—, —N($R^{27}$)—, —C(N$R^{27}$)NHNH— and —NHNHC(N$R^{27}$)— wherein $R^{27}$ is hydrogen, $C_1$–$C_{10}$-loweralkyl, aryl or heterocyclic,
    (v) $C_3$–$C_{10}$-cycloalkyl,
    (vi) aryl,
    (vii) heterocyclic,
    (viii) —N($R^{28}$)($R^{29}$) wherein $R^{28}$ and $R^{29}$ are independently selected from hydrogen, $C_1$–$C_{10}$-loweralkyl, hydroxy-$C_1$–$C_{10}$-alkyl, aryl and heterocyclic,
    (ix) guanidino,
    (x) —S(O)$_2$$R^{11}$ wherein $R^{11}$ is $C_1$–$C_{10}$-loweralkyl, aryl or aryl-$C_1$–$C_{10}$-alkyl,
    (xi) —OS(O)$_2$$R^{11}$ wherein $R^{11}$ is defined as above,
    (xii) —SO$_3$H,
    (xiii) —S(O)$_2$NH$_2$,
    (xiv) —S$R^{28}$ wherein $R^{28}$ is defined as above,
    (xv) halogen,
    (xvi) oxo and
    (xvii) epoxy;
  (g) aryl,
  (h) heterocyclic,
  (i) —NHC(O)—O—($C_1$–$C_{10}$-loweralkyl),
  (j) —NHC(O)-aryl,
  (k) —NHC(O)-heterocyclic and
  (l) $C_1$–$C_{10}$-loweralkyl substituted by —OC(O)—R$^f$ wherein R$^f$ is carboxy-$C_3$–$C_{10}$-alkyl or —N($R^{24}$)($R^{25}$) taken together form a nitrogen-containing heterocyclic group,
(6) —O$R^{25}$ wherein $R^{25}$ is as defined above,
(7) a protected hydroxy group,
(8) —OC(O)N(O$R^{24}$)($R^{25}$) wherein $R^{24}$ and $R^{25}$ are defined as above,
(9) —O(CH$_2$)$_i$C(O)O$R^{20}$ wherein i is one or two and $R^{20}$ is independently defined as above,
(10) —O(CH(Si(CH$_3$)$_3$))—(CH$_2$)$_j$C(O)O$R^{20}$ wherein j is zero or one and $R^{20}$ is independently defined as above,
(11) —O(CH$_2$)$_i$C(O)N($R^{24}$)($R^{25}$) wherein i, $R^{24}$ and $R^{25}$ are defined as above,
(12) —O(CH$_2$)$_i$C(O)N(O$R^{24}$)($R^{25}$) wherein i, $R^{24}$ and $R^{25}$ are defined as above,
(13) —O(CH$_2$)$_i$C(O)N($R^{24}$)(N($R^{24}$)($R^{25}$)) wherein i, $R^{24}$ and $R^{25}$ are defined as above,
(14) —O(CH$_2$)$_i$NHC(O)N($R^{24}$)($R^{25}$) wherein i, $R^{24}$ and $R^{25}$ are defined as above,
(15) —O(CH$_2$)$_i$NHC(O)N(O$R^{24}$)($R^{25}$) wherein i, $R^{24}$ and $R^{25}$ are defined as above,
(16) —O(CH$_2$)$_i$NHC(O)N($R^{24}$)(N($R^{24}$)($R^{25}$)) wherein i, $R^{24}$ and $R^{25}$ are defined as above,
(17) —OS(O)$_2$N($R^{24}$)($R^{25}$) wherein $R^{24}$ and $R^{25}$ are defined as above,
(18) —O(CH$_2$)$_i$—NHC(O)$R^{24}$ wherein $R^{24}$ is defined as above,
(19) —OCH($R^{24}$)—SH wherein $R^{24}$ is defined as above,
(20) —OCH($R^{24}$)—S—$C_1$–$C_{10}$-loweralkyl wherein $R^{24}$ is defined as above,
(21) —OCH($R^{24}$)—S-aryl wherein $R^{24}$ is defined as above and
(22) —N$_3$;

$R^{10a}$ is hydrogen and $R^{10b}$ is hydrogen, hydroxy, protected hydroxy, $C_1$–$C_{10}$-alkoxy, $C_2$–$C_{10}$-alkenyl,

91

$C_2$–$C_{10}$-alkenyloxy, halogen or —$SR^{28}$ wherein $R^{28}$ is independently defined as above or $R^{10b}$ is hydrogen and $R^{10a}$ is hydrogen, hydroxy, protected hydroxy, $C_1$–$C_{10}$-alkoxy, $C_2$–$C_{10}$-alkenyl, $C_2$–$C_{10}$-alkenyloxy, halogen or —$SR^{28}$ wherein $R^{28}$ is independently defined as above or $R^{10a}$ and $R^{10b}$ are both $C_1$–$C_{10}$-alkoxy or —$SR^{28a}$ wherein $R^{28a}$ is $C_1$–$C_{10}$-loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of $C_1$–$C_{10}$-loweralkyl, halo, halo-$C_1$–$C_{10}$-loweralkyl, halo-$C_1$–$C_{10}$-alkoxy, $C_2$–$C_{10}$-alkenyloxy, $C_1$–$C_{10}$-alkoxy, alkoxy-$C_1$–$C_{10}$-alkoxy, $C_1$–$C_{10}$-alkoxycarbonyl, $C_1$–$C_{10}$-alkoxycarbonylalkenyl, ($C_1$–$C_{10}$-alkoxycarbonyl)thio-$C_1$–$C_{10}$-alkoxy, thio-$C_1$–$C_{10}$-alkoxy, amino, $C_1$–$C_{10}$-alkylamino, $C_1$–$C_{10}$-dialkylamino, aminocarbonyl, aminocarbonyl-$C_1$–$C_{10}$-alkoxy, alkanoylamino, aryl-$C_1$–$C_{10}$-alkoxy, aryloxy, mercapto, nitro, carboxaldehyde, carboxy, carboxy-$C_2$–$C_{10}$-alkenyl, carboxy-$C_1$–$C_{10}$-alkoxy, $C_1$–$C_{10}$-alkylsulfonylamino, cyano-$C_1$–$C_{10}$-alkoxy, (heterocyclic)-$C_1$–$C_{10}$-alkoxy, hydroxy, hydroxy-$C_1$–$C_{10}$-alkoxy, phenyl, phenyl-substituted $C_2$–$C_{10}$-alkenyl, phenyl-substituted $C_2$–$C_{10}$-alkynyl, heterocyclic, —$S(O)_2NH_2$, tetrazolyl-$C_1$–$C_{10}$-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiaz-

92 olyl, thiadiazolyl, pyrrolyl, pyrimidyl, benzothienyl, compounds of the formula

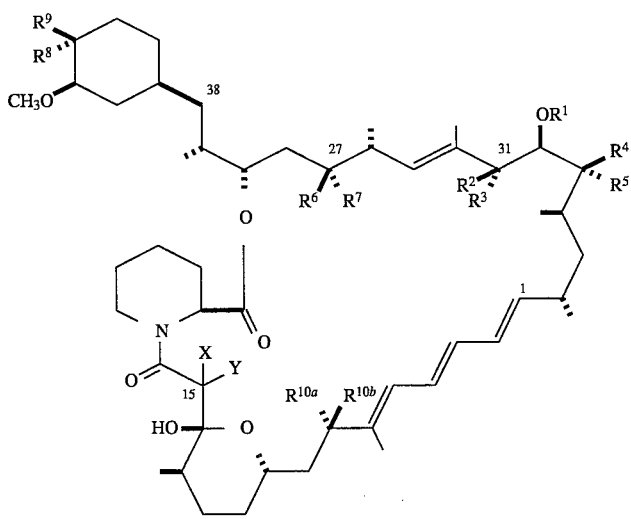

where X* is —$CH_2$— or —O— and Y* is —C(O)— or [—$C(R")_2$—]$_v$ where R" is hydrogen or $C_1$–$C_4$-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, D-arabinose, D-xylose, and D-lyxose wherein said heterocyclics are either unsubstituted or monosubstituted or disubstituted with substituents independently selected from hydroxy, halo, oxo (=O), amino, $C_1$–$C_{10}$-alkylamino, $C_1$–$C_{10}$-dialkylamino, $C_1$–$C_{10}$-alkoxy, alkoxy-$C_1$–$C_{10}$-alkoxy, alkoxy-$C_1$–$C_{10}$-alkyl, halo-$C_1$–$C_{10}$-alkyl, hydroxy, hydroxy-$C_1$–$C_{10}$-alkyl, $C_3$–$C_{10}$-cycloalkyl, aryl, aryl-$C_1$–$C_{10}$-alkyl, —COOH, —$S_3$H, —C(O)$NH_2$ and $C_1$–$C_{10}$-loweralkyl.

2. A pharmaceutical composition for immunomodulatory treatment comprising a compound having the formula:

or a pharmaceutically acceptable salt, ester, amide or prodrug thereof wherein $R^1$ is hydrogen, a hydroxy protecting group, $C_1$–$C_{10}$-loweralkyl or phenyl-substituted $C_1$–$C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1$–$C_{10}$-loweralkyl and $R^5$ is hydroxy or protected hydroxy or $R^5$ is hydrogen or phenyl-substituted $C_1$–$C_{10}$-loweralkyl and $R^4$ is hydroxy or protected hydroxy or $R^4$ and $R^5$ taken together are oxo;

$R^6$ is hydrogen or phenyl-substituted $C_1$–$C_{10}$-loweralkyl and $R^7$ is hydrogen, hydroxy or protected hydroxy or $R^7$ is hydrogen or phenyl-substituted $C_1$–$C_{10}$-loweralkyl and $R^6$ is hydroxy or protected hydroxy or $R^6$ and $R^7$ taken together are (1) oxo,
(2) diazo,
(3) =$CH_2$ (4) —O—(CH$_2$)$_2$—O—,
(5) —S—(CH$_2$)$_2$—S—,
(6) —O—(CH$_2$)$_3$—O—,
(7) —S—(CH$_2$)$_3$—S—,
(8) =N—OR$^{20}$ wherein R$^{20}$ is hydrogen, C$_2$-C$_{10}$-loweralkyl, C$_2$-C$_{10}$-alkenyl, C$_3$-$_{10}$-cycloalkyl, C$_3$-$_{10}$-cycloalkenyl, C$_3$-C$_{10}$-bicycloalkenyl, aryl, aryl-C$_1$-C$_{10}$-alkyl, heterocyclic or heterocyclic-C$_1$-C$_{10}$-alkyl, each of which is optionally substituted with C$_1$-C$_{10}$-loweralkyl, halogen, hydroxy, aryl or heterocyclic; or
(9) =N—N(R$^{21}$)(R$^{22}$) wherein R$^{21}$ and R$^{22}$ are independently selected from hydrogen, C$_1$-C$_{10}$-loweralkyl, aryl, aryl-C$_1$-C$_{10}$-alkyl, heterocyclic and heterocyclic-C$_1$-C$_{10}$-alkyl;

R$^8$ is hydrogen;

R$^9$ is
(1) —SR$^{24}$ wherein R$^{24}$ is
   (a) hydrogen,
   (b) C$_1$-C$_{10}$-loweralkyl,
   (c) C$_2$-C$_{10}$-alkenyl,
   (d) C$_2$-C$_{10}$-alkynyl,
   (e) C$_3$-C$_{10}$-cycloalkyl,
   (f) substituted C$_1$-C$_{10}$-loweralkyl, substituted C$_2$-C$_{10}$-alkenyl, substituted C$_2$-C$_{10}$-alkynyl or substituted C$_3$-C$_{10}$-cycloalkyl wherein the C$_1$-C$_{10}$-loweralkyl group, the C$_2$-C$_{10}$-alkenyl group, the C$_2$-C$_{10}$-alkynyl group or the C$_3$-$_{10}$-cycloalkyl group is substituted by one or two substituents independently selected from
      (i) hydroxy,
      (ii) —COOH,
      (iii) —CN,
      (iv) —Q—C$_1$-C$_{10}$-loweralkyl, —Q-aryl, —Q-(aryl-C$_1$-C$_{10}$-alkyl), —Q-heterocyclic or —Q-(heterocyclic-C$_1$-C$_{10}$-alkyl) wherein Q, is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein R$^{27}$ is hydrogen, C$_1$-C$_{10}$-loweralkyl, aryl or heterocyclic,
      (v) C$_3$-C$_{10}$-cycloalkyl,
      (vi) aryl,
      (vii) heterocyclic,
      (viii) —N(R$^{28}$)(R$^{29}$) wherein R$^{28}$ and R$^{29}$ are independently selected from hydrogen, C$_1$-C$_{10}$-loweralkyl, hydroxy-C$_1$l-C$_{10}$-alkyl, aryl and heterocyclic,
      (ix) guanidino,
      (x) —S(O)$_2$R$^{11}$ wherein R$^{11}$ is C$_1$-C$_{10}$-loweralkyl, aryl or aryl-C$_1$l-C$_{10}$-alkyl,
      (xi) —OS(O)$_2$R$^{11}$ wherein R$^{11}$ is defined as above,
      (xii) —SO$_3$H,
      (xiii) —S(O)$_2$NH$_2$,
      (xiv) —SR$^{28}$ wherein R$^{28}$ is defined as above,
      (xv) halogen,
      (xvi) oxo and
      (xvii) epoxy;
   (g) aryl,
   (h) heterocyclic,
   (i) —C(O)—O—(C$_1$-C$_{10}$-loweralkyl),
   (j) —C(O-aryl),
   (k) —C(O)-heterocyclic or
   (l) C$_1$-C$_{10}$-loweralkyl substituted by —OC(O)—R$^f$ wherein R$^f$ is C$_3$-C$_{10}$-carboxyalkyl,
(2) —SC(=NH) —NH$_2$,
(3) —SC(=N—NH$_2$) —NH$_2$,
(4) —Se-phenyl or
(5) —Se(O)-phenyl;

R$^{10a}$ is hydrogen and R$^{10b}$ is hydrogen, hydroxy, protected hydroxy, C$_1$-C$_{10}$-alkoxy, C$_2$-C$_{10}$-alkenyl, C$_2$-C$_{10}$-alkenyloxy, halogen or —SR$^{28}$ wherein R$^{28}$ is independently defined as above or R$^{10b}$ is hydrogen and R$^{10a}$ is hydrogen, hydroxy, protected hydroxy, C$_1$-C$_{10}$-alkoxy, C$_2$-C$_{10}$-alkenyl, C$_2$-C$_{10}$-alkenyloxy, halogen or —SR$^{28}$ wherein R$^{28}$ is independently defined as above or R$^{10a}$ and R$^{10b}$ are both C$_1$-C$_{10}$-alkoxy or —SR$^{28a}$ wherein R$^{28a}$ is C$_1$-C$_{10}$-loweralkyl, aryl or heterocyclic or R$^{10a}$ and R$^{10b}$ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of C$_1$-C$_{10}$-loweralkyl, halo, halo-C$_1$-C$_{10}$-loweralkyl, halo-C$_1$-C$_{10}$-alkoxy, C$_2$-C$_{10}$-alkenyloxy, C$_1$-C$_{10}$-alkoxy, alkoxy-C$_1$-C$_{10}$-alkoxy, C$_1$-C$_{10}$-alkoxycarbonyl, C$_1$-C$_{10}$-alkoxycarbonylalkenyl, (C$_2$-C$_{10}$-alkoxycarbonyl)thio-C$_2$-C$_{10}$-alkoxy, thio-C$_1$-C$_{10}$-alkoxy, amino, C$_1$-C$_{10}$-alkylamino, C$_1$-C$_{10}$-dialkylamino, aminocarbonyl, aminocarbonyl-C$_2$-C$_{10}$-alkoxy, alkanoylamino, aryl-C$_1$-C$_{10}$-alkoxy, aryloxy, mercapto, nitro, carboxaldehyde, carboxy, carboxy-C$_2$-C$_{10}$-alkenyl, carboxy-C$_1$-C$_{10}$-alkoxy, C$_1$-C$_{10}$-alkylsulfonylamino, cyano-C$_1$-C$_{10}$-alkoxy, (heterocyclic)-C$_1$-C$_{10}$-alkoxy, hydroxy, hydroxy-C$_1$-C$_{10}$-alkoxy, phenyl, phenyl-substituted C$_2$-C$_{10}$alkenyl, phenyl-substituted C$_2$-C$_{10}$-alkynyl, heterocyclic, —S(O)$_2$NH$_2$, tetrazolyl-C$_1$-C$_{10}$-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, benzothienyl, compounds of the formula where X* is —CH$_2$— or —O— and Y* is —C(O)— or [—C(R")$_2$—]$_v$ where R" is hydrogen or C$_1$-C$_4$-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, D-arabinose, D-xylose, and D-lyxose wherein said heterocyclics are either unsubstituted or monosubstituted or disubstituted with substituents independently selected from hydroxy, halo, oxo (=O), amino, $C_1$–$C_{10}$-alkylamino, $C_1$–$C_{10}$-dialkylamino, $C_1$–$C_{10}$-alkoxy, alkoxy-$C_1$–$C_{10}$-alkoxy, alkoxy-$C_1$–$C_{10}$-alkyl, halo-$C_1$–$C_{10}$-alkyl, hydroxy, hydroxy-$C_1$–$C_{10}$-alkyl, $C_3$–$C_{10}$-cycloalkyl, aryl, aryl-$C_1$–$C_{10}$-alkyl, —COOH, —$SO_3H$, —C(O)$NH_2$ and $C_1$–$C_{10}$-loweralkyl, in combination with a pharmaceutically acceptable carrier.

3. A pharmaceutical composition for immunomodulatory treatment comprising a compound having the formula:

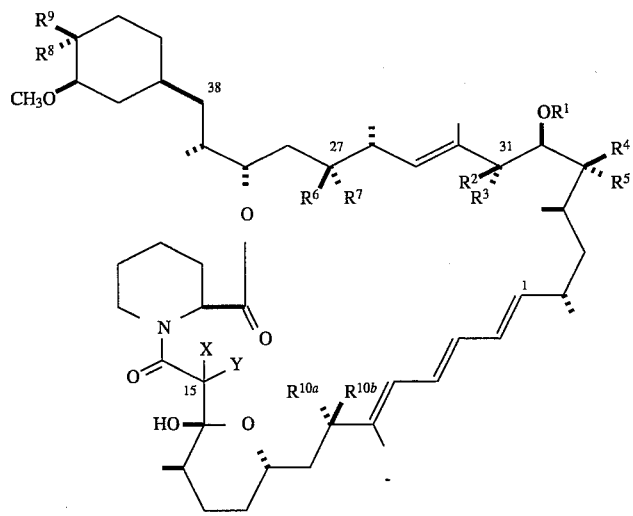

III or a pharmaceutically acceptable salt, ester, amide or prodrug thereof wherein $R^1$ is hydrogen, a hydroxy protecting group, $C_1$–$C_{10}$-loweralkyl or phenyl-substituted $C_1$–$C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1$–$C_{10}$-loweralkyl and $R^5$ is hydroxy or protected hydroxy or $R^5$ is hydrogen or phenyl-substituted $C_1$–$C_{10}$-loweralkyl and $R^4$ is hydroxy or protected hydroxy or $R^4$ and $R^5$ taken together are oxo;

$R^6$ is hydrogen or phenyl-substituted $C_1$–$C_{10}$-loweralkyl and $R^7$ is hydrogen, hydroxy or protected hydroxy or $R^7$ is hydrogen or phenyl-substituted $C_1$–$C_{10}$-loweralkyl and $R^6$ is hydroxy or protected hydroxy or $R^6$ and $R^7$ taken together are
  (1) oxo,
  (2) diazo,
  (3) =$CH_2$
  (4) —O—$(CH_2)_2$—O—,
  (5) —S—$(CH_2)_2$—S—,
  (6) —O—$(CH_2)_3$—O—,
  (7) —S—$(CH_2)_3$—S—,
  (8) =N—$OR^{20}$ wherein $R^{20}$ is hydrogen, $C_1$–$C_{10}$-loweralkyl, $C_2$–$C_{10}$-alkenyl, $C_3$–$_{10}$-cycloalkyl, $C_{3-10}$-cycloalkenyl, $C_3$–$C_{10}$-bicycloalkenyl, aryl, aryl-$C_1$–$C_{10}$-alkyl, heterocyclic or heterocyclic-$C_1$–$C_{10}$-alkyl, each of which is optionally substituted with $C_1$–$C_{10}$-loweralkyl, halogen, hydroxy, aryl or heterocyclic; or
  (9) =N—N($R^{21}$)($R^{22}$) wherein $R^{21}$ and $R^{22}$ are independently selected from hydrogen, $C_1$–$C_{10}$-loweralkyl, aryl, aryl-$C_1$–$C_{10}$-alkyl, heterocyclic and heterocyclic-$C_1$–$C_{10}$-alkyl;

$R^8$ is hydrogen;

$R^9$ is
  (1) —N($R^{24}$)($R^{25}$) wherein $R^{24}$ and $R^{25}$ are independently selected from
    (a) hydrogen,
    (b) $C_1$–$C_{10}$-loweralkyl,
    (c) $C_2$–$C_{10}$-alkenyl,
    (d) $C_2$–$C_{10}$-alkynyl,
    (e) $C_3$–$C_{10}$-cycloalkyl,
    (f) substituted $C_1$–$C_{10}$-loweralkyl, substituted $C_2$–$C_{10}$-alkenyl, substituted $C_2$–$C_{10}$-alkynyl or substituted $C_3$–$C_{10}$-cycloalkyl wherein the $C_1$–$C_{10}$-loweralkyl group, the $C_2$–$C_{10}$-alkenyl group, the $C_2$–$C_{10}$-alkynyl group or the $C_3$–$C_{10}$-cycloalkyl group is substituted by one or two substituents independently selected from
      (i) hydroxy,
      (ii) —COOH,
      (iii) —CN,
      (iv) —Q—($C_1$–$C_{10}$-loweralkyl), —Q-aryl, —Q-(aryl-$C_1$–$C_{10}$-alkyl), —Q-heterocyclic or —Q-(heterocyclic-$C_1$–$C_{10}$-alkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N($R^{27}$)—, —C(N$R^{27}$)NHNH— and —NHNHC(N$R^{27}$)— wherein $R^{27}$ is hydrogen, $C_1$–$C_{10}$-loweralkyl, aryl or heterocyclic,
      (v) $C_3$–$C_{10}$-cycloalkyl,
      (vi) aryl,
      (vii) heterocyclic,
      (viii) —N($R^{28}$)($R^{29}$) wherein $R^{28}$ and $R^{29}$ are independently selected from hydrogen, $C_1$–$C_{10}$-loweralkyl, hydroxy-$C_1$–$C_{10}$-alkyl, aryl and heterocyclic,
      (ix) guanidino,
      (x) —S(O)$_2R^{11}$ wherein $R^{11}$ is $C_1$–$C_{10}$-loweralkyl, aryl or aryl-$C_1$–$C_{10}$-alkyl,
      (xi) —OS(O)$_2R^{11}$ wherein $R^{11}$ is defined as above,

97

(xii) —SO₃H,
(xiii) —S(O)₂NH₂,
(xiv) —SR²⁸ wherein R²⁸ is defined as above,
(xv) halogen,
(xvi) oxo and
(xvii) epoxy;
(g) aryl,
(h) heterocyclic,
(i) —NHC(O)—O—(C₁–C₁₀-loweralkyl),
(j) —NHC(O)-aryl,
(k) —NHC(O)-heterocyclic and
(l) C₁–C₁₀-loweralkyl substituted by —OC(O)—R$^f$ wherein R$^f$ is C₃₋₁₀-carboxyalkyl,
(2) —N=C=O,
(3) —NHC(O)—R* or
(4) —NHS(O)₂—R* wherein R* is
(a) C₁–C₁₀-loweralkyl,
(b) C₃–C₁₀-cycloalkyl,
(c) aryl,
(d) heterocyclic,
(e) C₁–C₁₀-loweralkyl substituted by one or two substituents independently selected from
(i) hydroxy,
(ii) —COOH,
(iii) —CN,
(iv) —Q—(C₁–C₁₀-loweralkyl), —Q-aryl, —Q-(aryl-C₁–C₁₀-alkyl), —Q-heterocyclic or —Q-(heterocyclic-C₁–C₁₀-alkyl) wherein Q is —O—, —S—, —S(O)—, —S(O)₂—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)₂NH—, —NHS(O)₂—, —N(R²⁷)—, —C(NR²⁷)NHNH— and —NHNHC(NR²⁷)— wherein R²⁷ is hydrogen, C₁–C₁₀-loweralkyl, aryl or heterocyclic,
(v) C₃–C₁₀-cycloalkyl,
(vi) aryl,
(vii) heterocyclic,
(viii) —N(R²⁸)(R²⁹) wherein R²⁸ and R²⁹ are independently selected from hydrogen, C₁–C₁₀-loweralkyl, hydroxy-C₁l–C₁₀-alkyl, aryl and heterocyclic,
(ix) guanidino,
(x) —S(O)₂R¹¹ wherein R¹¹ is C₁–C₁₀-loweralkyl, aryl or aryl-C₁–C₁₀-alkyl,
(xi) —OS(O)₂R¹¹ wherein R¹¹ is defined as above,
(xii) —SO₃H,
(xiii) —S(O)₂NH₂,
(xiv) —SR²⁸ wherein R²⁸ is defined as above,
(xv) halogen,
(xvi) oxo and
(xvii) epoxy;
(f) —N(R$^a$)(R$^b$) wherein R$^a$ and R$^b$ are independently selected from hydrogen, C₁–C₁₀-loweralkyl and —N(R$^c$)(R$^d$) wherein R$^c$ and R$^d$ are independently selected from hydrogen and C₁–C₁₀-loweralkyl or
(g) —OR* wherein R* is defined as above;
R¹⁰ᵃ is hydrogen and R¹⁰ᵇ is hydrogen, hydroxy, protected hydroxy, C₁–C₁₀-alkoxy, C₂–C₁₀-alkenyl, C₂–C₁₀-alkenyloxy, halogen or —SR²⁸ wherein R²⁸ is independently defined as above or R¹⁰ᵇ is hydrogen and R¹⁰ᵃ is hydrogen, hydroxy, protected hydroxy, C₁–C₁₀-alkoxy, C₂–C₁₀-alkenyl, C₂–C₁₀-alkenyloxy, halogen

98 or —SR²⁸ wherein R²⁸ is independently defined as above or R¹⁰ᵃ and R¹⁰ᵇ are both alkoxy or —SR²⁸ᵃ wherein R²⁸ᵃ is C₁–C₁₀-loweralkyl, aryl or heterocyclic or R¹⁰ᵃ and R¹⁰ᵇ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of C₁–C₁₀-loweralkyl, halo, halo-C₁–C₁₀-loweralkyl, halo-C₁–C₁₀-alkoxy, C₂C₁₀-alkenyloxy, C₁–C₁₀-alkoxy, alkoxy-C₁–C₁₀-alkoxy, C₁–C₁₀-alkoxycarbonyl, C₁–C₁₀-alkoxycarbonylalkenyl, (C₁–C₁₀-alkoxycarbonyl)thio-C₁–C₁₀-alkoxy, thio-C₁–C₁₀-alkoxy, amino, C₁–C₁₀-alkylamino, C₁–C₁₀-dialkylamino, aminocarbonyl, aminocarbonyl-C₁–C₁₀-alkoxy, alkanoylamino, aryl-C₁–C₁₀-alkoxy, aryloxy, mercapto, nitro, carboxaldehyde, carboxy, carboxy-C₂–C₁₀-alkenyl, carboxy-C₁–C₁₀-alkoxy, C₁–C₁₀-alkylsulfonylamino, cyano-C₁–C₁₀-alkoxy, (heterocyclic)-C₁–C₁₀-alkoxy, hydroxy, hydroxy-C₁–C₁₀-alkoxy, phenyl, phenyl-substituted C₂–C₁₀-alkenyl, phenyl-substituted C₂–C₁₀-alkynyl, heterocyclic, —S(O)₂NH₂, tetrazolyl-C₁–C₁₀-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, benzothienyl, compounds of the formula

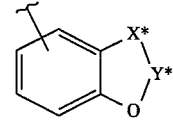

where X* is —CH₂— or —O— and Y* is —C(O)— or [—C(R")₂—]ᵥ where R" is hydrogen or C₁–C₄-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, D-arabinose, D-xylose, and D-lyxose wherein said heterocyclics are either unsubstituted or monosubstituted or disubstituted with substituents independently selected from hydroxy, halo, oxo (=O), amino, C₁–C₁₀-alkylamino, C₁–C₁₀-dialkylamino, C₁–C₁₀-alkoxy, alkoxy-C₁–C₁₀-alkoxy, alkoxy-C₁–C₁₀-alkyl, halo-C₁–C₁₀-alkyl, hydroxy, hydroxy-C₁–C₁₀-alkyl, C₃–C₁₀-cycloalkyl, aryl, aryl-C₁–C₁₀-alkyl, —COOH, —SO₃H, —C(O)NH₂ and C₁–C₁₀-loweralkyl, in combination with a pharmaceutically acceptable carrier.

4. A pharmaceutical composition for immunomodulatory treatment comprising a compound having the formula:

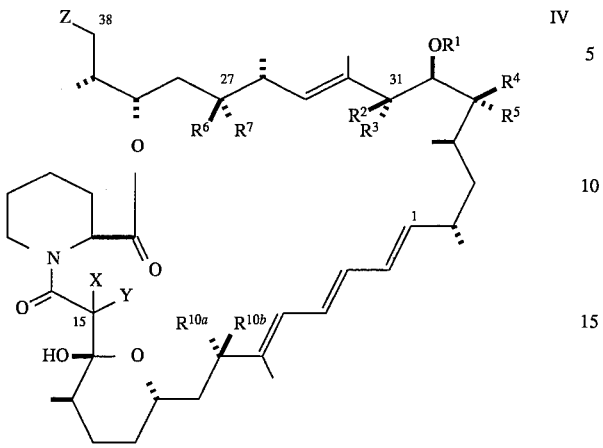

or a pharmaceutically acceptable salt, ester, amide or pro-drug thereof wherein Z is

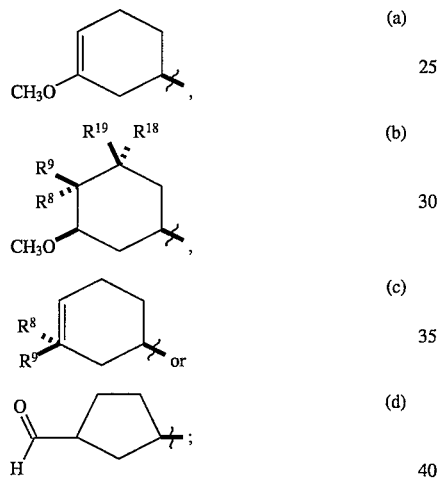

$R^1$ is hydrogen, a hydroxy protecting group, $C_1$–$C_{10}$-loweralkyl or phenyl-substituted $C_1$–$C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1$–$C_{10}$-loweralkyl and $R^5$ is hydroxy or protected hydroxy or $R^5$ is hydrogen or phenyl-substituted $C_1$–$C_{10}$-loweralkyl and $R^4$ is hydroxy or protected hydroxy or $R^4$ and $R^5$ taken together are oxo;

$R^6$ is hydrogen or phenyl-substituted $C_1$–$C_{10}$-loweralkyl and $R^7$ is hydrogen, hydroxy or protected hydroxy or $R^7$ is hydrogen or phenyl-substituted $C_1$–$C_{10}$-loweralkyl and $R^6$ is hydroxy or protected hydroxy or $R^6$ and $R^7$ taken together are (1) oxo,
(2) diazo,
(3) =$CH_2$
(4) —O—$(CH_2)_2$—O—,
(5) —S—$(CH_2)_2$—S—,
(6) —O—$(CH_2)_3$—O—,
(7) —S—$(CH_2)_3$—S—,
(8) =N—$OR^{20}$ wherein $R^{20}$ is hydrogen, $C_1$–$C_{10}$-loweralkyl, $C_2$–$C_{10}$-alkenyl, $C_3$–$C_{10}$-cycloalkyl, $C_3$–$C_{10}$-cycloalkenyl, $C_3$–$C_{10}$-bicycloalkenyl, aryl, aryl-$C_1$–$C_{10}$-alkyl, heterocyclic or heterocyclic-$C_1$–$C_{10}$-alkyl, each of which is optionally substituted with $C_1$–$C_{10}$-loweralkyl, halogen, hydroxy, aryl or heterocyclic; or
(9) =N—$N(R^{21})(R^{22})$ wherein $R^{21}$ and $R^{22}$ are independently selected from hydrogen, $C_1$–$C_{10}$-loweralkyl, aryl, aryl-$C_1$–$C_{10}$-alkyl, heterocyclic and heterocyclic-$C_1$–$C_{10}$-alkyl;

$R^8$, $R^9$, $R^{18}$ and $R^{19}$ are independently selected from
(1) hydrogen,
(2) —$OS(O)_2CF_3$,
(3) —$OS(O)_2F$,
(4) —$OS(O)_2^{21a}$ wherein $R^{21a}$ is $C_1$–$C_{10}$-loweralkyl, aryl, aryl-$C_1$–$C_{10}$-alkyl, heterocyclic or heterocyclic-$C_1$–$C_{10}$-alkyl,
(5) —$OC(O)R^{23}$ wherein $R^{23}$ is —O-aryl, —O—(N-succinimidyl), —O-benzotriazolyl, —O—2'-pyridyl or 5-tetrazolyl;
(6) —$OC(O)$—$N(R^{24})(R^{25})$ wherein $R^{24}$ and $R^{25}$ are independently selected from
  (a) hydrogen,
  (b) $C_2$–$C_{10}$-loweralkyl,
  (c) $C_2$–$C_{10}$-alkenyl,
  (d) $C_2$–$C_{10}$-alkynyl,
  (e) $C_3$–$C_{10}$-cycloalkyl,
  (f) substituted $C_1$–$C_{10}$-loweralkyl, substituted $C_2$–$C_{10}$-alkenyl, substituted $C_2$–$C_{10}$-alkynyl or substituted $C_3$–$C_{10}$-cycloalkyl wherein the $C_1$–$C_{10}$-loweralkyl group, the $C_2$–$C_{10}$-alkenyl group, the $C_2$–$C_{10}$alkynyl group or the $C_3$–$C_{10}$-cycloalkyl group is substituted by one or two substituents independently selected from
    (i) hydroxy,
    (ii) —COOH,
    (iii) —CN,
    (iv) —Q—($C_1$–$C_{10}$-loweralkyl), —Q-aryl, —Q-(aryl-$C_1$–$C_{10}$-alkyl), —Q-heterocyclic or —Q-(heterocyclic-$C_1$–$C_{10}$-alkyl) wherein Q is —O—, —S—, —S(O)—, —$S(O)_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —$S(O)_2$NH—, —$NHS(O)_2$—, —$N(R^{27})$—, —$C(NR^{27})$NHNH— and —$NHNHC(NR^{27})$— wherein $R^{27}$ is hydrogen, $C_1$–$C_{10}$-loweralkyl, aryl or heterocyclic,
    (v) $C_3$–$C_{10}$-cycloalkyl,
    (vi) aryl,
    (vii) heterocyclic,
    (viii) —$N(R^{28})(R^{29})$ wherein $R^{28}$ and $R^{29}$ are independently selected from hydrogen, $C_1$–$C_{10}$-loweralkyl, hydroxy-$C_1$l–$C_{10}$-alkyl, aryl and heterocyclic,
    (ix) guanidino,
    (x) —$S(O)_2R^{11}$ wherein $R^{11}$ is $C_1$–$C_{10}$-loweralkyl, aryl or aryl-$C_1$l–$C_{10}$-alkyl,
    (xi) —$OS(O)_2R^{11}$ wherein $R^{11}$ is defined as above,
    (xii) —$SO_3H$,
    (xiii) —$S(O)_2NH_2$,
    (xiv) —$SR^{28}$ wherein $R^{28}$ is defined as above,
    (xv) halogen,
    (xvi) oxo and
    (xvii) epoxy;
  (g) aryl,
  (h) heterocyclic,
  (i) —NHC(O)—O—($C_1$–$C_{10}$-loweralkyl),
  (j) —NHC(O)-aryl, (k) —NHC(O)-heterocyclic and (l) $C_1$–$C_{10}$-loweralkyl substituted by —OC(O)—$R^f$ wherein $R^f$ is $C_3$–$C_{10}$-carboxyalkyl or —N($R^{24}$)($R^{25}$) taken together form a nitrogen-containing heterocyclic group, (7) —$OR^{25}$ wherein $R^{25}$ is as defined above, (8) a protected hydroxy group, (9) —OC(O)N($OR^{24}$)($R^{25}$) wherein $R^{24}$ and $R^{25}$ are defined as above,

(10) —O($CH_2$)$_i$C(O)$OR^{20}$ wherein i is one or two and $R^{20}$ is independently defined as above,

(11) —O(CH(Si($CH_3$)$_3$))—($CH_2$)$_j$C(O)$OR^{20}$ wherein j is zero or one and $R^{20}$ is independently defined as above,

(12) —O($CH_2$)$_i$C(O)N($R^{24}$)($R^{25}$) wherein i, $R^{24}$ and $R^{25}$ are defined as above,

(13) —O($CH_2$)$_i$C(O)N($OR^{24}$)($R^{25}$) wherein i, $R^{24}$ and $R^{25}$ are defined as above,

(14) —O($CH_2$)$_i$C(O)N($R^{24}$)(N($R^{24}$)($R^{25}$)) wherein i, $R^{24}$ and $R^{25}$ are defined as above,

(15) —O($CH_2$)$_i$NHC(O)N($R^{24}$)($R^{25}$) wherein i, $R^{24}$ and $R^{25}$ are defined as above,

(16) —O($CH_2$)$_i$NHC(O)N($OR^{24}$)($R^{25}$) wherein i, $R^{24}$ and $R^{25}$ are defined as above,

(17) —O($CH_2$)$_i$NHC(O)N($R^{24}$)(N($R^{24}$)($R^{25}$)) wherein i, $R^{24}$ and $R^{25}$ are defined as above,

(18) —OS(O)$_2$N($R^{24}$)($R^{25}$) wherein $R^{24}$ and $R^{25}$ are defined as above,

(19) —O($CH_2$)$_i$—NHC(O)$R^{24}$ wherein $R^{24}$ is defined as above,

(20) —OCH($R^{24}$)—SH wherein $R^{24}$ is defined as above,

(21) —OCH($R^{24}$)—S—($C_1$–$C_{10}$-loweralkyl) wherein $R^{24}$ is defined as above,

(22) —OCH($R^{24}$)—S-aryl wherein $R^{24}$ is defined as above,

(23) —$N_3$,

(24) —N=C=O,

(25) —N($R^{24}$)($R^{25}$) wherein $R^{24}$ and $R^{25}$ are defined as above,

(26) —NHC(O)—$R^{24}$ wherein $R^{24}$ is defined as above,

(27) —NHC(O)—N($R^{24}$)($R^{25}$) wherein $R^{24}$ and $R^{25}$ are defined as above,

(28) —S—$R^{24}$ wherein $R^{24}$ is defined as above and

(29) —S—q—$R^{24}$ wherein q is a divalent radical selected from the group consisting of —S—, —C(O)—, —C(O)—O—, —C(O)—NH— and —C(N($R^{27}$))—NHNH— and $R^{24}$ and $R^{27}$ are defined as above, with the proviso that one of $R^8$ and $R^9$ is hydrogen and the other is not hydrogen and one of $R^{18}$ and $R^{19}$ is hydrogen and the other is not hydrogen; or $R^8$ and $R^9$ taken together are (1) oxo, (2) =N—O—$R^{24}$ wherein $R^{24}$ is defined as above or (3) =N—N($R^{24}$)($R^{25}$) wherein $R^{24}$ and $R^{25}$ are defined as above; or $R^{18}$ and $R^{19}$ taken together are (1) oxo, (2) =N—O—$R^{24}$ wherein $R^{24}$ is independently defined as above or (3) =N—N($R^{24}$)($R^{25}$) wherein $R^{24}$ and $R^{25}$ are independently defined as above; or one of $R^8$ and $R^9$ taken together with one of $R^{18}$ and $R^{19}$ form a heterocyclic ring with the others of $R^8$, $R^9$, $R^{18}$ and $R^{19}$ being hydrogen or together forming a bond; or $R^8$ and $R^{18}$ are hydrogen and $R^{8'}$ and $R^{19}$ form a bond;

$R^{10a}$ is hydrogen and $R^{10b}$ is hydrogen, hydroxy, protected hydroxy, $C_1$–$C_{10}$-alkoxy, $C_2$–$C_{10}$-alkenyl, $C_2$–$C_{10}$-alkenyloxy, halogen or —$SR^{28}$ wherein $R^{28}$ is independently defined as above or $R^{10b}$ is hydrogen and $R^{10a}$ is hydrogen, hydroxy, protected hydroxy, $C_1$–$C_{10}$-alkoxy, $C_2$–$C_{10}$-alkenyl, $C_2$–$C_{10}$-alkenyloxy, halogen or —$SR^{28}$ wherein $R^{28}$ is independently defined as above or $R^{10a}$ and $R^{10b}$ are both alkoxy or —$SR^{28a}$ wherein $R^{28a}$ is $C_1$–$C_{10}$-loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of $C_1$–$C_{10}$-loweralkyl, halo, halo-$C_1$–$C_{10}$-loweralkyl, halo-$C_1$–$C_{10}$-alkoxy, $C_2C_{10}$-alkenyloxy, $C_1$–$C_{10}$-alkoxy, alkoxy-$C_1$–$C_{10}$-alkoxy, $C_1$–$C_{10}$-alkoxycarbonyl, $C_1$–$C_{10}$-alkoxycarbonylalkenyl, ($C_1$–$C_{10}$-alkoxycarbonyl)thio-$C_1$–$C_{10}$-alkoxy, thio-$C_1$–$C_{10}$-alkoxy, amino, $C_1$–$C_{10}$-alkylamino, $C_1$–$C_{10}$-dialkylamino, aminocarbonyl, aminocarbonyl-$C_1$–$C_{10}$-alkoxy, alkanoylamino, aryl-$C_1$–$C_{10}$-alkoxy, aryloxy, mercapto, nitro, carboxaldehyde, carboxy, carboxy-$C_2$–$C_{10}$-alkenyl, carboxy-$C_1$–$C_{10}$-alkoxy, $C_1$–$C_{10}$-alkylsulfonylamino, cyano-$C_1$–$C_{10}$-alkoxy, (heterocyclic)-$C_1$–$C_{10}$-alkoxy, hydroxy, hydroxy-$C_1$–$C_{10}$-alkoxy, phenyl, phenyl-substituted $C_2$–$C_{10}$-alkenyl, phenyl-substituted $C_2$–$C_{10}$-alkynyl, heterocyclic, —S(O)$_2$$NH_2$, tetrazolyl-$C_1$–$C_{10}$-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, benzothienyl, compounds of the formula

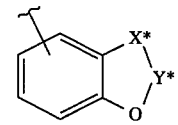

where X* is —$CH_2$— or —O— and Y* is —C(O)— or [—C(R")$_2$—]$_v$ where R" is hydrogen or $C_1$–$C_4$-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, D-arabinose, D-xylose, and D-lyxose wherein said heterocyclics are either unsubstituted or monosubstituted or disubstituted with substituents independently selected from hydroxy, halo, oxo (=O), amino, $C_1$–$C_{10}$-alkylamino, $C_1$–$C_{10}$-dialkylamino, $C_1$–$C_{10}$-alkoxy, alkoxy-$C_1$–$C_{10}$-alkoxy, alkoxy-$C_1$–$C_{10}$-alkyl, halo-$C_1$–$C_{10}$-alkyl, hydroxy, hydroxy-$C_1$–$C_{10}$-alkyl, $C_3$–$C_{10}$-cycloalkyl, aryl, aryl-$C_1$–$C_{10}$-alkyl, —COOH, —$SO_3H$, —C(O)$NH_2$

103 and $C_1-C_{10}$-loweralkyl, in combination with a pharmaceutically acceptable carrier.

5. A pharmaceutical composition for immunomodulatory treatment comprising a compound having the formula:

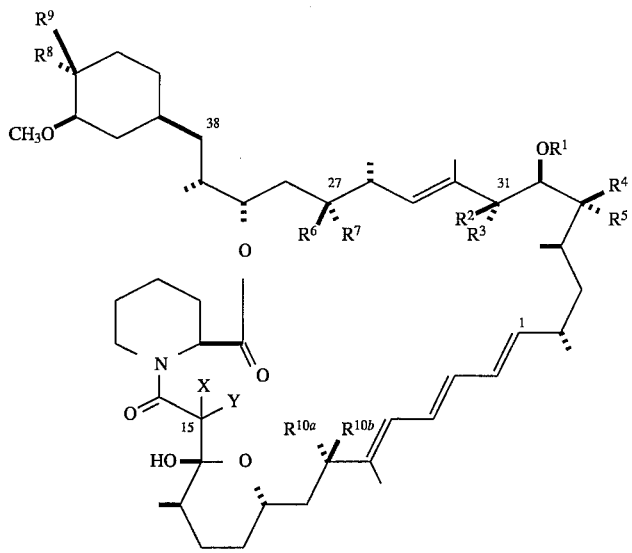

or a pharmaceutically acceptable salt, ester, amide or prodrug thereof wherein $R^1$ is hydrogen, a hydroxy protecting group, $C_1-C_{10}$-loweralkyl or phenyl-substituted $C_1-C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1-C_{10}$-loweralkyl and $R^5$ is hydroxy or protected hydroxy or $R^5$ is hydrogen or phenyl-substituted $C_1-C_{10}$-loweralkyl and $R^4$ is hydroxy or protected hydroxy or $R^4$ and $R^5$ taken together are oxo;

$R^6$ is hydrogen or phenyl-substituted $C_1-C_{10}$-loweralkyl and $R^7$ is hydrogen, hydroxy or protected hydroxy or $R^7$ is hydrogen or phenyl-substituted $C_1-C_{10}$-loweralkyl and $R^6$ is hydroxy or protected hydroxy or $R^6$ and $R^7$ taken together are
(1) oxo,
(2) diazo,
(3) =CH$_2$
(4) —O—(CH$_2$)$_2$—O—,
(5) —S—(CH$_2$)$_2$—S—,
(6) —O—(CH$_2$)$_3$—O—,
(7) —S—(CH$_2$)$_3$—S—,
(8) =N—OR$^{20}$ wherein $R^{20}$ is hydrogen, $C_1-C_{10}$-loweralkyl, $C_2-C_{10}$-alkenyl, $C_{3-10}$-cycloalkyl, $C_{3-10}$-cycloalkenyl, $C_{3-10}$-bicycloalkenyl, aryl, aryl-$C_1-C_{10}$-alkyl, heterocyclic or heterocyclic-$C_1-C_{10}$-alkyl, each of which is optionally substituted with $C_1-C_{10}$-loweralkyl, halogen, hydroxy, aryl or heterocyclic; or
(9) =N—N(R$^{21}$)(R$^{22}$) wherein $R^{21}$ and $R^{22}$ are independently selected from hydrogen, $C_1-C_{10}$-loweralkyl, aryl, aryl-$C_1-C_{10}$-alkyl, heterocyclic and heterocyclic-$C_1-C_{10}$-alkyl;

$R^8$ is
(1) —OC(O)N(OR$^{20}$)(R$^{24}$) or
(2) —O—C(O)—NHN(R$^{24}$)(R$^{25}$) wherein $R^{20}$ is hydrogen, $C_1-C_{10}$-loweralkyl, $C_2-C_{10}$-alkenyl,

104

$C_{3-10}$-cycloalkyl, $C_{3-10}$-cycloalkenyl, $C_{3-10}$-bicycloalkenyl, aryl or heterocyclic, each of which is optionally substituted with $C_1-C_{10}$-loweralkyl,

V hydroxy, aryl or heterocyclic and $R^{24}$ and $R^{25}$ are independently selected from
(a) hydrogen,
(b) $C_1-C_{10}$-loweralkyl,
(c) $C_2-C_{10}$-alkenyl,
(d) $C_2-C_{10}$-alkynyl,
(e) $C_3-C_{10}$-cycloalkyl,
(f) substituted $C_1-C_{10}$-loweralkyl, substituted $C_2-C_{10}$-alkenyl, substituted $C_2-C_{10}$-alkynyl or substituted $C_{3-10}$-cycloalkyl wherein the $C_1-C_{10}$-loweralkyl group, the $C_2-C_{10}$-alkenyl group, the $C_2-C_{10}$-alkynyl group or the $C_{3-10}$-cycloalkyl group is substituted by one or two substituents independently selected from
(i) hydroxy,
(ii) —COOH,
(iii) —CN,
(iv) —Q—$C_1-C_{10}$-loweralkyl, —Q-aryl, —Q-(aryl-$C_1-C_{10}$-alkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NH-C(O)O—, —NH—C(O)—NH—, —S(O)$_2$NH—, —NHS(O)$_2$—, —N(R$^{27}$)—, —C(NR$^{27}$)NHNH— and —NHNHC(NR$^{27}$)— wherein $R^{27}$ is hydrogen, $C_1-C_{10}$-loweralkyl, aryl or heterocyclic,
(v) $C_3-C_{10}$-cycloalkyl,
(vi) aryl,
(vii) heterocyclic,
(viii) —N(R$^{28}$)(R$^{29}$) $R^{28}$ and $R^{29}$ are independently selected from hydrogen, $C_1-C_{10}$-loweralkyl, hydroxy-$C_1$l–$C_{10}$-alkyl, aryl and heterocyclic,
(ix) guanidino,
(x) —S(O)$_2$R$^{11}$ wherein $R^{11}$ is $C_1-C_{10}$-loweralkyl, aryl or aryl-$C_1-C_{10}$-alkyl,
(xi) —OS(O)$_2$R$^{11}$ wherein $R^{11}$ is defined as above, (xii) —SO$_3$H,
(xiii) —S(O)$_2$NH$_2$,
(xiv) —SR$^{28}$ wherein R$^{28}$ is defined as above,
(xv) halogen,
(xvi) oxo and
(xvii) epoxy;
(g) aryl,
(h) heterocyclic,
(i) —NHC(O)—O—(C$_1$–C$_{10}$-loweralkyl),
(j) —NHC(O)-aryl,
(k) —NHC(O)-heterocyclic or
(l) C$_1$–C$_{10}$-loweralkyl substituted by —OC(O)—R$^f$ wherein R$^f$ is C$_3$–C$_{10}$-carboxyalkyl or —N(R$^{24}$)(R$^{2\text{-}5}$) taken together form a nitrogen-containing heterocyclic group;

R$^9$ is hydrogen; R$^{10a}$ is hydrogen and R$^{10b}$ is hydrogen, hydroxy, protected hydroxy, C$_1$–C$_{10}$-alkoxy, C$_2$–C$_{10}$-alkenyl, C$_2$–C$_{10}$-alkenyloxy, halogen or —SR$^{28}$ wherein R$^{28}$ is independently defined as above or R$^{10b}$ is hydrogen and R$^{10a}$ is hydrogen, hydroxy, protected hydroxy, C$_1$–C$_{10}$-alkoxy, C$_2$–C$_{10}$-alkenyl, C$_2$–C$_{10}$-alkenyloxy, halogen or —SR$^{28}$ wherein R$^{28}$ is independently defined as above or R$^{10a}$ and R$^{10b}$ are both C$_1$–C$_{10}$-alkoxy or —SR$^{28a}$ wherein R$^{28a}$ is C$_1$–C$_{10}$-loweralkyl, aryl or heterocyclic or R$^{10a}$ and R$^{10b}$ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of C$_1$–C$_{10}$-loweralkyl, halo, halo-C$_1$–C$_{10}$-loweralkyl, halo-C$_1$–C$_{10}$-alkoxy, C$_2$–C$_{10}$-alkenyloxy, C$_1$–C$_{10}$-alkoxy, alkoxy-C$_1$–C$_{10}$-alkoxy, C$_1$–C$_{10}$-alkoxycarbonyl, C$_1$–C$_{10}$-alkoxycarbonylalkenyl, (C$_1$–C$_{10}$-alkoxycarbonyl)thio-C$_1$–C$_{10}$-alkoxy, thio-C$_1$–C$_{10}$-alkoxy, amino, C$_1$–C$_{10}$-alkylamino, C$_1$–C$_{10}$-dialkylamino, aminocarbonyl, aminocarbonyl-C$_1$–C$_{10}$-alkoxy, alkanoylamino, aryl-C$_1$–C$_{10}$-alkoxy, aryloxy, mercapto, nitro, carboxaldehyde, carboxy, carboxy-C$_2$–C$_{10}$-alkenyl, carboxy-C$_1$–C$_{10}$-alkoxy, C$_1$–C$_{10}$-alkylsulfonylamino, cyano-C$_1$–C$_{10}$-alkoxy, (heterocyclic)-C$_1$–C$_{10}$-alkoxy, hydroxy, hydroxy-C$_1$–C$_{10}$-alkoxy, phenyl, phenyl-substituted C$_2$–C$_{10}$-alkenyl, phenyl-substituted C$_2$–C$_{10}$-alkynyl, heterocyclic, —S(O)$_2$NH$_2$, tetrazolyl-C$_1$–C$_{10}$-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, benzothienyl, compounds of the formula

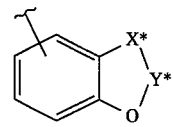

where X* is —CH$_2$— or —O— and Y* is —C(O)— or [—C(R")$_2$—]$_v$ where R" is hydrogen or C$_1$–C$_4$-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, D-arabinose, D-xylose, and D-lyxose wherein said heterocyclics are either unsubstituted or monosubstituted or disubstituted with substituents independently selected from hydroxy, halo, oxo (=O), amino, C$_1$–C$_{10}$-alkylamino, C$_1$–C$_{10}$-dialkylamino, C$_1$–C$_{10}$-alkoxy, alkoxy-C$_1$–C$_{10}$-alkoxy, alkoxy-C$_1$–C$_{10}$-alkyl, halo-C$_1$–C$_{10}$-alkyl, hydroxy, hydroxy-C$_1$–C$_{10}$-alkyl, C$_3$–C$_{10}$-cycloalkyl, aryl, aryl-C$_1$–C$_{10}$-alkyl, —COOH, —SO$_3$H, —C(O)NH$_2$ and C$_1$–C$_{10}$-loweralkyl, in combination with a pharmaceutically acceptable carrier.

6. A pharmaceutical composition for immunomodulatory treatment comprising a compound having the formula:

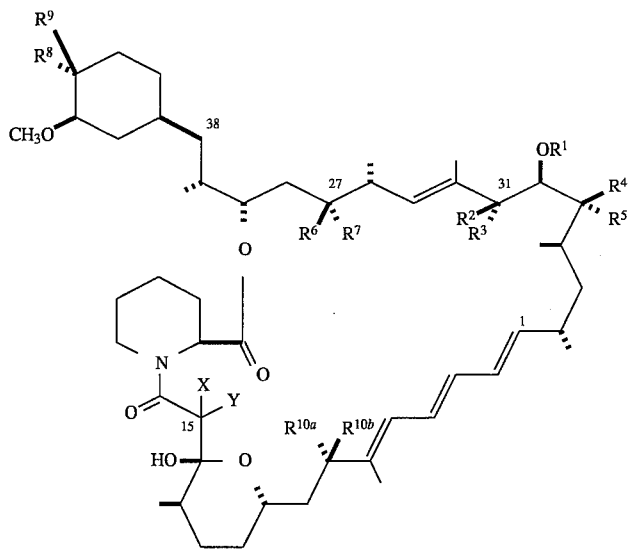

VII or a pharmaceutically acceptable salt, ester, amide or prodrug thereof wherein $R^1$ is hydrogen, a hydroxy protecting group, $C_1$–$C_{10}$-loweralkyl or phenyl-substituted $C_1$–$C_{10}$-loweralkyl;

$R^2$ is hydrogen and $R^3$ is hydroxy or protected hydroxy or $R^2$ and $R^3$ taken together are oxo;

$R^4$ is hydrogen or phenyl-substituted $C_1$–$C_{10}$-loweralkyl and $R^5$ is hydroxy or protected hydroxy or $R^5$ is hydrogen or phenyl-substituted $C_1$–$C_{10}$-loweralkyl and $R^4$ is hydroxy or protected hydroxy or $R^4$ and $R^5$ taken together are oxo;

$R^6$ is hydrogen or phenyl-substituted $C_1$–$C_{10}$-loweralkyl and $R^7$ is hydrogen, hydroxy or protected hydroxy or $R^7$ is hydrogen or phenyl-substituted $C_1$–$C_{10}$-loweralkyl and $R^6$ is hydroxy or protected hydroxy or $R^6$ and $R^7$ taken together are
- (1) oxo,
- (2) diazo,
- (3) =$CH_2$
- (4) —O—$(CH_2)_2$—O—,
- (5) —S—$(CH_2)_2$—S—,
- (6) —O—$(CH_2)_3$—O—,
- (7) —S—$(CH_2)_3$—S—,
- (8) =N—$OR^{20}$ wherein $R^{20}$ is hydrogen, $C_1$–$C_{10}$-loweralkyl, $C_2$–$C_{10}$-alkenyl, $C_3$–$_{10}$-cycloalkyl, $C_3$–$_{10}$-cycloalkenyl, $C_3$–$_{10}$-bicycloalkenyl, aryl, aryl-$C_1$–$C_{10}$-alkyl, heterocyclic or heterocyclic-$C_1$–$C_{10}$-alkyl, each of which is optionally substituted with $C_1$–$C_{10}$-loweralkyl, halogen, hydroxy, aryl or heterocyclic; or
- (9) =N—$N(R^{21})(R^{22})$ wherein $R^{21}$ and $R^{22}$ are independently selected from hydrogen, $C_1$–$C_{10}$-loweralkyl, aryl, aryl-$C_1$–$C_{10}$-alkyl, heterocyclic and heterocyclic-$C_1$–$C_{10}$-alkyl;

$R^8$ is
- (1) —OC(O)N($OR^{20}$)($R^{24}$) or
- (2) —O—C(O)—NHN($R^{24}$)($R^{25}$) wherein $R^{20}$ is hydrogen, $C_1$–$C_{10}$-loweralkyl, $C_2$–$C_{10}$-alkenyl, $C_3$–$C_{10}$-cycloalkyl, $C_3$–$_{10}$-cycloalkenyl, $C_3$–$C_{10}$-bicycloalkenyl, aryl or heterocyclic, each of which is optionally substituted with $C_1$–$C_{10}$-loweralkyl, hydroxy, aryl or heterocyclic and $R^{24}$ and $R^{25}$ are independently selected from (a) hydrogen,
(b) $C_1$–$C_{10}$-loweralkyl,
(c) $C_2$–$C_{10}$-alkenyl,
(d) $C_2$–$C_{10}$-alkynyl,
(e) $C_3$–$C_{10}$-cycloalkyl,
(f) substituted $C_1$–$C_{10}$-loweralkyl, substituted $C_2$–$C_{10}$-alkenyl, substituted $C_2$–$C_{10}$-alkynyl or substituted $C_3$–$_{10}$-cycloalkyl wherein the $C_1$–$C_{10}$-loweralkyl group, the $C_2$–$C_{10}$-alkenyl group, the $C_2$–$C_{10}$-alkynyl group or the $C_3$–$C_{10}$-cycloalkyl group is substituted by one or two substituents independently selected from
  - (i) hydroxy,
  - (ii) —COOH,
  - (iii) —CN,
  - (iv) —Q—$C_1$–$C_{10}$-loweralkyl, —Q-aryl, —Q-(aryl-$C_1$–$C_{10}$-alkyl), —Q-heterocyclic or —Q-(heterocyclicalkyl) wherein Q is —O—, —S—, —S(O)—, —S(O)$_2$—, —C(O)—, —OC(O)—, —C(O)O—, —C(O)C(O)—O—, —O—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N($R^{27}$)—, —C(N$R^{27}$)NHNH— and —NHNHC(N$R^{27}$)— wherein $R^{27}$ is hydrogen, $C_1$–$C_{10}$-loweralkyl, aryl or heterocyclic,
  - (v) $C_3$–$C_{10}$-cycloalkyl,
  - (vi) aryl,
  - (vii) heterocyclic,
  - (viii) —N($R^{28}$)($R^{29}$) $R^{28}$ and $R^{29}$ are independently selected from hydrogen, $C_1$–$C_{10}$-loweralkyl, hydroxy-$C_1$1–$C_{10}$-alkyl, aryl and heterocyclic,
  - (ix) guanidino,
  - (x) —S(O)$_2$$R^{11}$ wherein $R^{11}$ is $C_1$–$C_{10}$-loweralkyl, aryl or aryl-$C_1$–$C_{10}$-alkyl,
  - (xi) —OS(O)$_2$$R^{11}$ wherein $R^{11}$ is defined as above,
  - (xii) —SO$_3$H,
  - (xiii) —S(O)$_2$NH$_2$,
  - (xiv) —S$R^{28}$ wherein $R^{28}$ is defined as above,
  - (xv) halogen,
  - (xvi) oxo and
  - (xvii) epoxy;

(g) aryl,
(h) heterocyclic,
(i) —NHC(O)—O—($C_1$–$C_{10}$-loweralkyl),
(j) —NHC(O)—aryl,
(k) —NHC(O)—heterocyclic or
(l) $C_1$–$C_{10}$-loweralkyl substituted by —OC(O)—$R^f$ wherein $R^f$ is $C_3$–$C_{10}$-carboxyalkyl or —N($R^{24}$)($R^{25}$) taken together form a nitrogen-containing heterocyclic group,
(3) —O($CH_2$)$_i$C(O)N(O$R^{24}$)($R^{25}$) wherein i, $R^{24}$ and $R^{25}$ are defined as above,
(4) —O($CH_2$)$_i$C(O)N($R^{24}$)(N($R^{24}$)($R^{25}$)) wherein i, $R^{24}$ and $R^{25}$ are defined as above,
(5) —O($CH_2$)$_i$NHC(O)N($R^{24}$)($R^{25}$) wherein i, $R^{24}$ and $R^{25}$ are defined as above,
(6) —($CH_2$)$_i$NHC(O)N(O$R^{24}$)($R^{25}$) wherein i, $R^{24}$ and $R^{25}$ are defined as above or
(7) —($CH_2$)$_i$NHC(O)N($R^{24}$)(N($R^{24}$)($R^{25}$)) wherein i, $R^{24}$ and $R^{25}$ are defined as above;

$R^9$ is hydrogen;

$R^{10a}$ is hydrogen and $R^{10b}$ is hydrogen, hydroxy, protected hydroxy, $C_1$–$C_{10}$-alkoxy, $C_2$–$C_{10}$-alkenyl, $C_2$–$C_{10}$-alkenyloxy, halogen or —$SR^{28}$ wherein $R^{28}$ is independently defined as above or $R^{10b}$ is hydrogen and $R^{10a}$ is hydrogen, hydroxy, protected hydroxy, $C_1$–$C_{10}$-alkoxy, $C_2$–$C_{10}$-alkenyl, $C_2$–$C_{10}$-alkenyloxy, halogen or —$SR^{28}$ wherein $R^{28}$ is independently defined as above or $R^{10a}$ and $R^{10b}$ are both $C_1$–$C_{10}$-alkoxy or —$SR^{28a}$ wherein $R^{28a}$ is $C_1$–$C_{10}$-loweralkyl, aryl or heterocyclic or $R^{10a}$ and $R^{10b}$ taken together are oxo; and X is hydrogen and Y is hydrogen, hydroxy or protected hydroxy or Y is hydrogen and X is hydroxy or protected hydroxy or X and Y taken together are oxo wherein at each occurrence the term "aryl" is independently selected from phenyl, naphthyl, fluorenyl, (1,2,3,4-)-tetrahydronaphthyl, indenyl and indanyl which is either unsubstituted or substituted with one, two, or three substituents independently selected from the group consisting of $C_1$–$C_{10}$-loweralkyl, halo, halo-$C_1$–$C_{10}$-loweralkyl, halo-$C_1$–$C_{10}$-alkoxy, $C_2$–$C_{10}$-alkenyloxy, $C_1$–$C_{10}$-alkoxy, alkoxy-$C_1$–$C_{10}$-alkoxy, $C_1$–$C_{10}$-alkoxycarbonyl, $C_1$–$C_{10}$-alkoxycarbonylalkenyl, ($C_1$–$C_{10}$-alkoxycarbonyl)thio-$C_1$–$C_{10}$-alkoxy, thio-$C_1$–$C_{10}$-alkoxy, amino, $C_1$–$C_{10}$-alkylamino, $C_1$–$C_{10}$-dialkylamino, aminocarbonyl, aminocarbonyl-$C_1$–$C_{10}$-alkoxy, alkanoylamino, aryl-$C_1$–$C_{10}$-alkoxy, aryloxy, mercapto, nitro, carboxaldehyde, carboxy, carboxy-$C_2$–$C_{10}$-alkenyl, carboxy-$C_1$–$C_{10}$-alkoxy, $C_1$–$C_{10}$-alkylsulfonylamino, cyano-$C_1$–$C_{10}$-alkoxy, (heterocyclic)-$C_1$–$C_{10}$-alkoxy, hydroxy, hydroxy-$C_1$–$C_{10}$-alkoxy, phenyl, phenyl-substituted $C_2$–$C_{10}$-alkenyl, phenyl-substituted $C_2$–$C_{10}$-alkynyl, heterocyclic, —S(O)$_2$NH$_2$, tetrazolyl-$C_1$–$C_{10}$-alkoxy, tetrafluorophenyl and pentafluorophenyl and at each occurrence the term "heterocyclic" is independently selected from indolyl, quinolyl, isoquinolyl, tetrahydroquinolyl, benzofuryl, dihydrobenzofuryl, benzothienyl, azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl, benzothienyl, compounds of the formula

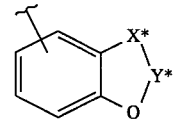

where X* is —CH$_2$— or —O— and Y* is —C(O)— or [—C(R")$_2$—]$_v$ where R" is hydrogen or $C_1$–$C_4$-alkyl and v is 1, 2 or 3, pyridin-2-on-1-yl, pyridin-4-on-1-yl, D-allose, D-altrose, D-glucose, D-mannose, D-gulose, D-idose, D-galactose, D-talose, D-ribose, ribose, D-arabinose, D-xylose, and D-lyxose wherein said heterocyclics are either unsubstituted or monosubstituted or disubstituted with substituents independently selected from hydroxy, halo, oxo (=O), amino, $C_1$–$C_{10}$-alkylamino, $C_1$–$C_{10}$-dialkylamino, $C_1$–$C_{10}$-alkoxy, alkoxy-$C_1$–$C_{10}$-alkoxy, alkoxy-$C_1$–$C_{10}$-alkyl, halo-$C_1$–$C_{10}$-alkyl, hydroxy, hydroxy-$C_1$–$C_{10}$-alkyl, $C_3$–$C_{10}$-cycloalkyl, aryl, aryl-$C_2$–$C_{10}$-alkyl, —COOH, —SO$_3$H, —C(O)NH$_2$ and $C_1$–$C_{10}$-loweralkyl, in combination with a pharmaceutically acceptable carrier.

* * * * *

UNITED STATES PATENT AND TRADEMARK OFFICE
CERTIFICATE OF CORRECTION

PATENT NO. : 5,583,139  
DATED : December 10, 1996  
INVENTOR(S) : Or, et. Al.

Page 1 of 3

It is certified that error appears in the above-indentified patent and that said Letters Patent is hereby corrected as shown below:

On the title page, item [54] and column 1, line 1, change "MARCOLIDE" to --MACROLIDE--.

Column 89, line 35, change "-SO(O)$_2$R$^{21a}$" to -- -OS(O)$_2$R$^{21a}$--.

Column 89, line 39, change "C$_{3-10}$" to --C$_3$-C$_{10}$--.

Column 89, line 40, change "C$_2$-C$_{10}$" to --C$_1$-C$_{10}$--.

Column 89, line 53, change "C$_{3-10}$" to --C$_3$-C$_{10}$--.

Column 92, line 21, change "-S$_3$H" to -- -SO$_3$H--.

Column 93, line 6, change "C$_{3-10}$" to --C$_3$-C$_{10}$--.

Column 93, line 7, change "C$_{3-10}$" to --C$_3$-C$_{10}$--.

Column 93, line 28, change "C$_{3-10}$" to --C$_3$-C$_{10}$--.

Column 93, line 51, change "C$_1$l-C$_{10}$" to --C$_1$-C$_{10}$--.

Column 93, line 55, change "C$_1$l-C$_{10}$" to --C$_1$-C$_{10}$--.

Column 93, line 67, change "-C(O-aryl" to -- -C(O)-aryl--.

Column 94, line 31, change "(C$_2$-C$_{10}$-alkoxycarbonyl)thio-C$_2$-C$_{10}$-alkoxy" to --(C$_1$-C$_{10}$-alkoxycarbonyl)thio-C$_1$-C$_{10}$-alkoxy--.

Column 94, line 33, change "aminocarbonyl-C$_2$-C$_{10}$" to --aminocarbonyl-C$_1$-C$_{10}$--.

Column 94, line 37, change "alkylsulfonylamino" to --alkylsulfonylamino--.

UNITED STATES PATENT AND TRADEMARK OFFICE
CERTIFICATE OF CORRECTION

PATENT NO. : 5,583,139
DATED : December 10, 1996
INVENTOR(S) : Or, et. Al.

It is certified that error appears in the above-indentified patent and that said Letters Patent is hereby corrected as shown below:

Column 95, line 60, change "$C_{3-10}$-cycloalkyl" to --$C_3$-$C_{10}$-cycloalkyl--.

Column 95, line 61, change "$C_{3-10}$-cycloalkenyl" to --$C_3$-$C_{10}$-cycloalkenyl--.

Column 97, line 13, change "$C_{3-10}$" to --$C_3$-$C_{10}$--.

Column 97, line 43, change "$C_1 l$-$C_{10}$" to --$C_1$-$C_{10}$--.

Column 98, line 15, change "$C_2 C_{10}$" to --$C_2$-$C_{10}$--.

Column 100, line 11, change "-$OS(O)_2{}^{21a}$" to -- -$OS(O)_2 R^{21a}$--.

Column 100, line 20, change "$C_2$-$C_{10}$" to --$C_1$-$C_{10}$--.

Column 100, line 51, change "$C_1 l$-$C_{10}$" to --$C_1$-$C_{10}$--.

Column 100, line 55, change "$C_1 l$-$C_{10}$" to --$C_1$-$C_{10}$--.

Column 102, line 20, change "$C_2 C_{10}$" to --$C_2$-$C_{10}$--.

Column 102, line 58, change "2or" to --2 or--.

Column 103, line 54, change "$C_{3-10}$-cycloalkyl" to --$C_3$-$C_{10}$-cycloalkyl--.

Column 103, line 55, change "$C_{3-10}$-cycloalkenyl, $C_{3-10}$-bicycloalkenyl" to --$C_3$-$C_{10}$-cycloalkenyl, $C_3$-$C_{10}$-bicycloalkenyl--.

Column 104, line 1, change "$C_{3-10}$-cycloalkyl, $C_{3-10}$-cycloalkenyl, $C_{3-10}$" to --$C_3$-$C_{10}$-cycloalkyl, $C_3$-$C_{10}$-cycloalkenyl, $C_3$-$C_{10}$--.

Column 104, line 36, change "$C_{3-10}$" to --$C_3$-$C_{10}$--.

UNITED STATES PATENT AND TRADEMARK OFFICE
CERTIFICATE OF CORRECTION

PATENT NO. : 5,583,139
DATED : December 10, 1996
INVENTOR(S) : Or, et. Al.

It is certified that error appears in the above-indentified patent and that said Letters Patent is hereby corrected as shown below:

Column 104, line 38, change "$C_{3-10}$" to --$C_3$-$C_{10}$--.

Column 104, line 61, change "$C_1$l-$C_{10}$" to --$C_1$-$C_{10}$--.

Column 107, line 49, change "$C_{3-10}$-cycloalkyl" to --$C_3$-$C_{10}$-cycloalkyl--.

Column 107, line 50, change "$C_{3-10}$-cycloalkenyl, $C_{3-10}$-bicycloalkenyl" to --$C_3$-$C_{10}$-cycloalkenyl, $C_3$-$C_{10}$-bicycloalkenyl--.

Column 108, line 30, change "$C_{3-10}$" to --$C_3$-$C_{10}$--.

Column 108, line 55, change "$C_1$l-$C_{10}$" to --$C_1$-$C_{10}$--.

Column 110, line 36, delete "ribose,".

Column 110, line 43, change "$C_2$-$C_{10}$" to --$C_1$-$C_{10}$--.

Column 93, line 5, change "$C_2$-$C_{10}$-" to --$C_1$-$C_{10}$- --.

Signed and Sealed this

Fifteenth Day of April, 1997

Attest:

BRUCE LEHMAN

Attesting Officer

Commissioner of Patents and Trademarks